United States Patent
Alibhai et al.

(10) Patent No.: US 6,657,046 B1
(45) Date of Patent: Dec. 2, 2003

(54) INSECT INHIBITORY LIPID ACYL HYDROLASES

(75) Inventors: Murtaza F. Alibhai, Chesterfield, MO (US); Timothy J. Rydel, St. Charles, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 09/755,274

(22) Filed: Jan. 5, 2001

Related U.S. Application Data

(60) Provisional application No. 60/219,912, filed on Jul. 21, 2000, and provisional application No. 60/174,669, filed on Jan. 6, 2000.

(51) Int. Cl.[7] .................. C07K 14/415; C12N 9/14; A61K 38/46
(52) U.S. Cl. .................. 530/350; 435/195; 424/94.6
(58) Field of Search .................. 530/350; 435/195; 424/94.6

(56) References Cited

U.S. PATENT DOCUMENTS

| | | |
|---|---|---|
| 5,743,477 A | 4/1998 | Walsh et al. |
| 5,824,864 A | 10/1998 | Fox et al. |
| 6,339,144 B1 * | 1/2002 | Cigan et al. ............ 530/435 |

FOREIGN PATENT DOCUMENTS

WO    WO 98/54327    12/1998

OTHER PUBLICATIONS

Dessen et al., Crystal Structure of Human Cytosolic Phospholipase $A_2$ Reveals a Novel Topology and Catalytic Mechanism, *Cell* 97:349–360 (1999).

* cited by examiner

*Primary Examiner*—Phuong T. Bui
*Assistant Examiner*—Cynthia Collins
(74) *Attorney, Agent, or Firm*—Timothy K. Ball; Dennis R. Hoerner, Jr.

(57) ABSTRACT

The present invention discloses DNA sequences encoding plant and novel lipid acyl hydrolase proteins having coleopteran specific insect inhibitory activity, as well as variants and permuteins having enhanced levels of activity directed to controlling coleotperan insect infestation and enhanced levels of expression in planta. Additionally, catalytic dyad active site conformation is disclosed for both dicot and monocot plant derived non-specific lipid acyl hydrolases having coleopteran insect inhibitory properties.

2 Claims, 13 Drawing Sheets

Figure 2:
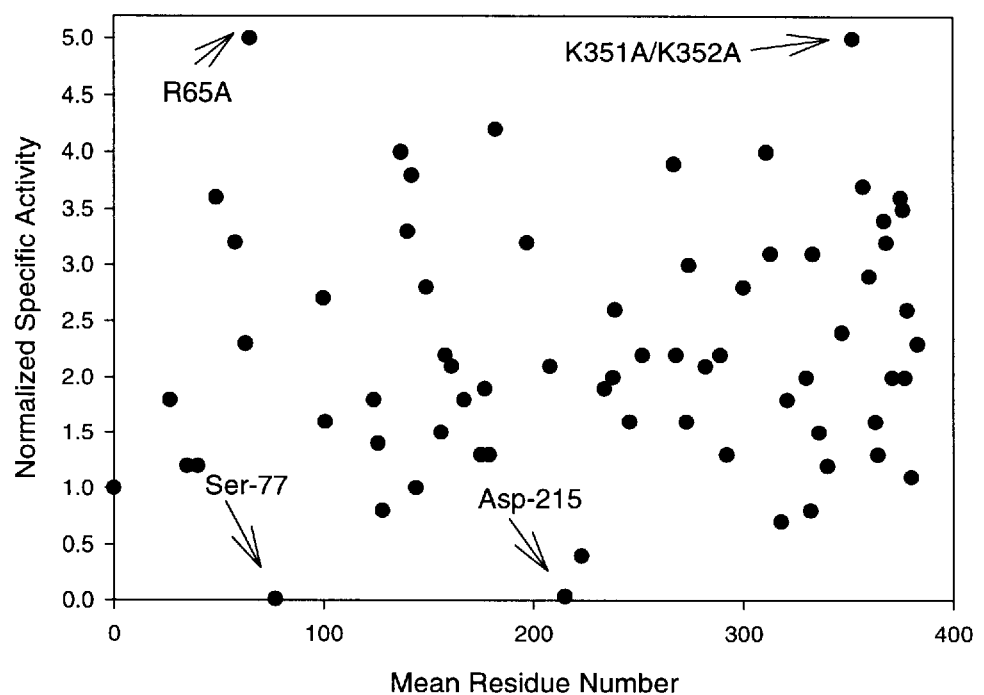

```
Pat17  atggcaactactaaatctttttaattttaatatttatgatattagcaactactagttca   60
        M  A  T  T  K  S  F  L  I  L  I  F  M  I  L  A  T  T  S  S   20

Pat17  acatttgctcagttggggagaaatggtgactgttcttagtattgatggaggtggaattaga  120
        T  F  A  Q  L  G  E  M  V  T  V  L  S  I  D  G  G  I  R   40

Pat17  gggatcattccggctaccattctcgaatttcttgaaggacaacttcaggaaatggacaat  180
        G  I  I  P  A  T  I  L  E  F  L  E  G  Q  L  Q  E  M  D  N   60

Pat17  aatgcagatgcaagacttgcagattactttgatgtaattggaggaacaagtacaggaggt  240
        N  A  D  A  R  L  A  D  Y  F  D  V  I  G  G  T  S  T  G  G   80

Pat17  ttattgactgctatgataagtactccaaatgaaaacaatcgaccctttgctgctgccaaa  300
        L  L  T  A  M  I  S  T  P  N  E  N  N  R  P  F  A  A  A  K  100

Pat17  gaaattgtacctttttacttcgaacatggccctcagatttttaatcctagtggtcaaatt  360
        E  I  V  P  F  Y  F  E  H  G  P  Q  I  F  N  P  S  G  Q  I  120

Pat17  ttaggcccaaaatatgatggaaaatatcttatgcaagttcttcaagaaaaacttggagaa  420
        L  G  P  K  Y  D  G  K  Y  L  M  Q  V  L  Q  E  K  L  G  E  140

Pat17  actcgtgtgcatcaagctttgacagaagttgtcatctcaagctttgacatcaaaacaaat  480
        T  R  V  H  Q  A  L  T  E  V  V  I  S  S  F  D  I  K  T  N  160

Pat17  aagccagtaatattcactaagtcaaatttagcaaactctccagaattggatgctaagatg  540
        K  P  V  I  F  T  K  S  N  L  A  N  S  P  E  L  D  A  K  M  180

Pat17  tatgacataagttattccacagcagcagctccaacatatttcctccgcattactttgtt  600
        Y  D  I  S  Y  S  T  A  A  A  P  T  Y  F  P  P  H  Y  F  V  200

Pat17  actaatactagtaatggagatgaatatgagttcaatcttgttgatggtgctgttgctact  660
        T  N  T  S  N  G  D  E  Y  E  F  N  L  V  D  G  A  V  A  T  220

Pat17  gttgctgatccggcgttattatccattagcgttgcaacgagacttgcacaaaaggatcca  720
        V  A  D  P  A  L  L  S  I  S  V  A  T  R  L  A  Q  K  D  P  240

Pat17  gcatttgcttcaattaggtcattgaattacaaaaaaatgctgttgctctcattaggcact  780
        A  F  A  S  I  R  S  L  N  Y  K  K  M  L  L  L  S  L  G  T  260

Pat17  ggcactacttcagagtttgataaaacatatacagcaaaagaggcagctacctggactgct  840
        G  T  T  S  E  F  D  K  T  Y  T  A  K  E  A  A  T  W  T  A  280

Pat17  gtacattggatgttagttatacagaaaatgactgatgcagcaagttcttacatgactgat  900
        V  H  W  M  L  V  I  Q  K  M  T  D  A  A  S  Y  M  T  D  300

Pat17  tattaccttctactgcttttcaagctcttgattcaaaaaacaattacctcagggttcaa  960
        Y  Y  L  S  T  A  F  Q  A  L  D  S  K  N  N  Y  L  R  V  Q  320

Pat17  gaaaatgcattaacaggcacaactactgaaatggatgatgcttctgaggctaatatggaa 1020
        E  N  A  L  T  G  T  T  T  E  M  D  D  A  S  E  A  N  M  E  340

Pat17  ttattagtacaagttggtgaaaacttattgaagaaaccagtttccgaagacaatcctgaa 1080
        L  L  V  Q  V  G  E  N  L  L  K  K  P  V  S  E  D  N  P  E  360

Pat17  acctatgaggaagctctaaagaggtttgcaaaattgctctctgataggaagaaactccga 1140
        T  Y  E  E  A  L  K  R  F  A  K  L  L  S  D  R  K  K  L  R  380

Pat17  gcaaacaaagcttcttattaa                                        1161
        A  N  K  A  S  Y  *                                         386
```

Figure 1

```
gi|patatin_mtc    ------------------------MATTKSFLILIFMILA-------TTSSTFAQLGEM  28
gi|PatFm          -------------------------------------------------------MALEEM  6
gi|PatIm          -------------------------------------------------------PWLEEM  6
gi|PatL+          ------------------------MATTKSFLILFFMILA-------TTSSTCAKLEEM  28
gi|PatA+          ------------------------MATTKSFLILFFMILA-------TTSSTCAKLEEM  28
gi|PatB+          ------------------------MATTKSVLVLFFMILA-------TTSSTCATLGEM  28
gi|pentin1_phb    -----------------------MKSKMAMLLLLFCVLSNQLVAAFSTQAKASKDGNL  35
gi|5c9_phb        ------------------------------------MGSIGRGTANCATVPQPPPSTGKL  24
gi|corn3_pep      ------------------------------------MGSIGRGTANCATVPQPPPSTGKL  24
gi|corn2_pep      ------------------------------------MGSIGRGTANCATVPQPPPSTGKL  24
gi|corn4_pep      ------------------------------------MGSIGRGTANCATVPQPPPSTGKL  24
gi|corn1_pep      RPTRPRHPRNTQKRGALLVGWILFSLAASPVKFQTHMGSIGRGTANCATVPQPPPSTGKL  60
gi|corn5_pep      ------------------------------------MGSIGRGTANCATVPQPPPSTGKL  24
                                                                               ::

gi|patatin_mtc    VTVLSIDGGGIRGIIPATILEFLEGQLQEMDNNADARLADYFDVIGGTSTGGLLTAMIST  88
gi|PatFm          VAVLSIDGGGIKGIIPGTILEFLEGQLQKMDNNADARLADYFDVIGGTSTGGLLTAMITT  66
gi|PatIm          VTVLSIDGGGIKGIIPAIILEFLEGQLQEVDNNKDARLADYFDVIGGTSTGGLLTAMITT  66
gi|PatL+          VTVLSIDGGGIKGIIPAIILEFLEGQLQEVDNNKDARLADYFDVIGGTSTGGLLTAMITT  88
gi|PatA+          VTVLSIDGGGIKGIIPAIILEFLEGQLQEVDNNKDARLADYFDVIGGTSTGGLLTAMITT  88
gi|PatB+          VTVLSIDGGGIKGIIPATILEFLEGQLQEVDNNKDARLADYFDVIGGTSTGGLLTAMITT  88
gi|pentin1_phb    VTVLAIDGGGIRGIIPGVILKQLEATLQRWDSS--ARLAEYFDVVAGTSTGGIITAILTA  93
gi|5c9_phb        ITILSIDGGGIRGLIPATIIAYLEAKLQELDGP-DARIADYFDVIAGTSTGALLASMLAA  83
gi|corn3_pep      ITILSIDGGGIRGLIPATIIAYLEAKLQELDGP-DARIADYFDVIAGTSTGALLASMLAA  83
gi|corn2_pep      ITILSIDGGGIRGLIPATIIAYLEAKLQELDGP-DARIADYFDVIAGTSTGALLASMLAA  83
gi|corn4_pep      ITILSIDGGGIRGLIPATIIAYLEAKLQELDGP-DARIADYFDVIAGTSTGALLASMLAA  83
gi|corn1_pep      ITILSIDGGGIRGLIPATIIAYLEAKLQELDGP-DARIADYFDVIAGTSTGALLASMLAA 119
gi|corn5_pep      ITILSIDGGGIRGLIPATIIAYLEAKLQELDGP-DARIADYFDVIAGTSTGALLASMLAA  83
                  :::*******:*:**. *: **. **. *.    **:*:****:.*****.:::::::

gi|patatin_mtc    PNENN--RPFAAAKEIVPFYFEHGPQIFNP------------SGQILGPKYDGKYLMQVL 134
gi|PatFm          PNENN--RPFAAANEIVPFYFEHGPHIFNSR-----------YWPIFWPKYDGKYLMQVL 113
gi|PatIm          PNENN--RPFAAAKDIVPFYFEHGPHIFNY------------SGSILGPMYDGKYLLQVL 112
gi|PatL+          PNENN--RPFAAAKDIVPFYFEHGPHIFNY------------SGSILGPMYDGKYLLQVL 134
gi|PatA+          PNENN--RPFAAAKDIVPFYFEHGPHIFNY------------SGSIIGPMYDGKYLLQVL 134
gi|PatB+          PNENN--RPFAAAKDIVPFYFEHGPHIFNS------------SGSIFGPMYDGKYFLQVL 134
gi|pentin1_phb    PDPQNKDRPLYAAEEIIDFYIEHGPSIFNKSTA-------CSLPGIFCPKYDGKYLQEII 146
gi|5c9_phb        PDENN--RPLFAAKDLTTFYLENGPKIFPQKKAGLLTPLRNLLGLVRGPKYDGVFLHDKI 141
gi|corn3_pep      PDENN--RPLFAAKDLTTFYLENGPKIFPQKKAGLLTPLRNLLGLVRGPKYDGVFLHDKI 141
gi|corn2_pep      PDENN--RPLFAAKDLTTFYLENGPKIFPQKKAGLLTPLRNLLGLVRGPKYDGVFLHDKI 141
gi|corn4_pep      PDENN--RPLFAAKDLTTFYLENGPKIFPQKKAGLLTPLRNLLGLVRGPKYDGVFLHDKI 141
gi|corn1_pep      PDENN--RPLFAAKDLTTFYLENGPKIFPQKKAGLLTPLRNLLGLVRGPKYDGVFLHDKI 177
gi|corn5_pep      PDENN--RPLFAAKDLTTFYLENGPKIFPQKKAGLLTPLRNLLGLVRGPKYDGVFLHDKI 141
                  *: :*  **: ***:::  **:*:** **              :  * *** :: : :
```

Figure 9 (a)

```
gi|patatin_mtc    QEKLGETRVHQALTEVVISSFDIKTNKPVIFTKSNLANSPELDAKMYDISYSTAAAPTYF 194
gi|PatFm          QEKLGETRVHQALTEVAISSFDIKTNKPVIFTKSNLAKSPELDAKTYDICYSTAAAPTYF 173
gi|PatIm          QEKLGETRVHQALTEVAISSFDIKTNKPVIFTKSNLAKSPELDAKMYDICYSTAAAPIYF 172
gi|PatL+          QEKLGETRVHQALTEVAISSFDIKTNKPVIFTKSNLAKSPELDAKMYDICYSTAAAPIYF 194
gi|PatA+          QEKLGETRVHQALTEVAISSFDIKTNKPVIFTKSNLAKSPELDAKMYDICYSTAAAPIYF 194
gi|PatB+          QEKLGETRVHQALTEVAISSFDIKTNKPVIFTKSNLAKSPELDAKMNDICYSTAAAPTYF 194
gi|pentin1_phb    SQKLNETLLDQTTTNVVIPSFDIKLLRPTIFSTFKLEEVPELNVKLSDVCMGTSAAPIVF 206
gi|5c9_phb        KSLTHDVRVADTVTNVIVPAFDVKYLQPIIFSTYEAKTDTLKNAHLSDICISTSAAPTYF 201
gi|corn3_pep      KSLTHDVRVADTVTNVIVPAFDVKYLQPIIFSTYEAKTDALKNAHLSDICISTSAAPTYF 201
gi|corn2_pep      KSLTHDVRVADTVTNVIVPAFDVKSLQPIIFSTYEAKTDTLKNAHLSDICISTSAAPTYF 201
gi|corn4_pep      KSLTHDVRVADTVTNVIVPAFDVKSLQPIIFSTYEAKTDTLKNAHLSDICISTSAAPTYF 201
gi|corn1_pep      KSLTHDVRVADTVTNVIVPAFDVKYLQPIIFSTYEAKTDALKNAHLSDICISTSAAPTYF 237
gi|corn5_pep      KSLTHDVRVADTVTNVIVPAFDVKYLQPIIFSTYEAKTDALKNAHLSDICISTSAAPTYF 201
                    :. : :: *:* :.:**:* :* **:. :    . .:  *:. .*:*** * gi|patatin_mtc    PPHYFVTNTSNG-DEYEFNLVDGAVATVADPALLSISVATRLAQKDPAFASIRSLNYKKM 253
gi|PatFm          PPHYFATNTING-DKYEFNLVDGAVATVADPALLSVSVATRRAQEDPAFASIRSLNYKKM 232
gi|PatIm          PPHHFVTHTSNG-ARYEFNLVDGAVATVGDPALLSLSVATRLAQEDPAFSSIKSLDYKQM 231
gi|PatL+          PPHHFVTHTSNG-ARYEFNLVDGAVATVGDPALLSLSVATRLAQEDPAFSSIKSLDYKQM 253
gi|PatA+          PPHYFITHTSNG-DIYEFNLVDGGVATVGDPALLSLSVATRLAQEDPAFSSIKSLDYKQM 253
gi|PatB+          PPHYFVTHTSNG-DKYEFNLVDGAVATVGDPALLSLSVRTKLAQVDPKFASIKSLNYNEM 253
gi|pentin1_phb    PPYYFKHG------DTEFNLVDGAIIADIPAPVALSEVLQQEKYKN--KE---------I 249
gi|5c9_phb        PAHFFKTEATDGRPPREYHLVDGGVAANNPTMVAMSMLTKEVHRRNPNFNAGSPTEYTNY 261
gi|corn3_pep      PAHFFKTEATDGRPPREYHLVDGGVAANNPTMVAMSMLTKEVHRRNPNFNAGSPTEYTNY 261
gi|corn2_pep      PAHFFKTEATDGRPPREYHLVDGGVAANNPTMVAMSMLTKEVHRRNPNFNAGSPTEYTNY 261
gi|corn4_pep      PAHFFKIEATDGRPPREYHLVDGGVAANNPTMVAMSMLTKEVHRRNPNFNAGSPTEYTNY 261
gi|corn1_pep      PAHFFKTEATDGRPPREYHLVDGGVAANNPTMVAMSMLTKEVHRRNPNFNAGSPTEYTNY 297
gi|corn5_pep      PAHFFKTEATDGRPPREYHLVDGGVAANNPTMVAMSMLTKEVHRRNPNFNAGSPTEYTNY 261
                  *.:.*          *::****.::  . :   : .    :

gi|patatin_mtc    LLLSLGTGTTSEFDKTYTAKEAATWTAVHWMLVIQK-----MTDAASSYMTDYYLSTAFQ 308
gi|PatFm          LLLSLGTGTTSEFDKTHTAEETAKWGALQWMLVIQQ-----MTEAASSYMTDYYLSTVFQ 287
gi|PatIm          LLLSLGTGTNSEFDKTYTAEEAAKWGPLRWMLAIQQ-----MTNAASFYMTDYYISTVFQ 286
gi|PatL+          LLLSLGTGTNSEFDKTYTAEEAAKWGPLRWMLAIQQ-----MTNAASSYMTDYYISTVFQ 308
gi|PatA+          LLLSLGTGTNSEFDKTYTAQEAAKWGPLRWMLAIQQ-----MTNAASSYMTDYYISTVFQ 308
gi|PatB+          LLLSLGTGTNSEFDKTYTAEEEAKWGPLRWILAIQQ-----MTNAASSYMTDYYLSTVFQ 308
gi|pentin1_phb    LLLSIGTGVVKPGEGYSANRTWTIFDWSSETLIG-------LMGHGTRAMSDYYVGSHFK 302
gi|5c9_phb        LIISVGTGSAKQAEK-YTAEQCAKWGLIQWLYNGGFTPIIDIFSHASSDMVDIHASILFQ 320
gi|corn3_pep      LIISVGTGSAKQAEK-YTAEQCAKWGLIQWLYNGGFTPIIDIFSHASSDMVDIHASILFQ 320
gi|corn2_pep      LIISVGTGSAKQAEK-YTAEQCAKWGLIQWLYNGGFTPIIDIFSHASSDMVDIHASILFQ 320
gi|corn4_pep      LIISVGTGSAKQAEK-YTAEQCAKWGLIQWLYNGGFTPIIDIFSHASSDMVDIHASILFQ 320
gi|corn1_pep      LIISVGTGSAKQAEK-YTAEQCAKWGLIQWLYNGGFTPIIDIFSHASSDMVDIHASILFQ 356
gi|corn5_pep      LIISVGTGSAKQAEK-YTAEQCAKWGLIQWLYNGGFTPIIDIFSHASSDMVDIHASILFQ 320
                  *::***   .  :  :.   : .::                 :  .: *  * :.  *:
```

Figure 9 (b)

```
gi|patatin_mtc    ALDSKNNYLRVQENALTGT----------------------TTEMDDASEANMELLVQ 344
gi|PatFm          DLHSQNNYLRVQENALTGT----------------------TTKADDASEANMELLAQ 323
gi|PatIm          ARHSQNNYLRVQENALNGT----------------------TTEMDDASEANMELLVQ 322
gi|PatL+          ARHSQNNYLRVQENALNGT----------------------TTEMDDASEANMELLVQ 344
gi|PatA+          ARHSQNNYLRVQENALTGT----------------------TTEMDDASEANMELLVQ 344
gi|PatB+          ARHSQNNYLRVQENALTGT----------------------TTEMDDASEANMELLVQ 344
gi|pentin1_phb    ALQPQNNYLRIQEYDLDPA----------------------LESIDDASTENMENLEK 338
gi|5c9_phb        ALHCEKKYLRIQDDTLTGN----------------------ASSVDIATKENMESLIS 356
gi|corn3_pep      ALHCEKKYLRIQDDTLTGN----------------------ASSVDIATKENMESLIS 356
gi|corn2_pep      ALHCEKKYLRIQDDTLTGN----------------------ASSVDIATKENMESLIS 356
gi|corn4_pep      ALHCEKKYLRIQDDTLTGN----------------------ASSVDIATKENMESLIS 356
gi|corn1_pep      ALHCEKKYLRIQLYYAGYFDWERIVRGHRHQGEHGVSDIDRPGAAQEASGESEHRHRAVR 416
gi|corn5_pep      ALHCEKKYLRIQLYYAG----------------------------------------- 337
                   . :::***:* gi|patatin_mtc    VGENLLKKPVSEDNP----------ETYEEALKRFAKLLSDRKKLRANKASY------- 386
gi|PatFm          VGENLLKKPVSKDNP----------ETYEEALKRFAKLLSDRKKLRANKASY------- 365
gi|PatIm          VGETLLKKPVSRDSP----------ETYEEALKRFAKLLSDRKKLRANKASY------- 364
gi|PatL+          VGATLLKKPVSKDSP----------ETYEEALKRFAKLLSDRKKLRANKASY------- 386
gi|PatA+          VGETLLKKPVSKDSP----------ETYEEALKRFAKLLSDRKKLRANKASY------- 386
gi|PatB+          VGEKLLKKPVSKDSP----------ETYEEALKRFAKLLSDRKKLRANKASY------- 386
gi|pentin1_phb    VGQSLLNEPVKRMNLNT-FVVEETGEGTNAEALDRLAQILYEEKITRGLGKISLEVDNID 397
gi|5c9_phb        IGQELLKKPVARVNIDTGVYESCDGEGTNAQSLADFAKQLSDERKLRKSNLNSN------ 410
gi|corn3_pep      IGQELLKKPVARVNIDTGLYESCDGEGTNAQSLADFAKQLSDERKLRKSNLNSN------ 410
gi|corn2_pep      IGQELLNKPVARVNIDTGLYESCEGEGTNAQSLADFAKQLSDERKLRKSNLNSN------ 410
gi|corn4_pep      IGQELLNKPVARVNIDTGLYESCEGEGTNAQSLADFAKQLSDERKLRKSNLNSN------ 410
gi|corn1_pep      VLRRGHKCTVASLRQATLRAQATQEQSQLQLINTSLSHSMCSFRRFTVSYFFNFNSVCVL 476
gi|corn5_pep      ------------------------------------------------------------ gi|patatin_mtc    --------------------------------
gi|PatFm          --------------------------------
gi|PatIm          --------------------------------
gi|PatL+          --------------------------------
gi|PatA+          --------------------------------
gi|PatB+          --------------------------------
gi|pentin1_phb    PYTERVRKLLF-------------------- 408
gi|5c9_phb        --------------------------------
gi|corn3_pep      --------------------------------
gi|corn2_pep      --------------------------------
gi|corn4_pep      --------------------------------
gi|corn1_pep      CVLCVYQTFKFNQKKKKKKKKKKKKKKKRAA 508
gi|corn5_pep      --------------------------------
```

Figure 9 (c)

SEQUENCE LISTING

<160> NUMBER OF SEQ ID NOS: 60

<210> SEQ ID NO 1
<211> LENGTH: 386
<212> TYPE: PRT
<213> ORGANISM: Solanum cardiophyllum
<220> FEATURE:
<221> NAME/KEY: Protein
<222> LOCATION: (1)..(386)
<223> OTHER INFORMATION: patatin homolog pat17 amino acid sequence

<400> SEQUENCE: 1

```
Met Ala Thr Thr Lys Ser Phe Leu Ile Leu Ile Phe Met Ile Leu Ala
1               5                   10                  15

Thr Thr Ser Ser Thr Phe Ala Gln Leu Gly Glu Met Val Thr Val Leu
                20                  25                  30

Ser Ile Asp Gly Gly Ile Arg Gly Ile Ile Pro Ala Thr Ile Leu
            35                  40                  45

Glu Phe Leu Glu Gly Gln Leu Gln Glu Met Asp Asn Asn Ala Asp Ala
        50                  55                  60

Arg Leu Ala Asp Tyr Phe Asp Val Ile Gly Gly Thr Ser Thr Gly Gly
65                  70                  75                  80

Leu Leu Thr Ala Met Ile Ser Thr Pro Asn Glu Asn Asn Arg Pro Phe
                85                  90                  95

Ala Ala Ala Lys Glu Ile Val Pro Phe Tyr Phe Glu His Gly Pro Gln
            100                 105                 110

Ile Phe Asn Pro Ser Gly Gln Ile Leu Gly Pro Lys Tyr Asp Gly Lys
        115                 120                 125

Tyr Leu Met Gln Val Leu Gln Glu Lys Leu Gly Glu Thr Arg Val His
    130                 135                 140

Gln Ala Leu Thr Glu Val Val Ile Ser Ser Phe Asp Ile Lys Thr Asn
145                 150                 155                 160

Lys Pro Val Ile Phe Thr Lys Ser Asn Leu Ala Asn Ser Pro Glu Leu
                165                 170                 175

Asp Ala Lys Met Tyr Asp Ile Ser Tyr Ser Thr Ala Ala Ala Pro Thr
            180                 185                 190

Tyr Phe Pro Pro His Tyr Phe Val Thr Asn Thr Ser Asn Gly Asp Glu
        195                 200                 205

Tyr Glu Phe Asn Leu Val Asp Gly Ala Val Ala Thr Val Ala Asp Pro
    210                 215                 220

Ala Leu Leu Ser Ile Ser Val Ala Thr Arg Leu Ala Gln Lys Asp Pro
225                 230                 235                 240

Ala Phe Ala Ser Ile Arg Ser Leu Asn Tyr Lys Lys Met Leu Leu Leu
                245                 250                 255
```

```
Ser Leu Gly Thr Gly Thr Thr Ser Glu Phe Asp Lys Thr Tyr Thr Ala
            260                 265                 270

Lys Glu Ala Ala Thr Trp Thr Ala Val His Trp Met Leu Val Ile Gln
        275                 280                 285

Lys Met Thr Asp Ala Ala Ser Ser Tyr Met Thr Asp Tyr Tyr Leu Ser
        290                 295                 300

Thr Ala Phe Gln Ala Leu Asp Ser Lys Asn Asn Tyr Leu Arg Val Gln
305                 310                 315                 320

Glu Asn Ala Leu Thr Gly Thr Thr Glu Met Asp Asp Ala Ser Glu
                325                 330                 335

Ala Asn Met Glu Leu Leu Val Gln Val Gly Glu Asn Leu Leu Lys Lys
        340                 345                 350

Pro Val Ser Glu Asp Asn Pro Glu Thr Tyr Glu Glu Ala Leu Lys Arg
        355                 360                 365

Phe Ala Lys Leu Leu Ser Asp Arg Lys Lys Leu Arg Ala Asn Lys Ala
        370                 375                 380

Ser Tyr
385

<210> SEQ ID NO 2
<211> LENGTH: 365
<212> TYPE: PRT
<213> ORGANISM: synthetic
<220> FEATURE:
<221> NAME/KEY: Protein
<222> LOCATION: (1)..(365)
<223> OTHER INFORMATION: Patatin isozyme PatFm (mature protein lacking
      signal peptide)

<400> SEQUENCE: 2

Met Ala Leu Glu Glu Met Val Ala Val Leu Ser Ile Asp Gly Gly Gly
1               5                   10                  15

Ile Lys Gly Ile Ile Pro Gly Thr Ile Leu Glu Phe Leu Glu Gly Gln
            20                  25                  30

Leu Gln Lys Met Asp Asn Asn Ala Asp Ala Arg Leu Ala Asp Tyr Phe
        35                  40                  45

Asp Val Ile Gly Gly Thr Ser Thr Gly Gly Leu Leu Thr Ala Met Ile
    50                  55                  60

Thr Thr Pro Asn Glu Asn Asn Arg Pro Phe Ala Ala Ala Asn Glu Ile
65                  70                  75                  80

Val Pro Phe Tyr Phe Glu His Gly Pro His Ile Phe Asn Ser Arg Tyr
                85                  90                  95

Trp Pro Ile Phe Trp Pro Lys Tyr Asp Gly Lys Tyr Leu Met Gln Val
            100                 105                 110

Leu Gln Glu Lys Leu Gly Glu Thr Arg Val His Gln Ala Leu Thr Glu
        115                 120                 125

Val Ala Ile Ser Ser Phe Asp Ile Lys Thr Asn Lys Pro Val Ile Phe
    130                 135                 140

Thr Lys Ser Asn Leu Ala Lys Ser Pro Glu Leu Asp Ala Lys Thr Tyr
145                 150                 155                 160

Asp Ile Cys Tyr Ser Thr Ala Ala Ala Pro Thr Tyr Phe Pro Pro His
                165                 170                 175

Tyr Phe Ala Thr Asn Thr Ile Asn Gly Asp Lys Tyr Glu Phe Asn Leu
            180                 185                 190

Val Asp Gly Ala Val Ala Thr Val Ala Asp Pro Ala Leu Leu Ser Val
        195                 200                 205
```

```
Ser Val Ala Thr Arg Arg Ala Gln Glu Asp Pro Ala Phe Ala Ser Ile
    210                 215                 220

Arg Ser Leu Asn Tyr Lys Lys Met Leu Leu Ser Leu Gly Thr Gly
225                 230                 235                 240

Thr Thr Ser Glu Phe Asp Lys Thr His Thr Ala Glu Glu Thr Ala Lys
                245                 250                 255

Trp Gly Ala Leu Gln Trp Met Leu Val Ile Gln Gln Met Thr Glu Ala
                260                 265                 270

Ala Ser Ser Tyr Met Thr Asp Tyr Tyr Leu Ser Thr Val Phe Gln Asp
                275                 280                 285

Leu His Ser Gln Asn Asn Tyr Leu Arg Val Gln Glu Asn Ala Leu Thr
    290                 295                 300

Gly Thr Thr Thr Lys Ala Asp Asp Ala Ser Glu Ala Asn Met Glu Leu
305                 310                 315                 320

Leu Ala Gln Val Gly Glu Asn Leu Leu Lys Lys Pro Val Ser Lys Asp
                325                 330                 335

Asn Pro Glu Thr Tyr Glu Glu Ala Leu Lys Arg Phe Ala Lys Leu Leu
                340                 345                 350

Ser Asp Arg Lys Lys Leu Arg Ala Asn Lys Ala Ser Tyr
                355                 360                 365

<210> SEQ ID NO 3
<211> LENGTH: 364
<212> TYPE: PRT
<213> ORGANISM: synthetic
<220> FEATURE:
<221> NAME/KEY: Protein
<222> LOCATION: (1)..(364)
<223> OTHER INFORMATION: Patatin isozyme PatIm (mature protein lacking
      signal peptide)

<400> SEQUENCE: 3

Pro Trp Leu Glu Glu Met Val Thr Val Leu Ser Ile Asp Gly Gly Gly
1               5                   10                  15

Ile Lys Gly Ile Ile Pro Ala Ile Ile Leu Glu Phe Leu Glu Gly Gln
                20                  25                  30

Leu Gln Glu Val Asp Asn Asn Lys Asp Ala Arg Leu Ala Asp Tyr Phe
            35                  40                  45

Asp Val Ile Gly Gly Thr Ser Thr Gly Gly Leu Leu Thr Ala Met Ile
        50                  55                  60

Thr Thr Pro Asn Glu Asn Asn Arg Pro Phe Ala Ala Ala Lys Asp Ile
65                  70                  75                  80

Val Pro Phe Tyr Phe Glu His Gly Pro His Ile Phe Asn Tyr Ser Gly
                85                  90                  95

Ser Ile Leu Gly Pro Met Tyr Asp Gly Lys Tyr Leu Leu Gln Val Leu
            100                 105                 110

Gln Glu Lys Leu Gly Glu Thr Arg Val His Gln Ala Leu Thr Glu Val
        115                 120                 125

Ala Ile Ser Ser Phe Asp Ile Lys Thr Asn Lys Pro Val Ile Phe Thr
    130                 135                 140

Lys Ser Asn Leu Ala Lys Ser Pro Glu Leu Asp Ala Lys Met Tyr Asp
145                 150                 155                 160

Ile Cys Tyr Ser Thr Ala Ala Ala Pro Ile Tyr Phe Pro Pro His His
                165                 170                 175

Phe Val Thr His Thr Ser Asn Gly Ala Arg Tyr Glu Phe Asn Leu Val
            180                 185                 190
```

-continued

```
Asp Gly Ala Val Ala Thr Val Gly Asp Pro Ala Leu Leu Ser Leu Ser
            195                 200                 205

Val Ala Thr Arg Leu Ala Gln Glu Asp Pro Ala Phe Ser Ser Ile Lys
    210                 215                 220

Ser Leu Asp Tyr Lys Gln Met Leu Leu Ser Leu Gly Thr Gly Thr
225                 230                 235                 240

Asn Ser Glu Phe Asp Lys Thr Tyr Thr Ala Glu Ala Ala Lys Trp
                245                 250                 255

Gly Pro Leu Arg Trp Met Leu Ala Ile Gln Gln Met Thr Asn Ala Ala
                260                 265                 270

Ser Phe Tyr Met Thr Asp Tyr Tyr Ile Ser Thr Val Phe Gln Ala Arg
            275                 280                 285

His Ser Gln Asn Asn Tyr Leu Arg Val Gln Glu Asn Ala Leu Asn Gly
        290                 295                 300

Thr Thr Thr Glu Met Asp Asp Ala Ser Glu Ala Asn Met Glu Leu Leu
305                 310                 315                 320

Val Gln Val Gly Glu Thr Leu Leu Lys Lys Pro Val Ser Arg Asp Ser
                325                 330                 335

Pro Glu Thr Tyr Glu Glu Ala Leu Lys Arg Phe Ala Lys Leu Leu Ser
                340                 345                 350

Asp Arg Lys Lys Leu Arg Ala Asn Lys Ala Ser Tyr
            355                 360

<210> SEQ ID NO 4
<211> LENGTH: 386
<212> TYPE: PRT
<213> ORGANISM: synthetic
<220> FEATURE:
<221> NAME/KEY: Protein
<222> LOCATION: (1)..(386)
<223> OTHER INFORMATION: Patatin isozyme PatL+ (including signal
      peptide)

<400> SEQUENCE: 4

Met Ala Thr Thr Lys Ser Phe Leu Ile Leu Phe Phe Met Ile Leu Ala
1               5                   10                  15

Thr Thr Ser Ser Thr Cys Ala Lys Leu Glu Glu Met Val Thr Val Leu
                20                  25                  30

Ser Ile Asp Gly Gly Gly Ile Lys Gly Ile Ile Pro Ala Ile Ile Leu
            35                  40                  45

Glu Phe Leu Glu Gly Gln Leu Gln Glu Val Asp Asn Asn Lys Asp Ala
        50                  55                  60

Arg Leu Ala Asp Tyr Phe Asp Val Ile Gly Gly Thr Ser Thr Gly Gly
65                  70                  75                  80

Leu Leu Thr Ala Met Ile Thr Thr Pro Asn Glu Asn Asn Arg Pro Phe
                85                  90                  95

Ala Ala Ala Lys Asp Ile Val Pro Phe Tyr Phe Glu His Gly Pro His
            100                 105                 110

Ile Phe Asn Tyr Ser Gly Ser Ile Leu Gly Pro Met Tyr Asp Gly Lys
        115                 120                 125

Tyr Leu Leu Gln Val Leu Gln Glu Lys Leu Gly Glu Thr Arg Val His
    130                 135                 140

Gln Ala Leu Thr Glu Val Ala Ile Ser Ser Phe Asp Ile Lys Thr Asn
145                 150                 155                 160

Lys Pro Val Ile Phe Thr Lys Ser Asn Leu Ala Lys Ser Pro Glu Leu
                165                 170                 175
```

```
Asp Ala Lys Met Tyr Asp Ile Cys Tyr Ser Thr Ala Ala Pro Ile
            180                 185                 190

Tyr Phe Pro Pro His His Phe Val Thr His Thr Ser Asn Gly Ala Arg
            195                 200                 205

Tyr Glu Phe Asn Leu Val Asp Gly Ala Val Ala Thr Val Gly Asp Pro
            210                 215                 220

Ala Leu Leu Ser Leu Ser Val Ala Thr Arg Leu Ala Gln Glu Asp Pro
225                 230                 235                 240

Ala Phe Ser Ser Ile Lys Ser Leu Asp Tyr Lys Gln Met Leu Leu Leu
            245                 250                 255

Ser Leu Gly Thr Gly Thr Asn Ser Glu Phe Asp Lys Thr Tyr Thr Ala
            260                 265                 270

Glu Glu Ala Ala Lys Trp Gly Pro Leu Arg Trp Met Leu Ala Ile Gln
            275                 280                 285

Gln Met Thr Asn Ala Ala Ser Ser Tyr Met Thr Asp Tyr Tyr Ile Ser
            290                 295                 300

Thr Val Phe Gln Ala Arg His Ser Gln Asn Asn Tyr Leu Arg Val Gln
305                 310                 315                 320

Glu Asn Ala Leu Asn Gly Thr Thr Thr Glu Met Asp Asp Ala Ser Glu
            325                 330                 335

Ala Asn Met Glu Leu Leu Val Gln Val Gly Ala Thr Leu Leu Lys Lys
            340                 345                 350

Pro Val Ser Lys Asp Ser Pro Glu Thr Tyr Glu Glu Ala Leu Lys Arg
            355                 360                 365

Phe Ala Lys Leu Leu Ser Asp Arg Lys Lys Leu Arg Ala Asn Lys Ala
            370                 375                 380

Ser Tyr
385

<210> SEQ ID NO 5
<211> LENGTH: 386
<212> TYPE: PRT
<213> ORGANISM: synthetic
<220> FEATURE:
<221> NAME/KEY: Protein
<222> LOCATION: (1)..(386)
<223> OTHER INFORMATION: Patatin isozyme PatA+ (including signal
      peptide)

<400> SEQUENCE: 5

Met Ala Thr Thr Lys Ser Phe Leu Ile Leu Phe Phe Met Ile Leu Ala
1               5                   10                  15

Thr Thr Ser Ser Thr Cys Ala Lys Leu Glu Glu Met Val Thr Val Leu
            20                  25                  30

Ser Ile Asp Gly Gly Gly Ile Lys Gly Ile Ile Pro Ala Ile Ile Leu
            35                  40                  45

Glu Phe Leu Glu Gly Gln Leu Gln Glu Val Asp Asn Asn Lys Asp Ala
50                  55                  60

Arg Leu Ala Asp Tyr Phe Asp Val Ile Gly Gly Thr Ser Thr Gly Gly
65                  70                  75                  80

Leu Leu Thr Ala Met Ile Thr Thr Pro Asn Glu Asn Asn Arg Pro Phe
            85                  90                  95

Ala Ala Ala Lys Asp Ile Val Pro Phe Tyr Phe Glu His Gly Pro His
            100                 105                 110

Ile Phe Asn Tyr Ser Gly Ser Ile Gly Pro Met Tyr Asp Gly Lys
            115                 120                 125
```

-continued

```
Tyr Leu Leu Gln Val Leu Gln Glu Lys Leu Gly Glu Thr Arg Val His
    130                 135                 140

Gln Ala Leu Thr Glu Val Ala Ile Ser Ser Phe Asp Ile Lys Thr Asn
145                 150                 155                 160

Lys Pro Val Ile Phe Thr Lys Ser Asn Leu Ala Lys Ser Pro Glu Leu
                165                 170                 175

Asp Ala Lys Met Tyr Asp Ile Cys Tyr Ser Thr Ala Ala Pro Ile
                180                 185                 190

Tyr Phe Pro Pro His Tyr Phe Ile Thr His Thr Ser Asn Gly Asp Ile
            195                 200                 205

Tyr Glu Phe Asn Leu Val Asp Gly Val Ala Thr Val Gly Asp Pro
    210                 215                 220

Ala Leu Leu Ser Leu Ser Val Ala Thr Arg Leu Ala Gln Glu Asp Pro
225                 230                 235                 240

Ala Phe Ser Ser Ile Lys Ser Leu Asp Tyr Lys Gln Met Leu Leu Leu
                245                 250                 255

Ser Leu Gly Thr Gly Thr Asn Ser Glu Phe Asp Lys Thr Tyr Thr Ala
                260                 265                 270

Gln Glu Ala Ala Lys Trp Gly Pro Leu Arg Trp Met Leu Ala Ile Gln
    275                 280                 285

Gln Met Thr Asn Ala Ala Ser Ser Tyr Met Thr Asp Tyr Tyr Ile Ser
    290                 295                 300

Thr Val Phe Gln Ala Arg His Ser Gln Asn Asn Tyr Leu Arg Val Gln
305                 310                 315                 320

Glu Asn Ala Leu Thr Gly Thr Thr Thr Glu Met Asp Asp Ala Ser Glu
                325                 330                 335

Ala Asn Met Glu Leu Leu Val Gln Val Gly Glu Thr Leu Leu Lys Lys
                340                 345                 350

Pro Val Ser Lys Asp Ser Pro Glu Thr Tyr Glu Glu Ala Leu Lys Arg
                355                 360                 365

Phe Ala Lys Leu Leu Ser Asp Arg Lys Lys Leu Arg Ala Asn Lys Ala
    370                 375                 380

Ser Tyr
385

<210> SEQ ID NO 6
<211> LENGTH: 386
<212> TYPE: PRT
<213> ORGANISM: synthetic
<220> FEATURE:
<221> NAME/KEY: Protein
<222> LOCATION: (1)..(386)
<223> OTHER INFORMATION: Patatin isozyme PatB+ (including signal
      peptide)

<400> SEQUENCE: 6

Met Ala Thr Thr Lys Ser Val Leu Val Leu Phe Phe Met Ile Leu Ala
1               5                   10                  15

Thr Thr Ser Ser Thr Cys Ala Thr Leu Gly Glu Met Val Thr Val Leu
                20                  25                  30

Ser Ile Asp Gly Gly Gly Ile Lys Gly Ile Ile Pro Ala Thr Ile Leu
                35                  40                  45

Glu Phe Leu Glu Gly Gln Leu Gln Glu Val Asp Asn Asn Lys Asp Ala
    50                  55                  60

Arg Leu Ala Asp Tyr Phe Asp Val Ile Gly Gly Thr Ser Thr Gly Gly
65                  70                  75                  80
```

-continued

```
Leu Leu Thr Ala Met Ile Thr Pro Asn Glu Asn Arg Pro Phe
            85                  90                  95

Ala Ala Ala Lys Asp Ile Val Pro Phe Tyr Phe Glu His Gly Pro His
            100                 105                 110

Ile Phe Asn Ser Ser Gly Ser Ile Phe Gly Pro Met Tyr Asp Gly Lys
            115                 120                 125

Tyr Phe Leu Gln Val Leu Gln Glu Lys Leu Gly Glu Thr Arg Val His
            130                 135                 140

Gln Ala Leu Thr Glu Val Ala Ile Ser Ser Phe Asp Ile Lys Thr Asn
145                 150                 155                 160

Lys Pro Val Ile Phe Thr Lys Ser Asn Leu Ala Lys Ser Pro Glu Leu
            165                 170                 175

Asp Ala Lys Met Asn Asp Ile Cys Tyr Ser Thr Ala Ala Pro Thr
            180                 185                 190

Tyr Phe Pro Pro His Tyr Phe Val Thr His Thr Ser Asn Gly Asp Lys
            195                 200                 205

Tyr Glu Phe Asn Leu Val Asp Gly Ala Val Ala Thr Val Gly Asp Pro
            210                 215                 220

Ala Leu Leu Ser Leu Ser Val Arg Thr Lys Leu Ala Gln Val Asp Pro
225                 230                 235                 240

Lys Phe Ala Ser Ile Lys Ser Leu Asn Tyr Asn Glu Met Leu Leu Leu
            245                 250                 255

Ser Leu Gly Thr Gly Thr Asn Ser Glu Phe Asp Lys Thr Tyr Thr Ala
            260                 265                 270

Glu Glu Ala Ala Lys Trp Gly Pro Leu Arg Trp Ile Leu Ala Ile Gln
            275                 280                 285

Gln Met Thr Asn Ala Ala Ser Ser Tyr Met Thr Asp Tyr Tyr Leu Ser
            290                 295                 300

Thr Val Phe Gln Ala Arg His Ser Gln Asn Asn Tyr Leu Arg Val Gln
305                 310                 315                 320

Glu Asn Ala Leu Thr Gly Thr Thr Glu Met Asp Asp Ala Ser Glu
            325                 330                 335

Ala Asn Met Glu Leu Leu Val Gln Val Gly Glu Lys Leu Leu Lys Lys
            340                 345                 350

Pro Val Ser Lys Asp Ser Pro Glu Thr Tyr Glu Glu Ala Leu Lys Arg
            355                 360                 365

Phe Ala Lys Leu Leu Ser Asp Arg Lys Lys Leu Arg Ala Asn Lys Ala
            370                 375                 380

Ser Tyr
385
```

<210> SEQ ID NO 7
<211> LENGTH: 408
<212> TYPE: PRT
<213> ORGANISM: Pentaclethra macroloba
<220> FEATURE:
<221> NAME/KEY: Protein
<222> LOCATION: (1)..(408)
<223> OTHER INFORMATION: patatin homolog pentin 1

<400> SEQUENCE: 7

```
Met Lys Ser Lys Met Ala Met Leu Leu Leu Phe Cys Val Leu Ser
1               5                   10                  15

Asn Gln Leu Val Ala Ala Phe Ser Thr Gln Ala Lys Ala Ser Lys Asp
            20                  25                  30
```

```
Gly Asn Leu Val Thr Val Leu Ala Ile Asp Gly Gly Ile Arg Gly
         35                  40                  45

Ile Ile Pro Gly Val Ile Leu Lys Gln Leu Glu Ala Thr Leu Gln Arg
 50                  55                  60

Trp Asp Ser Ser Ala Arg Leu Ala Glu Tyr Phe Asp Val Val Ala Gly
 65                  70                  75                  80

Thr Ser Thr Gly Gly Ile Ile Thr Ala Ile Leu Thr Ala Pro Asp Pro
                 85                  90                  95

Gln Asn Lys Asp Arg Pro Leu Tyr Ala Ala Glu Glu Ile Ile Asp Phe
                100                 105                 110

Tyr Ile Glu His Gly Pro Ser Ile Phe Asn Lys Ser Thr Ala Cys Ser
                115                 120                 125

Leu Pro Gly Ile Phe Cys Pro Lys Tyr Asp Gly Lys Tyr Leu Gln Glu
            130                 135                 140

Ile Ile Ser Gln Lys Leu Asn Glu Thr Leu Leu Asp Gln Thr Thr Thr
145                 150                 155                 160

Asn Val Val Ile Pro Ser Phe Asp Ile Lys Leu Leu Arg Pro Thr Ile
                165                 170                 175

Phe Ser Thr Phe Lys Leu Glu Glu Val Pro Glu Leu Asn Val Lys Leu
                180                 185                 190

Ser Asp Val Cys Met Gly Thr Ser Ala Ala Pro Ile Val Phe Pro Pro
            195                 200                 205

Tyr Tyr Phe Lys His Gly Asp Thr Glu Phe Asn Leu Val Asp Gly Ala
        210                 215                 220

Ile Ile Ala Asp Ile Pro Ala Pro Val Ala Leu Ser Glu Val Leu Gln
225                 230                 235                 240

Gln Glu Lys Tyr Lys Asn Lys Glu Ile Leu Leu Leu Ser Ile Gly Thr
                245                 250                 255

Gly Val Val Lys Pro Gly Glu Gly Tyr Ser Ala Asn Arg Thr Trp Thr
            260                 265                 270

Ile Phe Asp Trp Ser Ser Glu Thr Leu Ile Gly Leu Met Gly His Gly
        275                 280                 285

Thr Arg Ala Met Ser Asp Tyr Tyr Val Gly Ser His Phe Lys Ala Leu
    290                 295                 300

Gln Pro Gln Asn Asn Tyr Leu Arg Ile Gln Glu Tyr Asp Leu Asp Pro
305                 310                 315                 320

Ala Leu Glu Ser Ile Asp Asp Ala Ser Thr Glu Asn Met Glu Asn Leu
                325                 330                 335

Glu Lys Val Gly Gln Ser Leu Leu Asn Glu Pro Val Lys Arg Met Asn
            340                 345                 350

Leu Asn Thr Phe Val Val Glu Glu Thr Gly Glu Gly Thr Asn Ala Glu
        355                 360                 365

Ala Leu Asp Arg Leu Ala Gln Ile Leu Tyr Glu Glu Lys Ile Thr Arg
    370                 375                 380

Gly Leu Gly Lys Ile Ser Leu Glu Val Asp Asn Ile Asp Pro Tyr Thr
385                 390                 395                 400

Glu Arg Val Arg Lys Leu Leu Phe
                405

<210> SEQ ID NO 8
<211> LENGTH: 410
<212> TYPE: PRT
<213> ORGANISM: Zea mays
<220> FEATURE:
<221> NAME/KEY: Protein
```

```
<222> LOCATION: (1)..(410)
<223> OTHER INFORMATION: monocot patatin homolog 5c9

<400> SEQUENCE: 8

Met Gly Ser Ile Gly Arg Gly Thr Ala Asn Cys Ala Thr Val Pro Gln
1               5                   10                  15

Pro Pro Pro Ser Thr Gly Lys Leu Ile Thr Ile Leu Ser Ile Asp Gly
            20                  25                  30

Gly Gly Ile Arg Gly Leu Ile Pro Ala Thr Ile Ile Ala Tyr Leu Glu
        35                  40                  45

Ala Lys Leu Gln Glu Leu Asp Gly Pro Asp Ala Arg Ile Ala Asp Tyr
50                  55                  60

Phe Asp Val Ile Ala Gly Thr Ser Thr Gly Ala Leu Leu Ala Ser Met
65                  70                  75                  80

Leu Ala Ala Pro Asp Glu Asn Asn Arg Pro Leu Phe Ala Ala Lys Asp
                85                  90                  95

Leu Thr Thr Phe Tyr Leu Glu Asn Gly Pro Lys Ile Phe Pro Gln Lys
            100                 105                 110

Lys Ala Gly Leu Leu Thr Pro Leu Arg Asn Leu Leu Gly Leu Val Arg
        115                 120                 125

Gly Pro Lys Tyr Asp Gly Val Phe Leu His Asp Lys Ile Lys Ser Leu
130                 135                 140

Thr His Asp Val Arg Val Ala Asp Thr Val Thr Asn Val Ile Val Pro
145                 150                 155                 160

Ala Phe Asp Val Lys Tyr Leu Gln Pro Ile Ile Phe Ser Thr Tyr Glu
                165                 170                 175

Ala Lys Thr Asp Thr Leu Lys Asn Ala His Leu Ser Asp Ile Cys Ile
            180                 185                 190

Ser Thr Ser Ala Ala Pro Thr Tyr Phe Pro Ala His Phe Phe Lys Thr
        195                 200                 205

Glu Ala Thr Asp Gly Arg Pro Pro Arg Glu Tyr His Leu Val Asp Gly
210                 215                 220

Gly Val Ala Ala Asn Asn Pro Thr Met Val Ala Met Ser Met Leu Thr
225                 230                 235                 240

Lys Glu Val His Arg Arg Asn Pro Asn Phe Asn Ala Gly Ser Pro Thr
                245                 250                 255

Glu Tyr Thr Asn Tyr Leu Ile Ile Ser Val Gly Thr Gly Ser Ala Lys
            260                 265                 270

Gln Ala Glu Lys Tyr Thr Ala Glu Gln Cys Ala Lys Trp Gly Leu Ile
        275                 280                 285

Gln Trp Leu Tyr Asn Gly Gly Phe Thr Pro Ile Ile Asp Ile Phe Ser
290                 295                 300

His Ala Ser Ser Asp Met Val Asp Ile His Ala Ser Ile Leu Phe Gln
305                 310                 315                 320

Ala Leu His Cys Glu Lys Lys Tyr Leu Arg Ile Gln Asp Asp Thr Leu
                325                 330                 335

Thr Gly Asn Ala Ser Ser Val Asp Ile Ala Thr Lys Glu Asn Met Glu
            340                 345                 350

Ser Leu Ile Ser Ile Gly Gln Glu Leu Leu Lys Lys Pro Val Ala Arg
        355                 360                 365

Val Asn Ile Asp Thr Gly Val Tyr Glu Ser Cys Asp Gly Glu Gly Thr
370                 375                 380

Asn Ala Gln Ser Leu Ala Asp Phe Ala Lys Gln Leu Ser Asp Glu Arg
385                 390                 395                 400
```

Lys Leu Arg Lys Ser Asn Leu Asn Ser Asn
            405                 410

<210> SEQ ID NO 9
<211> LENGTH: 508
<212> TYPE: PRT
<213> ORGANISM: synthetic
<220> FEATURE:
<221> NAME/KEY: Protein
<222> LOCATION: (1)..(508)
<223> OTHER INFORMATION: maize patatin homolog amino acid sequence
      corn 1

<400> SEQUENCE: 9

Arg Pro Thr Arg Pro Arg His Pro Arg Asn Thr Gln Lys Arg Gly Ala
1               5                   10                  15

Leu Leu Val Gly Trp Ile Leu Phe Ser Leu Ala Ala Ser Pro Val Lys
            20                  25                  30

Phe Gln Thr His Met Gly Ser Ile Gly Arg Gly Thr Ala Asn Cys Ala
        35                  40                  45

Thr Val Pro Gln Pro Pro Ser Thr Gly Lys Leu Ile Thr Ile Leu
 50                  55                  60

Ser Ile Asp Gly Gly Ile Arg Gly Leu Ile Pro Ala Thr Ile Ile
65                  70                  75                  80

Ala Tyr Leu Glu Ala Lys Leu Gln Glu Leu Asp Gly Pro Asp Ala Arg
                85                  90                  95

Ile Ala Asp Tyr Phe Asp Val Ile Ala Gly Thr Ser Thr Gly Ala Leu
            100                 105                 110

Leu Ala Ser Met Leu Ala Ala Pro Asp Glu Asn Asn Arg Pro Leu Phe
        115                 120                 125

Ala Ala Lys Asp Leu Thr Thr Phe Tyr Leu Glu Asn Gly Pro Lys Ile
130                 135                 140

Phe Pro Gln Lys Lys Ala Gly Leu Leu Thr Pro Leu Arg Asn Leu Leu
145                 150                 155                 160

Gly Leu Val Arg Gly Pro Lys Tyr Asp Gly Val Phe Leu His Asp Lys
                165                 170                 175

Ile Lys Ser Leu Thr His Asp Val Arg Val Ala Asp Thr Val Thr Asn
            180                 185                 190

Val Ile Val Pro Ala Phe Asp Val Lys Tyr Leu Gln Pro Ile Ile Phe
        195                 200                 205

Ser Thr Tyr Glu Ala Lys Thr Asp Ala Leu Lys Asn Ala His Leu Ser
210                 215                 220

Asp Ile Cys Ile Ser Thr Ser Ala Ala Pro Thr Tyr Phe Pro Ala His
225                 230                 235                 240

Phe Phe Lys Thr Glu Ala Thr Asp Gly Arg Pro Pro Arg Glu Tyr His
                245                 250                 255

Leu Val Asp Gly Gly Val Ala Ala Asn Asn Pro Thr Met Val Ala Met
            260                 265                 270

Ser Met Leu Thr Lys Glu Val His Arg Arg Asn Pro Asn Phe Asn Ala
        275                 280                 285

Gly Ser Pro Thr Glu Tyr Thr Asn Tyr Leu Ile Ile Ser Val Gly Thr
290                 295                 300

Gly Ser Ala Lys Gln Ala Glu Lys Tyr Thr Ala Glu Gln Cys Ala Lys
305                 310                 315                 320

Trp Gly Leu Ile Gln Trp Leu Tyr Asn Gly Gly Phe Thr Pro Ile Ile
                325                 330                 335

```
Asp Ile Phe Ser His Ala Ser Ser Asp Met Val Asp Ile His Ala Ser
            340                 345                 350

Ile Leu Phe Gln Ala Leu His Cys Glu Lys Lys Tyr Leu Arg Ile Gln
            355                 360                 365

Leu Tyr Tyr Ala Gly Tyr Phe Asp Trp Glu Arg Ile Val Arg Gly His
            370                 375                 380

Arg His Gln Gly Glu His Gly Val Ser Asp Ile Asp Arg Pro Gly Ala
385                 390                 395                 400

Ala Gln Glu Ala Ser Gly Glu Ser Glu His Arg His Arg Ala Val Arg
            405                 410                 415

Val Leu Arg Arg Gly His Lys Cys Thr Val Ala Ser Leu Arg Gln Ala
            420                 425                 430

Thr Leu Arg Ala Gln Ala Thr Gln Glu Gln Ser Gln Leu Gln Leu Ile
            435                 440                 445

Asn Thr Ser Leu Ser His Ser Met Cys Ser Phe Arg Arg Phe Thr Val
            450                 455                 460

Ser Tyr Phe Phe Asn Phe Asn Ser Val Cys Val Leu Cys Val Leu Cys
465                 470                 475                 480

Val Tyr Gln Thr Phe Lys Phe Asn Gln Lys Lys Lys Lys Lys Lys Lys
            485                 490                 495

Lys Lys Lys Lys Lys Lys Lys Lys Arg Ala Ala
            500                 505

<210> SEQ ID NO 10
<211> LENGTH: 410
<212> TYPE: PRT
<213> ORGANISM: synthetic
<220> FEATURE:
<221> NAME/KEY: Protein
<222> LOCATION: (1)..(410)
<223> OTHER INFORMATION: maize patatin homolog amino acid sequence
      corn 2

<400> SEQUENCE: 10

Met Gly Ser Ile Gly Arg Gly Thr Ala Asn Cys Ala Thr Val Pro Gln
1               5                   10                  15

Pro Pro Ser Thr Gly Lys Leu Ile Thr Ile Leu Ser Ile Asp Gly
            20                  25                  30

Gly Gly Ile Arg Gly Leu Ile Pro Ala Thr Ile Ala Tyr Leu Glu
            35                  40                  45

Ala Lys Leu Gln Glu Leu Asp Gly Pro Asp Ala Arg Ile Ala Asp Tyr
    50                  55                  60

Phe Asp Val Ile Ala Gly Thr Ser Thr Gly Ala Leu Leu Ala Ser Met
65                  70                  75                  80

Leu Ala Ala Pro Asp Glu Asn Asn Arg Pro Leu Phe Ala Ala Lys Asp
                85                  90                  95

Leu Thr Thr Phe Tyr Leu Glu Asn Gly Pro Lys Ile Phe Pro Gln Lys
            100                 105                 110

Lys Ala Gly Leu Leu Thr Pro Leu Arg Asn Leu Leu Gly Leu Val Arg
            115                 120                 125

Gly Pro Lys Tyr Asp Gly Val Phe Leu His Asp Lys Ile Lys Ser Leu
    130                 135                 140

Thr His Asp Val Arg Val Ala Asp Thr Val Thr Asn Val Ile Val Pro
145                 150                 155                 160

Ala Phe Asp Val Lys Ser Leu Gln Pro Ile Ile Phe Ser Thr Tyr Glu
                165                 170                 175
```

```
Ala Lys Thr Asp Thr Leu Lys Asn Ala His Leu Ser Asp Ile Cys Ile
            180                 185                 190

Ser Thr Ser Ala Ala Pro Thr Tyr Phe Pro Ala His Phe Phe Lys Thr
            195                 200                 205

Glu Ala Thr Asp Gly Arg Pro Pro Arg Glu Tyr His Leu Val Asp Gly
            210                 215                 220

Gly Val Ala Ala Asn Asn Pro Thr Met Val Ala Met Ser Met Leu Thr
225                 230                 235                 240

Lys Glu Val His Arg Arg Asn Pro Asn Phe Asn Ala Gly Ser Pro Thr
            245                 250                 255

Glu Tyr Thr Asn Tyr Leu Ile Ile Ser Val Gly Thr Gly Ser Ala Lys
            260                 265                 270

Gln Ala Glu Lys Tyr Thr Ala Glu Gln Cys Ala Lys Trp Gly Leu Ile
            275                 280                 285

Gln Trp Leu Tyr Asn Gly Gly Phe Thr Pro Ile Ile Asp Ile Phe Ser
            290                 295                 300

His Ala Ser Ser Asp Met Val Asp Ile His Ala Ser Ile Leu Phe Gln
305                 310                 315                 320

Ala Leu His Cys Glu Lys Lys Tyr Leu Arg Ile Gln Asp Asp Thr Leu
            325                 330                 335

Thr Gly Asn Ala Ser Ser Val Asp Ile Ala Thr Lys Glu Asn Met Glu
            340                 345                 350

Ser Leu Ile Ser Ile Gly Gln Glu Leu Leu Asn Lys Pro Val Ala Arg
            355                 360                 365

Val Asn Ile Asp Thr Gly Leu Tyr Glu Ser Cys Glu Gly Glu Gly Thr
            370                 375                 380

Asn Ala Gln Ser Leu Ala Asp Phe Ala Lys Gln Leu Ser Asp Glu Arg
385                 390                 395                 400

Lys Leu Arg Lys Ser Asn Leu Asn Ser Asn
            405                 410

<210> SEQ ID NO 11
<211> LENGTH: 410
<212> TYPE: PRT
<213> ORGANISM: synthetic
<220> FEATURE:
<221> NAME/KEY: Protein
<222> LOCATION: (1)..(410)
<223> OTHER INFORMATION: maize patatin homolog amino acid sequence
      corn 3

<400> SEQUENCE: 11

Met Gly Ser Ile Gly Arg Gly Thr Ala Asn Cys Ala Thr Val Pro Gln
1               5                   10                  15

Pro Pro Pro Ser Thr Gly Lys Leu Ile Thr Ile Leu Ser Ile Asp Gly
            20                  25                  30

Gly Gly Ile Arg Gly Leu Ile Pro Ala Thr Ile Ala Tyr Leu Glu
            35                  40                  45

Ala Lys Leu Gln Glu Leu Asp Gly Pro Asp Ala Arg Ile Ala Asp Tyr
        50                  55                  60

Phe Asp Val Ile Ala Gly Thr Ser Thr Gly Ala Leu Leu Ala Ser Met
65                  70                  75                  80

Leu Ala Ala Pro Asp Glu Asn Asn Arg Pro Leu Phe Ala Ala Lys Asp
            85                  90                  95

Leu Thr Thr Phe Tyr Leu Glu Asn Gly Pro Lys Ile Phe Pro Gln Lys
            100                 105                 110
```

-continued

```
Lys Ala Gly Leu Leu Thr Pro Leu Arg Asn Leu Leu Gly Leu Val Arg
        115                 120                 125

Gly Pro Lys Tyr Asp Gly Val Phe Leu His Asp Lys Ile Lys Ser Leu
    130                 135                 140

Thr His Asp Val Arg Val Ala Asp Thr Val Thr Asn Val Ile Val Pro
145                 150                 155                 160

Ala Phe Asp Val Lys Tyr Leu Gln Pro Ile Ile Phe Ser Thr Tyr Glu
                165                 170                 175

Ala Lys Thr Asp Ala Leu Lys Asn Ala His Leu Ser Asp Ile Cys Ile
            180                 185                 190

Ser Thr Ser Ala Ala Pro Thr Tyr Phe Pro Ala His Phe Phe Lys Thr
        195                 200                 205

Glu Ala Thr Asp Gly Arg Pro Pro Arg Glu Tyr His Leu Val Asp Gly
    210                 215                 220

Gly Val Ala Ala Asn Asn Pro Thr Met Val Ala Met Ser Met Leu Thr
225                 230                 235                 240

Lys Glu Val His Arg Arg Asn Pro Asn Phe Asn Ala Gly Ser Pro Thr
                245                 250                 255

Glu Tyr Thr Asn Tyr Leu Ile Ile Ser Val Gly Thr Gly Ser Ala Lys
            260                 265                 270

Gln Ala Glu Lys Tyr Thr Ala Glu Gln Cys Ala Lys Trp Gly Leu Ile
        275                 280                 285

Gln Trp Leu Tyr Asn Gly Gly Phe Thr Pro Ile Ile Asp Ile Phe Ser
    290                 295                 300

His Ala Ser Ser Asp Met Val Asp Ile His Ala Ser Ile Leu Phe Gln
305                 310                 315                 320

Ala Leu His Cys Glu Lys Lys Tyr Leu Arg Ile Gln Asp Asp Thr Leu
                325                 330                 335

Thr Gly Asn Ala Ser Ser Val Asp Ile Ala Thr Lys Glu Asn Met Glu
            340                 345                 350

Ser Leu Ile Ser Ile Gly Gln Glu Leu Leu Lys Lys Pro Val Ala Arg
        355                 360                 365

Val Asn Ile Asp Thr Gly Leu Tyr Glu Ser Cys Asp Gly Glu Gly Thr
    370                 375                 380

Asn Ala Gln Ser Leu Ala Asp Phe Ala Lys Gln Leu Ser Asp Glu Arg
385                 390                 395                 400

Lys Leu Arg Lys Ser Asn Leu Asn Ser Asn
                405                 410

<210> SEQ ID NO 12
<211> LENGTH: 410
<212> TYPE: PRT
<213> ORGANISM: synthetic
<220> FEATURE:
<221> NAME/KEY: Protein
<222> LOCATION: (1)..(410)
<223> OTHER INFORMATION: maize patatin homolog amino acid sequence
      corn 4

<400> SEQUENCE: 12

Met Gly Ser Ile Gly Arg Gly Thr Ala Asn Cys Ala Thr Val Pro Gln
1               5                   10                  15

Pro Pro Ser Thr Gly Lys Leu Ile Thr Ile Leu Ser Ile Asp Gly
                20                  25                  30

Gly Gly Ile Arg Gly Leu Ile Pro Ala Thr Ile Ile Ala Tyr Leu Glu
            35                  40                  45
```

Ala Lys Leu Gln Glu Leu Asp Gly Pro Asp Ala Arg Ile Ala Asp Tyr
            50                  55                  60

Phe Asp Val Ile Ala Gly Thr Ser Thr Gly Ala Leu Leu Ala Ser Met
 65                  70                  75                  80

Leu Ala Ala Pro Asp Glu Asn Asn Arg Pro Leu Phe Ala Ala Lys Asp
                 85                  90                  95

Leu Thr Thr Phe Tyr Leu Glu Asn Gly Pro Lys Ile Phe Pro Gln Lys
                100                 105                 110

Lys Ala Gly Leu Leu Thr Pro Leu Arg Asn Leu Leu Gly Leu Val Arg
            115                 120                 125

Gly Pro Lys Tyr Asp Gly Val Phe Leu His Asp Lys Ile Lys Ser Leu
130                 135                 140

Thr His Asp Val Arg Val Ala Asp Thr Val Thr Asn Val Ile Val Pro
145                 150                 155                 160

Ala Phe Asp Val Lys Ser Leu Gln Pro Ile Ile Phe Ser Thr Tyr Glu
                165                 170                 175

Ala Lys Thr Asp Thr Leu Lys Asn Ala His Leu Ser Asp Ile Cys Ile
            180                 185                 190

Ser Thr Ser Ala Ala Pro Thr Tyr Phe Pro Ala His Phe Phe Lys Ile
        195                 200                 205

Glu Ala Thr Asp Gly Arg Pro Pro Arg Glu Tyr His Leu Val Asp Gly
210                 215                 220

Gly Val Ala Ala Asn Asn Pro Thr Met Val Ala Met Ser Met Leu Thr
225                 230                 235                 240

Lys Glu Val His Arg Arg Asn Pro Asn Phe Asn Ala Gly Ser Pro Thr
                245                 250                 255

Glu Tyr Thr Asn Tyr Leu Ile Ile Ser Val Gly Thr Gly Ser Ala Lys
            260                 265                 270

Gln Ala Glu Lys Tyr Thr Ala Glu Gln Cys Ala Lys Trp Gly Leu Ile
        275                 280                 285

Gln Trp Leu Tyr Asn Gly Gly Phe Thr Pro Ile Ile Asp Ile Phe Ser
290                 295                 300

His Ala Ser Ser Asp Met Val Asp Ile His Ala Ser Ile Leu Phe Gln
305                 310                 315                 320

Ala Leu His Cys Glu Lys Lys Tyr Leu Arg Ile Gln Asp Asp Thr Leu
                325                 330                 335

Thr Gly Asn Ala Ser Ser Val Asp Ile Ala Thr Lys Glu Asn Met Glu
            340                 345                 350

Ser Leu Ile Ser Ile Gly Gln Glu Leu Leu Asn Lys Pro Val Ala Arg
        355                 360                 365

Val Asn Ile Asp Thr Gly Leu Tyr Glu Ser Cys Glu Gly Glu Gly Thr
370                 375                 380

Asn Ala Gln Ser Leu Ala Asp Phe Ala Lys Gln Leu Ser Asp Glu Arg
385                 390                 395                 400

Lys Leu Arg Lys Ser Asn Leu Asn Ser Asn
            405                 410

<210> SEQ ID NO 13
<211> LENGTH: 337
<212> TYPE: PRT
<213> ORGANISM: synthetic
<220> FEATURE:
<221> NAME/KEY: Protein
<222> LOCATION: (1)..(337)
<223> OTHER INFORMATION: maize patatin homolog amino acid sequence corn 5

<400> SEQUENCE: 13

```
Met Gly Ser Ile Gly Arg Gly Thr Ala Asn Cys Ala Thr Val Pro Gln
1               5                   10                  15

Pro Pro Pro Ser Thr Gly Lys Leu Ile Thr Ile Leu Ser Ile Asp Gly
            20                  25                  30

Gly Gly Ile Arg Gly Leu Ile Pro Ala Thr Ile Ala Tyr Leu Glu
        35                  40                  45

Ala Lys Leu Gln Glu Leu Asp Gly Pro Asp Ala Arg Ile Ala Asp Tyr
    50                  55                  60

Phe Asp Val Ile Ala Gly Thr Ser Thr Gly Ala Leu Leu Ala Ser Met
65                  70                  75                  80

Leu Ala Ala Pro Asp Glu Asn Asn Arg Pro Leu Phe Ala Ala Lys Asp
                85                  90                  95

Leu Thr Thr Phe Tyr Leu Glu Asn Gly Pro Lys Ile Phe Pro Gln Lys
            100                 105                 110

Lys Ala Gly Leu Leu Thr Pro Leu Arg Asn Leu Leu Gly Leu Val Arg
        115                 120                 125

Gly Pro Lys Tyr Asp Gly Val Phe Leu His Asp Lys Ile Lys Ser Leu
    130                 135                 140

Thr His Asp Val Arg Val Ala Asp Thr Val Thr Asn Val Ile Val Pro
145                 150                 155                 160

Ala Phe Asp Val Lys Tyr Leu Gln Pro Ile Ile Phe Ser Thr Tyr Glu
                165                 170                 175

Ala Lys Thr Asp Ala Leu Lys Asn Ala His Leu Ser Asp Ile Cys Ile
            180                 185                 190

Ser Thr Ser Ala Ala Pro Thr Tyr Phe Pro Ala His Phe Phe Lys Thr
        195                 200                 205

Glu Ala Thr Asp Gly Arg Pro Pro Arg Glu Tyr His Leu Val Asp Gly
    210                 215                 220

Gly Val Ala Ala Asn Asn Pro Thr Met Val Ala Met Ser Met Leu Thr
225                 230                 235                 240

Lys Glu Val His Arg Arg Asn Pro Asn Phe Asn Ala Gly Ser Pro Thr
                245                 250                 255

Glu Tyr Thr Asn Tyr Leu Ile Ile Ser Val Gly Thr Gly Ser Ala Lys
            260                 265                 270

Gln Ala Glu Lys Tyr Thr Ala Glu Gln Cys Ala Lys Trp Gly Leu Ile
        275                 280                 285

Gln Trp Leu Tyr Asn Gly Gly Phe Thr Pro Ile Ile Asp Ile Phe Ser
    290                 295                 300

His Ala Ser Ser Asp Met Val Asp Ile His Ala Ser Ile Leu Phe Gln
305                 310                 315                 320

Ala Leu His Cys Glu Lys Lys Tyr Leu Arg Ile Gln Leu Tyr Tyr Ala
                325                 330                 335

Gly
```

<210> SEQ ID NO 14
<211> LENGTH: 5
<212> TYPE: PRT
<213> ORGANISM: synthetic
<220> FEATURE:
<221> NAME/KEY: Protein
<222> LOCATION: (1)..(5)

<223> OTHER INFORMATION: Xaa = Ser or Thr.

<400> SEQUENCE: 14

Gly Xaa Ser Xaa Gly
1               5

<210> SEQ ID NO 15
<211> LENGTH: 7
<212> TYPE: PRT
<213> ORGANISM: synthetic
<220> FEATURE:
<221> NAME/KEY: Protein
<222> LOCATION: (1)..(7)
<223> OTHER INFORMATION: Xaa2 = Aromatics such as Phe, Tyr, Trp.
      Xaa3 = Arg or His.

<400> SEQUENCE: 15

Glu Xaa Xaa Leu Val Asp Gly
1               5

<210> SEQ ID NO 16
<211> LENGTH: 3
<212> TYPE: PRT
<213> ORGANISM: synthetic
<220> FEATURE:
<221> NAME/KEY: Protein
<222> LOCATION: (1)..(3)
<223> OTHER INFORMATION: Linker Sequence

<400> SEQUENCE: 16

Gly Pro Gly
1

<210> SEQ ID NO 17
<211> LENGTH: 7
<212> TYPE: PRT
<213> ORGANISM: synthetic
<220> FEATURE:
<221> NAME/KEY: Protein
<222> LOCATION: (1)..(7)
<223> OTHER INFORMATION: Linker Sequence 2

<400> SEQUENCE: 17

Gly Gly Gly Ser Gly Gly Gly
1               5

<210> SEQ ID NO 18
<211> LENGTH: 33
<212> TYPE: DNA
<213> ORGANISM: synthetic
<220> FEATURE:
<221> NAME/KEY: DNA
<222> LOCATION: (1)..(33)
<223> OTHER INFORMATION: oligonucleotide-1

<400> SEQUENCE: 18
gttagatctc accatggcaa ctactaaatc ttt                             33

<210> SEQ ID NO 19
<211> LENGTH: 33
<212> TYPE: DNA
<213> ORGANISM: synthetic
<220> FEATURE:
<221> NAME/KEY: DNA
<222> LOCATION: (1)..(33)
<223> OTHER INFORMATION: oligonucleotide-2

<400> SEQUENCE: 19

-continued

```
ccagaattct cattaataag aagctttgtt tgc                                    33
```

<210> SEQ ID NO 20
<211> LENGTH: 1128
<212> TYPE: DNA
<213> ORGANISM: synthetic
<220> FEATURE:
<221> NAME/KEY: DNA
<222> LOCATION: (1)..(1128)
<223> OTHER INFORMATION: pMON37402 sequence encoding permutein protein

<400> SEQUENCE: 20

```
tcgagaaaag agaggctgaa gcttcattga attacaaaaa aatgctgttg ctctcattag      60
gcactggcac tacttcagag tttgataaaa catatacagc aaaagaggca gctacctgga     120
ctgctgtaca ttggatgtta gttatacaga aaatgactga tgcagcaagt tcttacatga     180
ctgattatta cctttctact gcttttcaag ctcttgattc aaaaaacaat tacctcaggg     240
ttcaagaaaa tgcattaaca ggcacaacta ctgaaatgga tgatgcttct gaggctaata     300
tggaattatt agtacaagtt ggtgaaaact tattgaagaa accagtttcc gaagacaatc     360
ctgaaaccta tgaggaagct ctaaagaggt ttgcaaaatt gctctctgat aggaagaaac     420
tccgagcaaa caaagcttct tatggaccag gacagttggg agaaatggtg actgttctta     480
gtattgatgg aggtggaatt agagggatca ttccggctac cattctcgaa tttcttgaag     540
gacaacttca ggaaatggac aataatgcag atgcaagact tgcagattac tttgatgtaa     600
ttggaggaac aagtacagga ggtttattga ctgctatgat aagtactcca aatgaaaaca     660
atcgacccct tgctgctgcc aaagaaattg taccttttta cttcgaacat ggccctcaga     720
ttttaatcc tagtggtcaa atttttaggcc caaaatatga tggaaaatat cttatgcaag     780
ttcttcaaga aaaacttgga gaaactcgtg tgcatcaagc tttgacagaa gttgtcatct     840
caagctttga catcaaaaca aataagccag taatattcac taagtcaaat ttagcaaact     900
ctccagaatt ggatgctaag atgtatgaca taagttattc cacagcagca gctccaacat     960
attttcctcc gcattacttt gttactaata ctagtaatgg agatgaatat gagttcaatc    1020
ttgttgatgg tgctgttgct actgttgctg atccggcgtt attatccatt agcgttgcaa    1080
cgagacttgc acaaaaggat ccagcatttg cttcaattag gtaatgag                 1128
```

<210> SEQ ID NO 21
<211> LENGTH: 366
<212> TYPE: PRT
<213> ORGANISM: synthetic
<220> FEATURE:
<221> NAME/KEY: Protein
<222> LOCATION: (1)..(366)
<223> OTHER INFORMATION: Permutein protein encoded from pMON37402
      sequence

<400> SEQUENCE: 21

```
Ser Leu Asn Tyr Lys Lys Met Leu Leu Leu Ser Leu Gly Thr Gly Thr
1               5                   10                  15

Thr Ser Glu Phe Asp Lys Thr Tyr Thr Ala Lys Glu Ala Ala Thr Trp
            20                  25                  30

Thr Ala Val His Trp Met Leu Val Ile Gln Lys Met Thr Asp Ala Ala
        35                  40                  45

Ser Ser Tyr Met Thr Asp Tyr Tyr Leu Ser Thr Ala Phe Gln Ala Leu
    50                  55                  60

Asp Ser Lys Asn Asn Tyr Leu Arg Val Gln Glu Asn Ala Leu Thr Gly
65                  70                  75                  80
```

```
Thr Thr Thr Glu Met Asp Asp Ala Ser Glu Ala Asn Met Glu Leu Leu
             85                  90                  95

Val Gln Val Gly Glu Asn Leu Leu Lys Lys Pro Val Ser Glu Asp Asn
        100                 105                 110

Pro Glu Thr Tyr Glu Glu Ala Leu Lys Arg Phe Ala Lys Leu Leu Ser
        115                 120                 125

Asp Arg Lys Lys Leu Arg Ala Asn Lys Ala Ser Tyr Gly Pro Gly Gln
    130                 135                 140

Leu Gly Glu Met Val Thr Val Leu Ser Ile Asp Gly Gly Ile Arg
145                 150                 155                 160

Gly Ile Ile Pro Ala Thr Ile Leu Glu Phe Leu Glu Gly Gln Leu Gln
                165                 170                 175

Glu Met Asp Asn Asn Ala Asp Ala Arg Leu Ala Asp Tyr Phe Asp Val
            180                 185                 190

Ile Gly Gly Thr Ser Thr Gly Gly Leu Leu Thr Ala Met Ile Ser Thr
        195                 200                 205

Pro Asn Glu Asn Asn Arg Pro Phe Ala Ala Lys Glu Ile Val Pro
    210                 215                 220

Phe Tyr Phe Glu His Gly Pro Gln Ile Phe Asn Pro Ser Gly Gln Ile
225                 230                 235                 240

Leu Gly Pro Lys Tyr Asp Gly Lys Tyr Leu Met Gln Val Leu Gln Glu
                245                 250                 255

Lys Leu Gly Glu Thr Arg Val His Gln Ala Leu Thr Glu Val Val Ile
                260                 265                 270

Ser Ser Phe Asp Ile Lys Thr Asn Lys Pro Val Ile Phe Thr Lys Ser
        275                 280                 285

Asn Leu Ala Asn Ser Pro Glu Leu Asp Ala Lys Met Tyr Asp Ile Ser
    290                 295                 300

Tyr Ser Thr Ala Ala Ala Pro Thr Tyr Phe Pro Pro His Tyr Phe Val
305                 310                 315                 320

Thr Asn Thr Ser Asn Gly Asp Glu Tyr Glu Phe Asn Leu Val Asp Gly
                325                 330                 335

Ala Val Ala Thr Val Ala Asp Pro Ala Leu Leu Ser Ile Ser Val Ala
            340                 345                 350

Thr Arg Leu Ala Gln Lys Asp Pro Ala Phe Ala Ser Ile Arg
        355                 360                 365

<210> SEQ ID NO 22
<211> LENGTH: 1128
<212> TYPE: DNA
<213> ORGANISM: synthetic
<220> FEATURE:
<221> NAME/KEY: DNA
<222> LOCATION: (1)..(1128)
<223> OTHER INFORMATION: pMON37405 sequence encoding permutein protein

<400> SEQUENCE: 22
tcgagaaaag agaggctgaa gctaatacta gtaatggaga tgaatatgag ttcaatcttg      60
ttgatggtgc tgttgctact gttgctgatc ggcgttatt atccattagc gttgcaacga     120
gacttgcaca aaaggatcca gcatttgctt caattaggtc attgaattac aaaaaaatgc    180
tgttgctctc attaggcact ggcactactt cagagtttga taaacatat acagcaaaag    240 aggcagctac ctggactgct gtacattgga tgttagttat acagaaaatg actgatgcag    300
caagttctta catgactgat tattaccttt ctactgcttt tcaagctctt gattcaaaaa    360
```

-continued

```
acaattacct cagggttcaa gaaaatgcat taacaggcac aactactgaa atggatgatg      420
cttctgaggc taatatggaa ttattagtac aagttggtga aaacttattg aagaaaccag      480
tttccgaaga caatcctgaa acctatgagg aagctctaaa gaggtttgca aaattgctct      540
ctgataggaa gaaactccga gcaaacaaag cttcttatgg accaggacag ttgggagaaa      600
tggtgactgt tcttagtatt gatggaggtg gaattagagg gatcattccg gctaccattc      660
tcgaatttct tgaaggacaa cttcaggaaa tggacaataa tgcagatgca agacttgcag      720
attactttga tgtaattgga ggaacaagta caggaggttt attgactgct atgataagta      780
ctccaaatga aacaatcga cccttgctg ctgccaaaga aattgtacct ttttacttcg        840
aacatggccc tcagattttt aatcctagtg gtcaaatttt aggcccaaaa tatgatggaa      900
aatatcttat gcaagttctt caagaaaaac ttggagaaac tcgtgtgcat caagctttga      960
cagaagttgt catctcaagc tttgacatca aaacaaataa gccagtaata ttcactaagt     1020
caaatttagc aaactctcca gaattggatg ctaagatgta tgacataagt tattccacag     1080
cagcagctcc aacatatttt cctccgcatt actttgttac ttaatgag                  1128
```

<210> SEQ ID NO 23
<211> LENGTH: 366
<212> TYPE: PRT
<213> ORGANISM: synthetic
<220> FEATURE:
<221> NAME/KEY: Protein
<222> LOCATION: (1)..(366)
<223> OTHER INFORMATION: Permutein protein encoded by pMON37405 sequence

<400> SEQUENCE: 23

```
Asn Thr Ser Asn Gly Asp Glu Tyr Glu Phe Asn Leu Val Asp Gly Ala
1               5                   10                  15

Val Ala Thr Val Ala Asp Pro Ala Leu Leu Ser Ile Ser Val Ala Thr
            20                  25                  30

Arg Leu Ala Gln Lys Asp Pro Ala Phe Ala Ser Ile Arg Ser Leu Asn
        35                  40                  45

Tyr Lys Lys Met Leu Leu Leu Ser Leu Gly Thr Gly Thr Thr Ser Glu
    50                  55                  60

Phe Asp Lys Thr Tyr Thr Ala Lys Glu Ala Ala Thr Trp Thr Ala Val
65                  70                  75                  80

His Trp Met Leu Val Ile Gln Lys Met Thr Asp Ala Ala Ser Ser Tyr
                85                  90                  95

Met Thr Asp Tyr Tyr Leu Ser Thr Ala Phe Gln Ala Leu Asp Ser Lys
            100                 105                 110

Asn Asn Tyr Leu Arg Val Gln Glu Asn Ala Leu Thr Gly Thr Thr Thr
        115                 120                 125

Glu Met Asp Asp Ala Ser Glu Ala Asn Met Glu Leu Leu Val Gln Val
    130                 135                 140

Gly Glu Asn Leu Leu Lys Lys Pro Val Ser Glu Asp Asn Pro Glu Thr
145                 150                 155                 160

Tyr Glu Glu Ala Leu Lys Arg Phe Ala Lys Leu Leu Ser Asp Arg Lys
                165                 170                 175

Lys Leu Arg Ala Asn Lys Ala Ser Tyr Gly Pro Gly Gln Leu Gly Glu
            180                 185                 190

Met Val Thr Val Leu Ser Ile Asp Gly Gly Gly Ile Arg Gly Ile Ile
        195                 200                 205

Pro Ala Thr Ile Leu Glu Phe Leu Glu Gly Gln Leu Gln Glu Met Asp
    210                 215                 220
```

```
Asn Asn Ala Asp Ala Arg Leu Ala Asp Tyr Phe Asp Val Ile Gly Gly
225                 230                 235                 240

Thr Ser Thr Gly Gly Leu Leu Thr Ala Met Ile Ser Thr Pro Asn Glu
            245                 250                 255

Asn Asn Arg Pro Phe Ala Ala Lys Glu Ile Val Pro Phe Tyr Phe
        260                 265                 270

Glu His Gly Pro Gln Ile Phe Asn Pro Ser Gly Gln Ile Leu Gly Pro
        275                 280                 285

Lys Tyr Asp Gly Lys Tyr Leu Met Gln Val Leu Gln Glu Lys Leu Gly
290                 295                 300

Glu Thr Arg Val His Gln Ala Leu Thr Glu Val Ile Ser Ser Phe
305                 310                 315                 320

Asp Ile Lys Thr Asn Lys Pro Val Ile Phe Thr Lys Ser Asn Leu Ala
            325                 330                 335

Asn Ser Pro Glu Leu Asp Ala Lys Met Tyr Asp Ile Ser Tyr Ser Thr
            340                 345                 350

Ala Ala Ala Pro Thr Tyr Phe Pro Pro His Tyr Phe Val Thr
            355                 360                 365

<210> SEQ ID NO 24
<211> LENGTH: 1128
<212> TYPE: DNA
<213> ORGANISM: synthetic
<220> FEATURE:
<221> NAME/KEY: DNA
<222> LOCATION: (1)..(1128)
<223> OTHER INFORMATION: pMON37406 sequence encoding permutein protein

<400> SEQUENCE: 24
tcgagaaaag agaggctgaa gctagttatt ccacagcagc agctccaaca tattttcctc     60
cgcattactt tgttactaat actagtaatg gagatgaata tgagttcaat cttgttgatg    120
gtgctgttgc tactgttgct gatccggcgt tattatccat tagcgttgca acgagacttg    180
cacaaaagga tccagcattt gcttcaatta ggtcattgaa ttacaaaaaa atgctgttgc    240
tctcattagg cactggcact acttcagagt ttgataaaac atatacagca aaagaggcag    300
ctacctggac tgctgtacat tggatgttag ttatacagaa aatgactgat gcagcaagtt    360
cttacatgac tgattattac cttctactg cttttcaagc tcttgattca aaaaacaatt    420
acctcagggt tcaagaaaat gcattaacag gcacaactac tgaaatggat gatgcttctg    480
aggctaatat ggaattatta gtacaagttg gtgaaaactt attgaagaaa ccagtttccg    540
aagacaatcc tgaaacctat gaggaagctc taaagaggtt tgcaaaattg ctctctgata    600
ggaagaaact ccgagcaaac aaagcttctt atggaccagg acagttggga gaaatggtga    660
ctgttcttag tattgatgga ggtggaatta gagggatcat tccggctacc attctcgaat    720
ttcttgaagg acaacttcag gaaatggaca ataatgcaga tgcaagactt gcagattact    780
ttgatgtaat tggaggaaca agtacaggag gtttattgac tgctatgata agtactccaa    840
atgaaaacaa tcgaccctt gctgctgcca agaaattgt accttttac ttcgaacatg    900
gccctcagat ttttaatcct agtggtcaaa tttaggccc aaaatatgat ggaaaatatc    960
ttatgcaagt tcttcaagaa aaacttggag aaactcgtgt gcatcaagct ttgacagaag   1020
ttgtcatctc aagctttgac atcaaaacaa ataagccagt aatattcact aagtcaaatt   1080
tagcaaactc tccagaattg gatgctaaga tgtatgacat ataatgag                1128
```

```
<210> SEQ ID NO 25
<211> LENGTH: 366
<212> TYPE: PRT
<213> ORGANISM: synthetic
<220> FEATURE:
<221> NAME/KEY: Protein
<222> LOCATION: (1)..(366)
<223> OTHER INFORMATION: Permutein protein encoded by pMON37406

<400> SEQUENCE: 25

Ser Tyr Ser Thr Ala Ala Pro Thr Tyr Phe Pro His Tyr Phe
  1               5                  10                  15

Val Thr Asn Thr Ser Asn Gly Asp Glu Tyr Glu Phe Asn Leu Val Asp
                 20                  25                  30

Gly Ala Val Ala Thr Val Ala Asp Pro Ala Leu Leu Ser Ile Ser Val
             35                  40                  45

Ala Thr Arg Leu Ala Gln Lys Asp Pro Ala Phe Ala Ser Ile Arg Ser
         50                  55                  60

Leu Asn Tyr Lys Lys Met Leu Leu Ser Leu Gly Thr Gly Thr Thr
 65                  70                  75                  80

Ser Glu Phe Asp Lys Thr Tyr Thr Ala Lys Glu Ala Ala Thr Trp Thr
                 85                  90                  95

Ala Val His Trp Met Leu Val Ile Gln Lys Met Thr Asp Ala Ala Ser
            100                 105                 110

Ser Tyr Met Thr Asp Tyr Tyr Leu Ser Thr Ala Phe Gln Ala Leu Asp
            115                 120                 125

Ser Lys Asn Asn Tyr Leu Arg Val Gln Glu Asn Ala Leu Thr Gly Thr
        130                 135                 140

Thr Thr Glu Met Asp Asp Ala Ser Glu Ala Asn Met Glu Leu Leu Val
145                 150                 155                 160

Gln Val Gly Glu Asn Leu Leu Lys Lys Pro Val Ser Glu Asp Asn Pro
                165                 170                 175

Glu Thr Tyr Glu Glu Ala Leu Lys Arg Phe Ala Lys Leu Leu Ser Asp
            180                 185                 190

Arg Lys Lys Leu Arg Ala Asn Lys Ala Ser Tyr Gly Pro Gly Gln Leu
        195                 200                 205

Gly Glu Met Val Thr Val Leu Ser Ile Asp Gly Gly Ile Arg Gly
210                 215                 220

Ile Ile Pro Ala Thr Ile Leu Glu Phe Leu Glu Gly Leu Gln Glu
225                 230                 235                 240

Met Asp Asn Asn Ala Asp Ala Arg Leu Ala Asp Tyr Phe Asp Val Ile
                245                 250                 255

Gly Gly Thr Ser Thr Gly Leu Leu Thr Ala Met Ile Ser Thr Pro
            260                 265                 270

Asn Glu Asn Asn Arg Pro Phe Ala Ala Ala Lys Glu Ile Val Pro Phe
        275                 280                 285

Tyr Phe Glu His Gly Pro Gln Ile Phe Asn Pro Ser Gly Gln Ile Leu
290                 295                 300

Gly Pro Lys Tyr Asp Gly Lys Tyr Leu Met Gln Val Leu Gln Glu Lys
305                 310                 315                 320

Leu Gly Glu Thr Arg Val His Gln Ala Leu Thr Glu Val Val Ile Ser
                325                 330                 335

Ser Phe Asp Ile Lys Thr Asn Lys Pro Val Ile Phe Thr Lys Ser Asn
            340                 345                 350

Leu Ala Asn Ser Pro Glu Leu Asp Ala Lys Met Tyr Asp Ile
        355                 360                 365
```

<210> SEQ ID NO 26
<211> LENGTH: 1128
<212> TYPE: DNA
<213> ORGANISM: synthetic
<220> FEATURE:
<221> NAME/KEY: DNA
<222> LOCATION: (1)..(1128)
<223> OTHER INFORMATION: pMON37407 sequence encoding permutein protein

<400> SEQUENCE: 26

```
tcgagaaaag agaggctgaa gctacatata cagcaaaaga ggcagctacc tggactgctg      60
tacattggat gttagttata cagaaaatga ctgatgcagc aagttcttac atgactgatt     120
attacctttc tactgctttt caagctcttg attcaaaaaa caattacctc agggttcaag     180
aaaatgcatt aacaggcaca actactgaaa tggatgatgc ttctgaggct aatatggaat     240
tattagtaca agttggtgaa aacttattga agaaaccagt ttccgaagac aatcctgaaa     300
cctatgagga agctctaaag aggtttgcaa aattgctctc tgataggaag aaactccgat     360
caaacaaagc ttcttatgga ccaggacagt tgggagaaat ggtgactgtt cttagtattg     420
atggaggtgg aattagaggg atcattccgg ctaccattct cgaatttctt gaaggacaac     480
ttcaggaaat ggacaataat gcagatgcaa gacttgcaga ttactttgat gtaattggag     540
gaacaagtac aggaggttta ttgactgcta tgataagtac tccaaatgaa acaatcgac      600
cctttgctgc tgccaaagaa attgtacctt tttacttcga acatggccct cagattttta     660
atcctagtgg tcaaatttta ggcccaaaat atgatggaaa atatcttatg caagttcttc     720
aagaaaaact tggagaaact cgtgtgcatc aagctttgac agaagttgtc atctcaagct     780
ttgacatcaa aacaaataag ccagtaatat tcactaagtc aaatttagca aactctccag     840
aattggatgc taagatgtat gacataagtt attccacagc agcagctcca acatattttc     900
ctccgcatta ctttgttact aatactagta atggagatga atatgagttc aatcttgttg     960
atggtgctgt tgctactgtt gctgatccgg cgttattatc cattagcgtt gcaacgagac    1020
ttgcacaaaa ggatccagca tttgcttcaa ttaggtcatt gaattacaaa aaaatgctgt    1080
tgctctcatt aggcactggc actacttcag agtttgataa ataatgag                 1128
```

<210> SEQ ID NO 27
<211> LENGTH: 366
<212> TYPE: PRT
<213> ORGANISM: synthetic
<220> FEATURE:
<221> NAME/KEY: Protein
<222> LOCATION: (1)..(366)
<223> OTHER INFORMATION: Permutein protein encoded by pMON37407 sequence

<400> SEQUENCE: 27

```
Thr Tyr Thr Ala Lys Glu Ala Ala Thr Trp Thr Ala Val His Trp Met
1               5                   10                  15

Leu Val Ile Gln Lys Met Thr Asp Ala Ala Ser Ser Tyr Met Thr Asp
            20                  25                  30

Tyr Tyr Leu Ser Thr Ala Phe Gln Ala Leu Asp Ser Lys Asn Asn Tyr
        35                  40                  45

Leu Arg Val Gln Glu Asn Ala Leu Thr Gly Thr Thr Glu Met Asp
    50                  55                  60

Asp Ala Ser Glu Ala Asn Met Glu Leu Leu Val Gln Val Gly Glu Asn
65                  70                  75                  80

Leu Leu Lys Lys Pro Val Ser Glu Asp Asn Pro Glu Thr Tyr Glu Glu
```

```
                    85                  90                  95
Ala Leu Lys Arg Phe Ala Lys Leu Leu Ser Asp Arg Lys Lys Leu Arg
                100                 105                 110

Ser Asn Lys Ala Ser Tyr Gly Pro Gly Gln Leu Gly Glu Met Val Thr
            115                 120                 125

Val Leu Ser Ile Asp Gly Gly Ile Arg Gly Ile Ile Pro Ala Thr
        130                 135                 140

Ile Leu Glu Phe Leu Glu Gly Gln Leu Gln Glu Met Asp Asn Asn Ala
145                 150                 155                 160

Asp Ala Arg Leu Ala Asp Tyr Phe Asp Val Ile Gly Gly Thr Ser Thr
                165                 170                 175

Gly Gly Leu Leu Thr Ala Met Ile Ser Thr Pro Asn Glu Asn Asn Arg
            180                 185                 190

Pro Phe Ala Ala Ala Lys Glu Ile Val Pro Phe Tyr Phe Glu His Gly
        195                 200                 205

Pro Gln Ile Phe Asn Pro Ser Gly Gln Ile Leu Gly Pro Lys Tyr Asp
    210                 215                 220

Gly Lys Tyr Leu Met Gln Val Leu Gln Glu Lys Leu Gly Glu Thr Arg
225                 230                 235                 240

Val His Gln Ala Leu Thr Glu Val Val Ile Ser Ser Phe Asp Ile Lys
                245                 250                 255

Thr Asn Lys Pro Val Ile Phe Thr Lys Ser Asn Leu Ala Asn Ser Pro
            260                 265                 270

Glu Leu Asp Ala Lys Met Tyr Asp Ile Ser Tyr Ser Thr Ala Ala Ala
        275                 280                 285

Pro Thr Tyr Phe Pro Pro His Tyr Phe Val Thr Asn Thr Ser Asn Gly
    290                 295                 300

Asp Glu Tyr Glu Phe Asn Leu Val Asp Gly Ala Val Ala Thr Val Ala
305                 310                 315                 320

Asp Pro Ala Leu Leu Ser Ile Ser Val Ala Thr Arg Leu Ala Gln Lys
                325                 330                 335

Asp Pro Ala Phe Ala Ser Ile Arg Ser Leu Asn Tyr Lys Lys Met Leu
            340                 345                 350

Leu Leu Ser Leu Gly Thr Gly Thr Thr Ser Glu Phe Asp Lys
        355                 360                 365

<210> SEQ ID NO 28
<211> LENGTH: 1128
<212> TYPE: DNA
<213> ORGANISM: synthetic
<220> FEATURE:
<221> NAME/KEY: DNA
<222> LOCATION: (1)..(1128)
<223> OTHER INFORMATION: pMON37408 sequence encoding permutein protein

<400> SEQUENCE: 28
tcgagaaaag agaggctgaa gctaatgcat taacaggcac aactactgaa atggatgatg      60
cttctgaggc taatatggaa ttattagtac aagttggtga aaacttattg aagaaaccag     120
tttccgaaga caatcctgaa acctatgagg aagctctaaa gaggtttgca aaattgctct     180
ctgataggaa gaaactccga gcaaacaaag cttcttatgg accaggacag ttgggagaaa     240
tggtgactgt tcttagtatt gatggaggtg gaattagagg gatcattccg gctaccattc     300
tcgaatttct tgaaggacaa cttcaggaaa tggacaataa tgcagatgca agacttgcag     360
attactttga tgtaattgga ggaacaagta caggaggttt attgactgct atgataagta     420
```

-continued

```
ctccaaatga aaacaatcga cccctttgctg ctgccaaaga aattgtacct ttttacttcg    480
aacatggccc tcagattttt aatcctagtg gtcaaatttt aggcccaaaa tatgatggaa    540
aatatcttat gcaagttctt caagaaaaac ttggagaaac tcgtgtgcat caagctttga    600
cagaagttgt catctcaagc tttgacatca aaacaaataa gccagtaata ttcactaagt    660
caaatttagc aaactctcca gaattggatg ctaagatgta tgacataagt tattccacag    720
cagcagctcc aacatatttt cctccgcatt actttgttac taatactagt aatggagatg    780
aatatgagtt caatcttgtt gatggtgctg ttgctactgt tgctgatccg gcgttattat    840
ccattagcgt tgcaacgaga cttgcacaaa aggatccagc atttgcttca attaggtcat    900
tgaattacaa aaaatgctg ttgctctcat taggcactgg cactacttca gagtttgata    960
aaacatatac agcaaaagag gcagctacct ggactgctgt acattggatg ttagttatac   1020
agaaaatgac tgatgcagca agttcttaca tgactgatta ttacctttct actgcttttc   1080
aagctcttga ttcaaaaaac aattacctca gggttcaaga ataatgag                1128
```

<210> SEQ ID NO 29
<211> LENGTH: 366
<212> TYPE: PRT
<213> ORGANISM: synthetic
<220> FEATURE:
<221> NAME/KEY: Protein
<222> LOCATION: (1)..(366)
<223> OTHER INFORMATION: Permutein protein encoded by pMON37408

<400> SEQUENCE: 29

```
Asn Ala Leu Thr Gly Thr Thr Thr Glu Met Asp Asp Ala Ser Glu Ala
1               5                   10                  15

Asn Met Glu Leu Leu Val Gln Val Gly Glu Asn Leu Leu Lys Lys Pro
                20                  25                  30

Val Ser Glu Asp Asn Pro Glu Thr Tyr Glu Glu Ala Leu Lys Arg Phe
            35                  40                  45

Ala Lys Leu Leu Ser Asp Arg Lys Lys Leu Arg Ala Asn Lys Ala Ser
        50                  55                  60

Tyr Gly Pro Gly Gln Leu Gly Glu Met Val Thr Val Leu Ser Ile Asp
65                  70                  75                  80

Gly Gly Gly Ile Arg Gly Ile Ile Pro Ala Thr Ile Leu Glu Phe Leu
                85                  90                  95

Glu Gly Gln Leu Gln Glu Met Asp Asn Asn Ala Asp Ala Arg Leu Ala
                100                 105                 110

Asp Tyr Phe Asp Val Ile Gly Gly Thr Ser Thr Gly Gly Leu Leu Thr
            115                 120                 125

Ala Met Ile Ser Thr Pro Asn Glu Asn Asn Arg Pro Phe Ala Ala Ala
        130                 135                 140

Lys Glu Ile Val Pro Phe Tyr Phe Glu His Gly Pro Gln Ile Phe Asn
145                 150                 155                 160

Pro Ser Gly Gln Ile Leu Gly Pro Lys Tyr Asp Gly Lys Tyr Leu Met
                165                 170                 175

Gln Val Leu Gln Glu Lys Leu Gly Glu Thr Arg Val His Gln Ala Leu
            180                 185                 190

Thr Glu Val Val Ile Ser Ser Phe Asp Ile Lys Thr Asn Lys Pro Val
        195                 200                 205

Ile Phe Thr Lys Ser Asn Leu Ala Asn Ser Pro Glu Leu Asp Ala Lys
    210                 215                 220

Met Tyr Asp Ile Ser Tyr Ser Thr Ala Ala Ala Pro Thr Tyr Phe Pro
```

| 225 | | | 230 | | | 235 | | | 240 | | |
|---|---|---|---|---|---|---|---|---|---|---|---|

Pro His Tyr Phe Val Thr Asn Thr Ser Asn Gly Asp Glu Tyr Glu Phe
                             245                         250                  255

Asn Leu Val Asp Gly Ala Val Ala Thr Val Ala Asp Pro Ala Leu Leu
            260                         265                     270

Ser Ile Ser Val Ala Thr Arg Leu Ala Gln Lys Asp Pro Ala Phe Ala
      275                     280                     285

Ser Ile Arg Ser Leu Asn Tyr Lys Lys Met Leu Leu Leu Ser Leu Gly
         290                     295                  300

Thr Gly Thr Thr Ser Glu Phe Asp Lys Thr Tyr Thr Ala Lys Glu Ala
305                      310                     315                320

Ala Thr Trp Thr Ala Val His Trp Met Leu Val Ile Gln Lys Met Thr
            325                         330                     335

Asp Ala Ala Ser Ser Tyr Met Thr Asp Tyr Tyr Leu Ser Thr Ala Phe
         340                     345                  350

Gln Ala Leu Asp Ser Lys Asn Asn Tyr Leu Arg Val Gln Glu
      355                     360                  365

<210> SEQ ID NO 30
<211> LENGTH: 1158
<212> TYPE: DNA
<213> ORGANISM: synthetic
<220> FEATURE:
<221> NAME/KEY: DNA
<222> LOCATION: (1)..(1158)
<223> OTHER INFORMATION: pMON40701 sequence encoding permutein protein

<400> SEQUENCE: 30

```
atggccacca ccaagagctt cctcatcctg atcttcatga tcctggccac caccagcagc      60
accttcgccc agctcggcga gatggtgacc gtgctctcca tcgacggcgg tggcatcagg     120
ggcatcatcc cggccaccat cctggagttc ctggagggcc aactccagga gatggacaac     180
aacgccgacg cccgcctggc cgactacttc gacgtgatcg gtggcaccag caccggcgtt     240
ctcctgaccg ccatgatctc cactccgaac gagaacaacc gcccttcgc cgctgcgaag      300
gagatcgtcc cgttctactt cgaacacggc cctcagattt caacccctc gggtcaaatc      360
ctgggcccca gtacgacgg caagtacctt atgcaagtgc ttcaggagaa gctgggcgag      420
actagggtgc accaggcgct gaccgaggtc gtcatctcca gcttcgacat caagaccaac     480
aagccagtca tcttcaccaa gtccaacctg ccaacagcc ggagctgga cgctaagatg       540
tacgacatct cctactccac tgctgccgct cccacgtact ccctccgca ctacttcgtc      600
accaacacca gcaacggcga cgagtacgag ttcaaccttg ttgacggtgc ggtggctacg     660
gtggcggacc cggcgctcct gtccatcagc gtcgccacgc gcctggccca gaaggatcca     720
gccttcgcta gcattaggag cctcaactac aagaagatgc tgctgctcag cctgggcact     780
ggcacgacct ccgagttcga caagacctac actgccaagg aggccgctac ctggaccgcc     840
gtccattgga tgctggtcat ccagaagatg acggacgccg cttccagcta catgaccgac     900
tactacctct ccactgcgtt ccaggcgctt gactccaaga caactacct ccgtgttcag      960
gagaatgccc tcactggcac cacgaccgag atggacgatg cctccgaggc caacatggag    1020
ctgctcgtcc aggtgggtga aacctcctg aagaagcccg tctccgaaga caatcccgag     1080
acctatgagg aagcgctcaa gcgctttgcc aagctgctct ctgataggaa gaaactccgc    1140
gctaacaagg ccagctac                                                  1158
```

-continued

```
<210> SEQ ID NO 31
<211> LENGTH: 386
<212> TYPE: PRT
<213> ORGANISM: synthetic
<220> FEATURE:
<221> NAME/KEY: Protein
<222> LOCATION: (1)..(386)
<223> OTHER INFORMATION: Permutein protein encoded by pMON40701 sequence

<400> SEQUENCE: 31

Met Ala Thr Thr Lys Ser Phe Leu Ile Leu Ile Phe Met Ile Leu Ala
1               5                   10                  15

Thr Thr Ser Ser Thr Phe Ala Gln Leu Gly Glu Met Val Thr Val Leu
            20                  25                  30

Ser Ile Asp Gly Gly Gly Ile Arg Gly Ile Ile Pro Ala Thr Ile Leu
        35                  40                  45

Glu Phe Leu Glu Gly Gln Leu Gln Glu Met Asp Asn Asn Ala Asp Ala
    50                  55                  60

Arg Leu Ala Asp Tyr Phe Asp Val Ile Gly Gly Thr Ser Thr Gly Gly
65                  70                  75                  80

Leu Leu Thr Ala Met Ile Ser Thr Pro Asn Glu Asn Asn Arg Pro Phe
                85                  90                  95

Ala Ala Ala Lys Glu Ile Val Pro Phe Tyr Phe Glu His Gly Pro Gln
            100                 105                 110

Ile Phe Asn Pro Ser Gly Gln Ile Leu Gly Pro Lys Tyr Asp Gly Lys
        115                 120                 125

Tyr Leu Met Gln Val Leu Gln Glu Lys Leu Gly Glu Thr Arg Val His
    130                 135                 140

Gln Ala Leu Thr Glu Val Val Ile Ser Ser Phe Asp Ile Lys Thr Asn
145                 150                 155                 160

Lys Pro Val Ile Phe Thr Lys Ser Asn Leu Ala Asn Ser Pro Glu Leu
                165                 170                 175

Asp Ala Lys Met Tyr Asp Ile Ser Tyr Ser Thr Ala Ala Pro Thr
            180                 185                 190

Tyr Phe Pro Pro His Tyr Phe Val Thr Asn Thr Ser Asn Gly Asp Glu
        195                 200                 205

Tyr Glu Phe Asn Leu Val Asp Gly Ala Val Ala Thr Val Ala Asp Pro
    210                 215                 220

Ala Leu Leu Ser Ile Ser Val Ala Thr Arg Leu Ala Gln Lys Asp Pro
225                 230                 235                 240

Ala Phe Ala Ser Ile Arg Ser Leu Asn Tyr Lys Lys Met Leu Leu Leu
                245                 250                 255

Ser Leu Gly Thr Gly Thr Thr Ser Glu Phe Asp Lys Thr Tyr Thr Ala
            260                 265                 270

Lys Glu Ala Ala Thr Trp Thr Ala Val His Trp Met Leu Val Ile Gln
        275                 280                 285

Lys Met Thr Asp Ala Ala Ser Ser Tyr Met Thr Asp Tyr Tyr Leu Ser
    290                 295                 300

Thr Ala Phe Gln Ala Leu Asp Ser Lys Asn Asn Tyr Leu Arg Val Gln
305                 310                 315                 320

Glu Asn Ala Leu Thr Gly Thr Thr Thr Glu Met Asp Asp Ala Ser Glu
                325                 330                 335

Ala Asn Met Glu Leu Leu Val Gln Val Gly Glu Asn Leu Leu Lys Lys
            340                 345                 350

Pro Val Ser Glu Asp Asn Pro Glu Thr Tyr Glu Glu Ala Leu Lys Arg
        355                 360                 365
```

Phe Ala Lys Leu Leu Ser Asp Arg Lys Lys Leu Arg Ala Asn Lys Ala
        370                 375                 380

Ser Tyr
385

<210> SEQ ID NO 32
<211> LENGTH: 1167
<212> TYPE: DNA
<213> ORGANISM: synthetic
<220> FEATURE:
<221> NAME/KEY: DNA
<222> LOCATION: (1)..(1167)
<223> OTHER INFORMATION: pMON40703 sequence encoding permutein protein

<400> SEQUENCE: 32

```
atggccacca ccaagagctt cctcatcctg atcttcatga tcctggccac caccagcagc      60
accttcgcca gcctcaacta caagaagatg ctgctgctca gcctgggcac tggcacgacc     120
tccgagttcg acaagaccta cactgccaag gaggccgcta cctggaccgc cgtccattgg     180
atgctggtca tccagaagat gacggacgcc gcttccagct acatgaccga ctactacctc     240
tccactgcgt tccaggcgct tgactccaag aacaactacc tccgtgttca ggagaatgcc     300
ctcactggca ccacgaccga gatggacgat gcctccgagg ccaacatgga gctgctcgtc     360
caggtgggtg agaacctcct gaagaagccc gtctccgaag acaatcccga gacctatgag     420
gaagcgctca gcgctttgc caagctgctc tctgatagga gaaactccg cgctaacaag      480
gccagctacg gaccaggaca gctcggcgag atggtgaccg tgctctccat cgacggcggt     540
ggcatcaggg gcatcatccc ggccaccatc ctggagttcc tggagggcca actccaggag     600
atggacaaca acgccgacgc ccgcctggcc gactacttcg acgtgatcgg tggcaccagc     660
accggcggtc tcctgaccgc catgatctcc actccgaacg agaacaaccg ccccttcgcc     720
gctgcgaagg agatcgtccc gttctacttc gaacacggcc ctcagatttt caacccctcg     780
ggtcaaatcc tgggccccaa gtacgacggc aagtacctta tgcaagtgct tcaggagaag     840
ctgggcgaga ctagggtgca ccaggcgctg accgaggtcg tcatctccag cttcgacatc     900
aagaccaaca agccagtcat cttcaccaag tccaacctgg ccaacagccc ggagctggac     960
gctaagatgt acgacatctc ctactccact gctgccgctc ccacgtactt ccctccgcac    1020
tacttcgtca ccaacaccag caacggcgac gagtacgagt tcaaccttgt tgacggtgcg    1080
gtggctacgg tggcggaccc ggcgctcctg tccatcagcg tcgccacgcg cctggcccag    1140
aaggatccag ccttcgctag cattagg                                        1167
```

<210> SEQ ID NO 33
<211> LENGTH: 389
<212> TYPE: PRT
<213> ORGANISM: synthetic
<220> FEATURE:
<221> NAME/KEY: Protein
<222> LOCATION: (1)..(389)
<223> OTHER INFORMATION: Permutein protein encoded by pMON40703 sequence

<400> SEQUENCE: 33

Met Ala Thr Thr Lys Ser Phe Leu Ile Leu Ile Phe Met Ile Leu Ala
1               5                   10                  15

Thr Thr Ser Ser Thr Phe Ala Ser Leu Asn Tyr Lys Lys Met Leu Leu
                20                  25                  30

Leu Ser Leu Gly Thr Gly Thr Thr Ser Glu Phe Asp Lys Thr Tyr Thr
            35                  40                  45

```
Ala Lys Glu Ala Ala Thr Trp Thr Ala Val His Trp Met Leu Val Ile
    50                  55                  60
Gln Lys Met Thr Asp Ala Ala Ser Ser Tyr Met Thr Asp Tyr Tyr Leu
 65                  70                  75                  80
Ser Thr Ala Phe Gln Ala Leu Asp Ser Lys Asn Asn Tyr Leu Arg Val
                 85                  90                  95
Gln Glu Asn Ala Leu Thr Gly Thr Thr Thr Glu Met Asp Asp Ala Ser
            100                 105                 110
Glu Ala Asn Met Glu Leu Leu Val Gln Val Gly Glu Asn Leu Leu Lys
            115                 120                 125
Lys Pro Val Ser Glu Asp Asn Pro Glu Thr Tyr Glu Glu Ala Leu Lys
        130                 135                 140
Arg Phe Ala Lys Leu Leu Ser Asp Arg Lys Lys Leu Arg Ala Asn Lys
145                 150                 155                 160
Ala Ser Tyr Gly Pro Gly Gln Leu Gly Glu Met Val Thr Val Leu Ser
                165                 170                 175
Ile Asp Gly Gly Gly Ile Arg Gly Ile Ile Pro Ala Thr Ile Leu Glu
            180                 185                 190
Phe Leu Glu Gly Gln Leu Gln Glu Met Asp Asn Asn Ala Asp Ala Arg
            195                 200                 205
Leu Ala Asp Tyr Phe Asp Val Ile Gly Gly Thr Ser Thr Gly Gly Leu
210                 215                 220
Leu Thr Ala Met Ile Ser Thr Pro Asn Glu Asn Asn Arg Pro Phe Ala
225                 230                 235                 240
Ala Ala Lys Glu Ile Val Pro Phe Tyr Phe Glu His Gly Pro Gln Ile
                245                 250                 255
Phe Asn Pro Ser Gly Gln Ile Leu Gly Pro Lys Tyr Asp Gly Lys Tyr
            260                 265                 270
Leu Met Gln Val Leu Gln Glu Lys Leu Gly Glu Thr Arg Val His Gln
            275                 280                 285
Ala Leu Thr Glu Val Val Ile Ser Ser Phe Asp Ile Lys Thr Asn Lys
        290                 295                 300
Pro Val Ile Phe Thr Lys Ser Asn Leu Ala Asn Ser Pro Glu Leu Asp
305                 310                 315                 320
Ala Lys Met Tyr Asp Ile Ser Tyr Ser Thr Ala Ala Pro Thr Tyr
                325                 330                 335
Phe Pro Pro His Tyr Phe Val Thr Asn Thr Ser Asn Gly Asp Glu Tyr
            340                 345                 350
Glu Phe Asn Leu Val Asp Gly Ala Val Ala Thr Val Ala Asp Pro Ala
            355                 360                 365
Leu Leu Ser Ile Ser Val Ala Thr Arg Leu Ala Gln Lys Asp Pro Ala
        370                 375                 380
Phe Ala Ser Ile Arg
385

<210> SEQ ID NO 34
<211> LENGTH: 1167
<212> TYPE: DNA
<213> ORGANISM: synthetic
<220> FEATURE:
<221> NAME/KEY: DNA
<222> LOCATION: (1)..(1167)
<223> OTHER INFORMATION: pMON40705 sequence encoding permutein protein

<400> SEQUENCE: 34
```

-continued

```
atggccacca ccaagagctt cctcatcctg atcttcatga tcctggccac caccagcagc    60
accttcgcca cctacactgc caaggaggcc gctacctgga ccgccgtcca ttggatgctg    120
gtcatccaga agatgacgga cgccgcttcc agctacatga ccgactacta cctctccact    180
gcgttccagg cgcttgactc caagaacaac tacctccgtg ttcaggagaa tgccctcact    240
ggcaccacga ccgagatgga cgatgcctcc gaggccaaca tggagctgct cgtccaggtg    300
ggtgagaacc tcctgaagaa gcccgtctcc aagacaatc ccgagaccta tgaggaagcg    360
ctcaagcgct ttgccaagct gctctctgat aggaagaaac tccgcgctaa caaggccagc    420
tacggaccag gacagctcgg cgagatggtg accgtgctct ccatcgacgg cggtggcatc    480 agggcatca tcccggccac catcctggag ttcctggagg ccaactcca ggagatggac    540 aacaacgccg acgcccgcct ggccgactac ttcgacgtga tcggtggcac cagcaccggc    600
ggtctcctga ccgccatgat ctccactccg aacgagaaca accgcccctt cgccgctgcg    660
aaggagatcg tcccgttcta cttcgaacac ggccctcaga ttttcaaccc ctcgggtcaa    720
atcctgggcc ccaagtacga cggcaagtac cttatgcaag tgcttcagga aagctgggc    780 gagactaggg tgcaccaggc gctgaccgag gtcgtcatct ccagcttcga catcaagacc    840
aacaagccag tcatcttcac caagtccaac ctggccaaca gccggagct ggacgctaag    900 atgtacgaca tctcctactc cactgctgcc gctcccacgt acttccctcc gcactacttc    960
gtcaccaaca ccagcaacgg cgacgagtac gagttcaacc ttgttgacgg tgcggtggct    1020
acggtggcgg acccggcgct cctgtccatc agcgtcgcca cgcgcctggc ccagaaggat    1080
ccagccttcg ctagcattag gagcctcaac tacaagaaga tgctgctgct cagcctgggc    1140
actggcacga cctccgagtt cgacaag                                       1167
```

<210> SEQ ID NO 35
<211> LENGTH: 389
<212> TYPE: PRT
<213> ORGANISM: synthetic
<220> FEATURE:
<221> NAME/KEY: Protein
<222> LOCATION: (1)..(389)
<223> OTHER INFORMATION: Permutein protein encoded by pMON40705

<400> SEQUENCE: 35

```
Met Ala Thr Thr Lys Ser Phe Leu Ile Leu Ile Phe Met Ile Leu Ala
1               5                   10                  15

Thr Thr Ser Ser Thr Phe Ala Tyr Thr Ala Lys Glu Ala Ala Thr
            20                  25                  30

Trp Thr Ala Val His Trp Met Leu Val Ile Gln Lys Met Thr Asp Ala
        35                  40                  45

Ala Ser Ser Tyr Met Thr Asp Tyr Tyr Leu Ser Thr Ala Phe Gln Ala
    50                  55                  60

Leu Asp Ser Lys Asn Asn Tyr Leu Arg Val Gln Glu Asn Ala Leu Thr
65                  70                  75                  80

Gly Thr Thr Thr Glu Met Asp Asp Ala Ser Glu Ala Asn Met Glu Leu
                85                  90                  95

Leu Val Gln Val Gly Glu Asn Leu Leu Lys Lys Pro Val Ser Glu Asp
            100                 105                 110

Asn Pro Glu Thr Tyr Glu Glu Ala Leu Lys Arg Phe Ala Lys Leu Leu
        115                 120                 125

Ser Asp Arg Lys Lys Leu Arg Ala Asn Lys Ala Ser Tyr Gly Pro Gly
    130                 135                 140
```

```
Gln Leu Gly Glu Met Val Thr Val Leu Ser Ile Asp Gly Gly Ile
145                 150                 155                 160

Arg Gly Ile Ile Pro Ala Thr Ile Leu Glu Phe Leu Glu Gly Gln Leu
            165                 170                 175

Gln Glu Met Asp Asn Asn Ala Asp Ala Arg Leu Ala Asp Tyr Phe Asp
            180                 185                 190

Val Ile Gly Gly Thr Ser Thr Gly Gly Leu Leu Thr Ala Met Ile Ser
            195                 200                 205

Thr Pro Asn Glu Asn Asn Arg Pro Phe Ala Ala Lys Glu Ile Val
210                 215                 220

Pro Phe Tyr Phe Glu His Gly Pro Gln Ile Phe Asn Pro Ser Gly Gln
225                 230                 235                 240

Ile Leu Gly Pro Lys Tyr Asp Gly Lys Tyr Leu Met Gln Val Leu Gln
            245                 250                 255

Glu Lys Leu Gly Glu Thr Arg Val His Gln Ala Leu Thr Glu Val Val
            260                 265                 270

Ile Ser Ser Phe Asp Ile Lys Thr Asn Lys Pro Val Ile Phe Thr Lys
            275                 280                 285

Ser Asn Leu Ala Asn Ser Pro Glu Leu Asp Ala Lys Met Tyr Asp Ile
290                 295                 300

Ser Tyr Ser Thr Ala Ala Ala Pro Thr Tyr Phe Pro Pro His Tyr Phe
305                 310                 315                 320

Val Thr Asn Thr Ser Asn Gly Asp Glu Tyr Glu Phe Asn Leu Val Asp
            325                 330                 335

Gly Ala Val Ala Thr Val Ala Asp Pro Ala Leu Leu Ser Ile Ser Val
            340                 345                 350

Ala Thr Arg Leu Ala Gln Lys Asp Pro Ala Phe Ala Ser Ile Arg Ser
            355                 360                 365

Leu Asn Tyr Lys Lys Met Leu Leu Leu Ser Leu Gly Thr Gly Thr Thr
            370                 375                 380

Ser Glu Phe Asp Lys
385

<210> SEQ ID NO 36
<211> LENGTH: 10
<212> TYPE: PRT
<213> ORGANISM: synthetic
<220> FEATURE:
<221> NAME/KEY: Protein
<222> LOCATION: (1)..(10)
<223> OTHER INFORMATION: corn homolog peptide

<400> SEQUENCE: 36

Cys Ile Phe Asp Ser Thr Tyr Thr Ala Lys
1               5                   10

<210> SEQ ID NO 37
<211> LENGTH: 1161
<212> TYPE: DNA
<213> ORGANISM: Solanum cardiophyllum
<220> FEATURE:
<221> NAME/KEY: exon
<222> LOCATION: (1)..(1161)
<223> OTHER INFORMATION: patatin homolog Pat17 nucleic acid and amino
      acid translation

<400> SEQUENCE: 37 atg gca act act aaa tct ttt tta att tta ata ttt atg ata tta gca      48
Met Ala Thr Thr Lys Ser Phe Leu Ile Leu Ile Phe Met Ile Leu Ala
1               5                   10                  15
```

```
act act agt tca aca ttt gct cag ttg gga gaa atg gtg act gtt ctt      96
Thr Thr Ser Ser Thr Phe Ala Gln Leu Gly Glu Met Val Thr Val Leu
            20                  25                  30 agt att gat gga ggt gga att aga ggg atc att ccg gct acc att ctc     144
Ser Ile Asp Gly Gly Gly Ile Arg Gly Ile Ile Pro Ala Thr Ile Leu
        35                  40                  45 gaa ttt ctt gaa gga caa ctt cag gaa atg gac aat aat gca gat gca     192
Glu Phe Leu Glu Gly Gln Leu Gln Glu Met Asp Asn Asn Ala Asp Ala
    50                  55                  60 aga ctt gca gat tac ttt gat gta att gga gga aca agt aca gga ggt     240
Arg Leu Ala Asp Tyr Phe Asp Val Ile Gly Gly Thr Ser Thr Gly Gly
65                  70                  75                  80 tta ttg act gct atg ata agt act cca aat gaa aac aat cga ccc ttt     288
Leu Leu Thr Ala Met Ile Ser Thr Pro Asn Glu Asn Asn Arg Pro Phe
            85                  90                  95 gct gct gcc aaa gaa att gta cct ttt tac ttc gaa cat ggc cct cag     336
Ala Ala Ala Lys Glu Ile Val Pro Phe Tyr Phe Glu His Gly Pro Gln
        100                 105                 110 att ttt aat cct agt ggt caa att tta ggc cca aaa tat gat gga aaa     384
Ile Phe Asn Pro Ser Gly Gln Ile Leu Gly Pro Lys Tyr Asp Gly Lys
    115                 120                 125 tat ctt atg caa gtt ctt caa gaa aaa ctt gga gaa act cgt gtg cat     432
Tyr Leu Met Gln Val Leu Gln Glu Lys Leu Gly Glu Thr Arg Val His
130                 135                 140 caa gct ttg aca gaa gtt gtc atc tca agc ttt gac atc aaa aca aat     480
Gln Ala Leu Thr Glu Val Val Ile Ser Ser Phe Asp Ile Lys Thr Asn
145                 150                 155                 160 aag cca gta ata ttc act aag tca aat tta gca aac tct cca gaa ttg     528
Lys Pro Val Ile Phe Thr Lys Ser Asn Leu Ala Asn Ser Pro Glu Leu
            165                 170                 175 gat gct aag atg tat gac ata agt tat tcc aca gca gca gct cca aca     576
Asp Ala Lys Met Tyr Asp Ile Ser Tyr Ser Thr Ala Ala Ala Pro Thr
        180                 185                 190 tat ttt cct ccg cat tac ttt gtt act aat act agt aat gga gat gaa     624
Tyr Phe Pro Pro His Tyr Phe Val Thr Asn Thr Ser Asn Gly Asp Glu
    195                 200                 205 tat gag ttc aat ctt gtt gat ggt gct gtt gct act gtt gct gat ccg     672
Tyr Glu Phe Asn Leu Val Asp Gly Ala Val Ala Thr Val Ala Asp Pro
210                 215                 220 gcg tta tta tcc att agc gtt gca acg aga ctt gca caa aag gat cca     720
Ala Leu Leu Ser Ile Ser Val Ala Thr Arg Leu Ala Gln Lys Asp Pro
225                 230                 235                 240 gca ttt gct tca att agg tca ttg aat tac aaa aaa atg ctg ttg ctc     768
Ala Phe Ala Ser Ile Arg Ser Leu Asn Tyr Lys Lys Met Leu Leu Leu
            245                 250                 255 tca tta ggc act ggc act act tca gag ttt gat aaa aca tat aca gca     816
Ser Leu Gly Thr Gly Thr Thr Ser Glu Phe Asp Lys Thr Tyr Thr Ala
        260                 265                 270 aaa gag gca gct acc tgg act gct gta cat tgg atg tta gtt ata cag     864
Lys Glu Ala Ala Thr Trp Thr Ala Val His Trp Met Leu Val Ile Gln
    275                 280                 285 aaa atg act gat gca gca agt tct tac atg act gat tat tac ctt tct     912
Lys Met Thr Asp Ala Ala Ser Ser Tyr Met Thr Asp Tyr Tyr Leu Ser
290                 295                 300 act gct ttt caa gct ctt gat tca aaa aac aat tac ctc agg gtt caa     960
Thr Ala Phe Gln Ala Leu Asp Ser Lys Asn Asn Tyr Leu Arg Val Gln
305                 310                 315                 320 gaa aat gca tta aca ggc aca act act gaa atg gat gat gct tct gag    1008
Glu Asn Ala Leu Thr Gly Thr Thr Thr Glu Met Asp Asp Ala Ser Glu
```

```
                      325                 330                 335
gct aat atg gaa tta tta gta caa gtt ggt gaa aac tta ttg aag aaa        1056
Ala Asn Met Glu Leu Leu Val Gln Val Gly Glu Asn Leu Leu Lys Lys
                340                 345                 350 cca gtt tcc gaa gac aat cct gaa acc tat gag gaa gct cta aag agg        1104
Pro Val Ser Glu Asp Asn Pro Glu Thr Tyr Glu Glu Ala Leu Lys Arg
            355                 360                 365 ttt gca aaa ttg ctc tct gat agg aag aaa ctc cga gca aac aaa gct        1152
Phe Ala Lys Leu Leu Ser Asp Arg Lys Lys Leu Arg Ala Asn Lys Ala
        370                 375                 380 tct tat taa                                                            1161
Ser Tyr
385
```

<210> SEQ ID NO 38
<211> LENGTH: 1158
<212> TYPE: DNA
<213> ORGANISM: Solanum tuberosum
<220> FEATURE:
<221> NAME/KEY: DNA
<222> LOCATION: (1)..(1158)
<223> OTHER INFORMATION: DNA sequence encoding a patatin (acyl lipid hydrolase) protein

<400> SEQUENCE: 38

```
atggcaacta ctaaatcttt tttaatttta atatttatga tattagcaac tactagttca      60
acatttgctc agttgggaga atggtgact gttcttagta ttgatggagg tggaattaga      120
gggatcattc cggctaccat tctcgaattt cttgaaggac aacttcagga aatggacaat     180
aatgcagatg caagacttgc agattacttt gatgtaattg gaggaacaag tacaggaggt     240
ttattgactg ctatgataag tactccaaat gaaaacaatc gacccttgc tgctgccaaa     300
gaaattgtac ctttttactt cgaacatggc cctcagattt taatcctag tggtcaaatt     360
ttaggcccaa aatatgatgg aaaatatctt atgcaagttc ttcaagaaaa acttggagaa    420
actcgtgtgc atcaagcttt gacagaagtt gtcatctcaa gctttgacat caaaacaaat   480
aagccagtaa tattcactaa gtcaaattta gcaaactctc agaattgga tgctaagatg    540
tatgacataa gttattccac agcagcagct ccaacatatt ttcctccgca ttactttgtt    600
actaatacta gtaatggaga tgaatatgag ttcaatcttg ttgatggtgc tgttgctact   660
gttgctgatc cggcgttatt atccattagc gttgcaacga gcttgcaca aaaggatcca    720
gcatttgctt caattaggtc attgaattac aaaaaaatgc tgttgctctc attaggcact   780
ggcactactt cagagtttga taaaacatat acagcaaaag aggcagctac ctggactgct   840
gtacattgga tgttagttat acagaaaatg actgatgcag caagttctta catgactgat   900
tattaccttt ctactgcttt tcaagctctt gattcaaaaa acaattacct cagggttcaa  960
gaaaatgcat taacaggcac aactactgaa atggatgatg cttctgaggc taatatggaa   1020
ttattagtac aagttggtga aaacttattg aagaaccag tttccgaaga caatcctgaa   1080
acctatgagg aagctctaaa gaggttgtgca aaattgctct ctgataggaa gaaactccga   1140
gcaaacaaag cttcttat                                                  1158
```

<210> SEQ ID NO 39
<211> LENGTH: 386
<212> TYPE: PRT
<213> ORGANISM: potato
<220> FEATURE:
<221> NAME/KEY: Protein
<222> LOCATION: (1)..(386)

-continued

```
<223> OTHER INFORMATION: potato patatin protein sequence

<400> SEQUENCE: 39

Met Ala Thr Thr Lys Ser Phe Leu Ile Leu Ile Phe Met Ile Leu Ala
1               5                   10                  15

Thr Thr Ser Ser Thr Phe Ala Gln Leu Gly Glu Met Val Thr Val Leu
            20                  25                  30

Ser Ile Asp Gly Gly Gly Ile Arg Gly Ile Ile Pro Ala Thr Ile Leu
            35                  40                  45

Glu Phe Leu Glu Gly Gln Leu Gln Glu Met Asp Asn Asn Ala Asp Ala
        50                  55                  60

Arg Leu Ala Asp Tyr Phe Asp Val Ile Gly Thr Ser Thr Gly Gly
65                  70                  75                  80

Leu Leu Thr Ala Met Ile Ser Thr Pro Asn Glu Asn Asn Arg Pro Phe
                85                  90                  95

Ala Ala Ala Lys Glu Ile Val Pro Phe Tyr Phe Glu His Gly Pro Gln
            100                 105                 110

Ile Phe Asn Pro Ser Gly Gln Ile Leu Gly Pro Lys Tyr Asp Gly Lys
            115                 120                 125

Tyr Leu Met Gln Val Leu Gln Glu Lys Leu Gly Glu Thr Arg Val His
        130                 135                 140

Gln Ala Leu Thr Glu Val Val Ile Ser Ser Phe Asp Ile Lys Thr Asn
145                 150                 155                 160

Lys Pro Val Ile Phe Thr Lys Ser Asn Leu Ala Asn Ser Pro Glu Leu
                165                 170                 175

Asp Ala Lys Met Tyr Asp Ile Ser Tyr Ser Thr Ala Ala Pro Thr
            180                 185                 190

Tyr Phe Pro Pro His Tyr Phe Val Thr Asn Thr Ser Asn Gly Asp Glu
            195                 200                 205

Tyr Glu Phe Asn Leu Val Asp Gly Ala Val Ala Thr Val Ala Asp Pro
        210                 215                 220

Ala Leu Leu Ser Ile Ser Val Ala Thr Arg Leu Ala Gln Lys Asp Pro
225                 230                 235                 240

Ala Phe Ala Ser Ile Arg Ser Leu Asn Tyr Lys Lys Met Leu Leu Leu
                245                 250                 255

Ser Leu Gly Thr Gly Thr Thr Ser Glu Phe Asp Lys Thr Tyr Thr Ala
            260                 265                 270

Lys Glu Ala Ala Thr Trp Thr Ala Val His Trp Met Leu Val Ile Gln
        275                 280                 285

Lys Met Thr Asp Ala Ala Ser Ser Tyr Met Thr Asp Tyr Tyr Leu Ser
    290                 295                 300

Thr Ala Phe Gln Ala Leu Asp Ser Lys Asn Asn Tyr Leu Arg Val Gln
305                 310                 315                 320

Glu Asn Ala Leu Thr Gly Thr Thr Thr Glu Met Asp Asp Ala Ser Glu
                325                 330                 335

Ala Asn Met Glu Leu Leu Val Gln Val Gly Glu Asn Leu Leu Lys Lys
            340                 345                 350

Pro Val Ser Glu Asp Asn Pro Glu Thr Tyr Glu Glu Ala Leu Lys Arg
            355                 360                 365

Phe Ala Lys Leu Leu Ser Asp Arg Lys Lys Leu Arg Ala Asn Lys Ala
        370                 375                 380

Ser Tyr
385
```

-continued

```
<210> SEQ ID NO 40
<211> LENGTH: 452
<212> TYPE: PRT
<213> ORGANISM: synthetic
<220> FEATURE:
<221> NAME/KEY: Protein
<222> LOCATION: (1)..(452)
<223> OTHER INFORMATION: Pre-cleavage patatin protein produced in Pichia
      pastoris

<400> SEQUENCE: 40

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Lys Glu Glu Gly Val
65                  70                  75                  80

Ser Leu Glu Lys Arg Glu Ala Glu Ala Gln Leu Gly Glu Met Val Thr
                85                  90                  95

Val Leu Ser Ile Asp Gly Gly Ile Arg Gly Ile Ile Pro Ala Thr
            100                 105                 110

Ile Leu Glu Phe Leu Glu Gly Gln Leu Gln Glu Met Asp Asn Asn Ala
        115                 120                 125

Asp Ala Arg Leu Ala Asp Tyr Phe Asp Val Ile Gly Gly Thr Ser Thr
    130                 135                 140

Gly Gly Leu Leu Thr Ala Met Ile Ser Thr Pro Asn Glu Asn Asn Arg
145                 150                 155                 160

Pro Phe Ala Ala Ala Lys Glu Ile Val Pro Phe Tyr Phe Glu His Gly
                165                 170                 175

Pro Gln Ile Phe Asn Pro Ser Gly Gln Ile Leu Gly Pro Lys Tyr Asp
            180                 185                 190

Gly Lys Tyr Leu Met Gln Val Leu Gln Glu Lys Leu Gly Glu Thr Arg
        195                 200                 205

Val His Gln Ala Leu Thr Glu Val Val Ile Ser Ser Phe Asp Ile Lys
    210                 215                 220

Thr Asn Lys Pro Val Ile Phe Thr Lys Ser Asn Leu Ala Asn Ser Pro
225                 230                 235                 240

Glu Leu Asp Ala Lys Met Tyr Asp Ile Ser Tyr Ser Thr Ala Ala Ala
                245                 250                 255

Pro Thr Tyr Phe Pro Pro His Tyr Phe Val Thr Asn Thr Ser Asn Gly
            260                 265                 270

Asp Glu Tyr Glu Phe Asn Leu Val Asp Gly Ala Val Ala Thr Val Ala
        275                 280                 285

Asp Pro Ala Leu Leu Ser Ile Ser Val Ala Thr Arg Leu Ala Gln Lys
    290                 295                 300

Asp Pro Ala Phe Ala Ser Ile Arg Ser Leu Asn Tyr Lys Lys Met Leu
305                 310                 315                 320

Leu Leu Ser Leu Gly Thr Gly Thr Thr Ser Glu Phe Asp Lys Thr Tyr
                325                 330                 335

Thr Ala Lys Glu Ala Ala Thr Thr Ala Val His Trp Met Leu Val
            340                 345                 350
```

```
Ile Gln Lys Met Thr Asp Ala Ala Ser Ser Tyr Met Thr Asp Tyr Tyr
            355                 360                 365

Leu Ser Thr Ala Phe Gln Ala Leu Asp Ser Lys Asn Asn Tyr Leu Arg
        370                 375                 380

Val Gln Glu Asn Ala Leu Thr Gly Thr Thr Thr Glu Met Asp Asp Ala
385                 390                 395                 400

Ser Glu Ala Asn Met Glu Leu Leu Val Gln Val Gly Glu Asn Leu Leu
                405                 410                 415

Lys Lys Pro Val Ser Glu Asp Asn Pro Glu Thr Tyr Glu Glu Ala Leu
            420                 425                 430

Lys Arg Phe Ala Lys Leu Leu Ser Asp Arg Lys Lys Leu Arg Ala Asn
        435                 440                 445

Lys Ala Ser Tyr
    450
```

<210> SEQ ID NO 41
<211> LENGTH: 367
<212> TYPE: PRT
<213> ORGANISM: synthetic
<220> FEATURE:
<221> NAME/KEY: Protein
<222> LOCATION: (1)..(367)
<223> OTHER INFORMATION: Post-cleavage patatin protein produced in
      Pichia pastoris

<400> SEQUENCE: 41

```
Glu Ala Glu Ala Gln Leu Gly Glu Met Val Thr Val Leu Ser Ile Asp
1               5                   10                  15

Gly Gly Gly Ile Arg Gly Ile Ile Pro Ala Thr Ile Leu Glu Phe Leu
            20                  25                  30

Glu Gly Gln Leu Gln Glu Met Asp Asn Asn Ala Asp Ala Arg Leu Ala
        35                  40                  45

Asp Tyr Phe Asp Val Ile Gly Thr Ser Thr Gly Gly Leu Leu Thr
    50                  55                  60

Ala Met Ile Ser Thr Pro Asn Gly Asn Asn Arg Pro Phe Ala Ala Ala
65                  70                  75                  80

Lys Glu Ile Val Pro Phe Tyr Phe Glu His Gly Pro Gln Ile Phe Asn
                85                  90                  95

Pro Ser Gly Gln Ile Leu Gly Pro Lys Tyr Asp Gly Lys Tyr Leu Met
            100                 105                 110

Gln Val Leu Gln Glu Lys Leu Gly Glu Thr Arg Val His Gln Ala Leu
        115                 120                 125

Thr Glu Val Val Ile Ser Ser Phe Asp Ile Lys Thr Asn Lys Pro Val
130                 135                 140

Ile Phe Thr Lys Ser Asn Leu Ala Asn Ser Pro Glu Leu Asp Ala Lys
145                 150                 155                 160

Met Tyr Asp Ile Ser Tyr Ser Thr Ala Ala Pro Thr Tyr Phe Pro
                165                 170                 175

Pro His Tyr Phe Val Thr Asn Thr Ser Asn Gly Asp Glu Tyr Glu Phe
            180                 185                 190

Asn Leu Val Asp Gly Ala Val Ala Thr Val Ala Asp Pro Ala Leu Leu
        195                 200                 205

Ser Ile Ser Val Ala Thr Arg Leu Ala Gln Lys Asp Pro Ala Phe Ala
    210                 215                 220

Ser Ile Arg Ser Leu Asn Tyr Lys Lys Met Leu Leu Leu Ser Leu Gly
225                 230                 235                 240
```

```
Thr Gly Thr Thr Ser Glu Phe Asp Lys Thr Tyr Thr Ala Lys Glu Ala
                245                 250                 255

Ala Thr Trp Thr Ala Val His Trp Met Leu Val Ile Gln Lys Met Thr
            260                 265                 270

Asp Ala Ala Ser Ser Tyr Met Thr Asp Tyr Tyr Leu Ser Thr Ala Phe
        275                 280                 285

Gln Ala Leu Asp Ser Lys Asn Asn Tyr Leu Arg Val Gln Glu Asn Ala
    290                 295                 300

Leu Thr Gly Thr Thr Thr Glu Met Asp Asp Ala Ser Glu Ala Asn Met
305                 310                 315                 320

Glu Leu Leu Val Gln Val Gly Glu Asn Leu Leu Lys Lys Pro Val Ser
                325                 330                 335

Glu Asp Asn Pro Glu Thr Tyr Glu Glu Ala Leu Lys Arg Phe Ala Lys
                340                 345                 350

Leu Leu Ser Asp Arg Lys Lys Leu Arg Ala Asn Lys Ala Ser Tyr
                355                 360                 365

<210> SEQ ID NO 42
<211> LENGTH: 7
<212> TYPE: PRT
<213> ORGANISM: synthetic
<220> FEATURE:
<221> NAME/KEY: Protein
<222> LOCATION: (1)..(7)
<223> OTHER INFORMATION: Xaa3 = Phe, Ile, or Leu; Xaa5 = His or Asn

<400> SEQUENCE: 42

Phe Tyr Xaa Glu Xaa Gly Pro
1               5

<210> SEQ ID NO 43
<211> LENGTH: 55
<212> TYPE: DNA
<213> ORGANISM: synthetic
<220> FEATURE:
<221> NAME/KEY: DNA
<222> LOCATION: (1)..(55)
<223> OTHER INFORMATION: oligonucleotide-3

<400> SEQUENCE: 43
ggagctcgag aaaagagagg ctgaagcttc attgaattac aaaaaaatgc tgttg        55

<210> SEQ ID NO 44
<211> LENGTH: 42
<212> TYPE: DNA
<213> ORGANISM: synthetic
<220> FEATURE:
<221> NAME/KEY: DNA
<222> LOCATION: (1)..(42)
<223> OTHER INFORMATION: oligonucleotide-4

<400> SEQUENCE: 44
tcccaactgt cctggtccat aagaagcttt gtttgctcgg ag                      42

<210> SEQ ID NO 45
<211> LENGTH: 36
<212> TYPE: DNA
<213> ORGANISM: synthetic
<220> FEATURE:
<221> NAME/KEY: DNA
<222> LOCATION: (1)..(36)
<223> OTHER INFORMATION: oligonucleotide-5

<400> SEQUENCE: 45
```
gcttcttatg gaccaggaca gttgggagaa atggtg                36

<210> SEQ ID NO 46
<211> LENGTH: 39
<212> TYPE: DNA
<213> ORGANISM: synthetic
<220> FEATURE:
<221> NAME/KEY: DNA
<222> LOCATION: (1)..(39)
<223> OTHER INFORMATION: oligonucleotide-6

<400> SEQUENCE: 46
ggtctagagg aattctcatt acctaattga agcaaatgc            39

<210> SEQ ID NO 47
<211> LENGTH: 39
<212> TYPE: DNA
<213> ORGANISM: synthetic
<220> FEATURE:
<221> NAME/KEY: DNA
<222> LOCATION: (1)..(39)
<223> OTHER INFORMATION: oligonucleotide-7

<400> SEQUENCE: 47
ggtctagagg aattctcatt aagtaacaaa gtaatgcgg            39

<210> SEQ ID NO 48
<211> LENGTH: 55
<212> TYPE: DNA
<213> ORGANISM: synthetic
<220> FEATURE:
<221> NAME/KEY: DNA
<222> LOCATION: (1)..(55)
<223> OTHER INFORMATION: oligonucleotide-8

<400> SEQUENCE: 48
ggagctcgag aaaagagagg ctgaagctaa tactagtaat ggagatgaat atgag   55

<210> SEQ ID NO 49
<211> LENGTH: 55
<212> TYPE: DNA
<213> ORGANISM: synthetic
<220> FEATURE:
<221> NAME/KEY: DNA
<222> LOCATION: (1)..(55)
<223> OTHER INFORMATION: oligonucleotide-9

<400> SEQUENCE: 49
ggagctcgag aaaagagagg ctgaagctag ttattccaca gcagcagctc caaca   55

<210> SEQ ID NO 50
<211> LENGTH: 39
<212> TYPE: DNA
<213> ORGANISM: synthetic
<220> FEATURE:
<221> NAME/KEY: DNA
<222> LOCATION: (1)..(39)
<223> OTHER INFORMATION: oligonucleotide-10

<400> SEQUENCE: 50
ggtctagagg aattctcatt atatgtcata catcttagc            39

<210> SEQ ID NO 51
<211> LENGTH: 55
<212> TYPE: DNA
<213> ORGANISM: synthetic
<220> FEATURE:
<221> NAME/KEY: DNA
<222> LOCATION: (1)..(55)
<223> OTHER INFORMATION: oligonucleotide-11

<400> SEQUENCE: 51
ggagctcgag aaaagagagg ctgaagctac atatacagca aaagaggcag ctacc    55

<210> SEQ ID NO 52
<211> LENGTH: 39
<212> TYPE: DNA
<213> ORGANISM: synthetic
<220> FEATURE:
<221> NAME/KEY: DNA
<222> LOCATION: (1)..(39)
<223> OTHER INFORMATION: oligonucleotide-12

<400> SEQUENCE: 52
ggtctagagg aattctcatt atttatcaaa ctctgaagt    39

<210> SEQ ID NO 53
<211> LENGTH: 55
<212> TYPE: DNA
<213> ORGANISM: synthetic
<220> FEATURE:
<221> NAME/KEY: DNA
<222> LOCATION: (1)..(55)
<223> OTHER INFORMATION: oligonucleotide-13

<400> SEQUENCE: 53
ggagctcgag aaaagagagg ctgaagctaa tgcattaaca ggcacaacta ctgaa    55

<210> SEQ ID NO 54
<211> LENGTH: 39
<212> TYPE: DNA
<213> ORGANISM: synthetic
<220> FEATURE:
<221> NAME/KEY: DNA
<222> LOCATION: (1)..(39)
<223> OTHER INFORMATION: oligonucleotide-14

<400> SEQUENCE: 54
ggtctagagg aattctcatt attcttgaac cctgaggta    39

<210> SEQ ID NO 55
<211> LENGTH: 55
<212> TYPE: DNA
<213> ORGANISM: synthetic
<220> FEATURE:
<221> NAME/KEY: DNA
<222> LOCATION: (1)..(55)
<223> OTHER INFORMATION: oligonucleotide-15

<400> SEQUENCE: 55
ggagctcgag aaaagagagg ctgaagctag cctcaactac aagaagatgc tgctg    55

<210> SEQ ID NO 56
<211> LENGTH: 42
<212> TYPE: DNA
<213> ORGANISM: synthetic
<220> FEATURE:
<221> NAME/KEY: DNA
<222> LOCATION: (1)..(42)
<223> OTHER INFORMATION: oligonucleotide-16

<400> SEQUENCE: 56
gccgagctgt cctggtccgt agctggcctt gttagcgcgg ag    42

<210> SEQ ID NO 57

```
<211> LENGTH: 36
<212> TYPE: DNA
<213> ORGANISM: synthetic
<220> FEATURE:
<221> NAME/KEY: DNA
<222> LOCATION: (1)..(36)
<223> OTHER INFORMATION: oligonucleotide-17

<400> SEQUENCE: 57
gccagctacg gaccaggaca gctcggcgag atggtg                         36

<210> SEQ ID NO 58
<211> LENGTH: 39
<212> TYPE: DNA
<213> ORGANISM: synthetic
<220> FEATURE:
<221> NAME/KEY: DNA
<222> LOCATION: (1)..(39)
<223> OTHER INFORMATION: oligonucleotide-18

<400> SEQUENCE: 58
ggtctagagg aattctcatt acctaatgct agcgaaggc                      39

<210> SEQ ID NO 59
<211> LENGTH: 55
<212> TYPE: DNA
<213> ORGANISM: synthetic
<220> FEATURE:
<221> NAME/KEY: DNA
<222> LOCATION: (1)..(55)
<223> OTHER INFORMATION: oligonucleotide-19

<400> SEQUENCE: 59
ggagctcgag aaaagagagg ctgaagctac tgccaaggag gccgctacct ggacc    55

<210> SEQ ID NO 60
<211> LENGTH: 39
<212> TYPE: DNA
<213> ORGANISM: synthetic
<220> FEATURE:
<221> NAME/KEY: DNA
<222> LOCATION: (1)..(39)
<223> OTHER INFORMATION: oligonucleotide-20

<400> SEQUENCE: 60
ggtctagagg aattctcatt acttgtcgaa ctcggaggt                      39
```

INSECT INHIBITORY LIPID ACYL HYDROLASES

CROSS REFERENCE TO RELATED APPLICATIONS

This application is related to U.S. Provisional Applications Serial No. 60/174,669 filed Jan. 6, 2000 and 60/219,912 filed Jul. 21, 2000, and claims the benefit of priority thereto.

FIELD OF THE INVENTION

The invention relates to the design, preparation, and use of patatin and structurally related proteins which have insect inhibitory properties and which display a requirement for catalysis structured around an active site catalytic dyad. Patatin and related proteins include amino acid sequence variants which maintain the active site catalytic dyad motif and which maintain insect inhibitory properties no less than the native protein, and include permuteins which have had their amino acid sequences rearranged at at least one breakpoint.

BACKGROUND OF THE INVENTION

The use of natural products, including proteins, is a well known method of controlling many insect, fungal, viral, bacterial, and nematode pathogens. For example, 67-endotoxin proteins of *Bacillus thringiensis* (*B.t.*) are used to control both lepidopteran and coleopteran insect pests. Genes producing these proteins have been introduced into and expressed by various plants, including cotton, tobacco, corn, wheat, rice, potato, and tomato, a number of different varieties of forage and turf grasses, ornamental flowers, and other fruit and vegetable crops. There are, however, several economically important insect pests that are not particularly susceptible to *B.t.* endotoxins. Examples of such important pests are the boll weevil (BWV), *Anthonomus grandis*, and corn rootworm (CRW), Diabrotica spp. In addition, having other, different gene products which do not function like *Bt* proteins for control of insects which are susceptible to *B.t.* endotoxins is important, if not vital, for effective and long term resistance management practices.

Recently, alternative species of bacteria have been identified which are capable of producing proteins displaying insect inhibitory effects. Photorhabdus and Xenorhabdus comprise broad genus' of bacteria which occupy the gut of entomopathogenic nematodes. upon invasion of the insect body by the nematode, the entomopathogenic bacteria are released from the gut of the nematode into the insect haemolymph where they proliferate, inhibit further development of the insect, and produce a nutrient enriched monoculture designed specifically for symbiotic nematode and bacterial survival. A variety of extracellular proteins are produced by these bacterial symbionts, each insect inhibitory protein having distinct insect genus and species specificity, each protein likely being structurally and probably functionally different from BT ICP's. (Ensign et al., Insecticidal Protein Toxins from Photorhabdus, WO 97/17432; Jarrett et al., Pesticidal Agents, WO 98/08388; Ffrench-Constant et al., Novel insecticidal Toxins from Nematode-Symbiotic Bacteria, Cellular and Molecular Life Sciences 57:828–833, May 2000).

Plant proteins have also been identified which exhibit insect inhibitory effects. One such protein is patatin, a non-specific lipid acyl hydrolase, which is the major storage protein of potato tubers (Gaillaird, T., *Biochem. J.* 121: 379–390, 1971; Racusen, D., *Can. J. Bot.*, 62: 1640–1644, 1984; Andrews, D. L., et al., *Biochem. J.*, 252: 199–206, 1988). Patatin has been shown to control various insects, including western rootworm (WCRW, *Diabrotica virigifera*), southern corn rootworm (SCRW, *Diabrotica undecimpunctata*), and boll weevil (BWV, *Anthonomus grandis*) (U.S. Pat. No. 5,743,477, issued Apr. 28, 1998). Patatin related protein sequences have been identified in a variety of plant species. When applied at an appropriate level in artificial diet, potato patatin is lethal to some larvae and will stunt the growth of survivors so that maturation is prevented or severely delayed, resulting in no reproduction. These proteins display non-specific lipid acyl hydrolase activity. Studies have shown that the enzyme activity is essential for its insect inhibitory activity (Strickland, J. A., et al., *Plant Physiol.*, 109: 667–674, 1995). Patatins may be applied directly to the plants or introduced in other ways well known in the art, such as through the application of plant-colonizing microorganisms, which have been transformed to produce the enzymes, or by the plants themselves after similar transformation.

In potato, the patatins are found predominantly in tubers, but also at much lower levels in other plant organs (Hofgen, R. and Willmitzer, L., *Plant Science*, 66: 221–230, 1990). Genes that encode patatins have been previously isolated by Mignery, G. A., et al. (*Nucleic Acids Research*, 12: 7987–8000, 1984; Mignery, G. A., et al., *Gene*, 62: 27–44, 1988; Stiekema, et al., *Plant Mol. Biol.*, 11: 255–269, 1988) and others. Patatins are found in other plants, particularly solanaceous species (Ganal, et al., *Mol. Gen. Genetics*, 225: 501–509, 1991; Vancanneyt, et al., *Plant Cell*, 1: 533–540, 1989) and recently *Zea mays* (Patent number WO 96/37615). Rosahl, et al. (*EMBO J.*, 6: 1155–1159, 1987) transferred a patatin coding sequence into tobacco plants, and observed expression of patatin, demonstrating that patatin can be heterologously expressed by plants. Modification of coding sequences has been demonstrated to improve expression of other insect inhibitory protein genes such as the δ-endotoxin sequences from *Bacillus thringiensis* (Fischhoff and Perlak; WO 93/07278). However, expression of a native plant species sequence encoding a protein exhibiting insect inhibitory properties in a plant at levels not previously observed in nature would be particularly advantageous. Such sequences would not require coding sequence modifications found to be necessary to achieve substantial levels of insect protection as have been required for sequences encoding *Bt* proteins for example.

As indicated above, plant non-specific lipid acyl hydrolases have been identified from a variety of plant sources including potato tubers. Speculation on the role of the enzyme has been centered on their involvement in the turnover of membrane lipids, however one report identified an serine residue required for hydrolase activity and conserved sequence flanking the residue in potato patatin based on inactivation of the enzyme acyl lipid hydrolase activity when treated with diisopropyl fluorophosphate and an amino acid sequence alignment with a patatin isoform (Walsh et al., U.S. Pat. No. 5,743,477; Apr. 28, 1998). Based on the amino acid sequence of potato patatin, Walsh et al. proposed that Ser-77 in the hydrolase motif, Gly-X-Ser-X-Gly is the catalytic residue required for enzyme function as well as insect inhibitory activity.

The inventors herein have identified a patatin isozyme designated Pat17, and used alanine scanning mutagenesis and X-ray crystallography to solve the structure of the patatin enzyme and to identify additional residues responsible for both catalytic activity and insect inhibitory bioactivity.

Novel proteins generated by the method of sequence transposition resembles that of naturally occurring pairs of proteins that are related by linear reorganization of their amino acid sequences (Cunningham, et al. *Proc. Natl. Sci., U.S.A.*, 76: 3218–3222, 1979; Teather, et al., *J. Bacteriol.*, 172: 3837–3841, 1990; Schimming, et al., *Eur. J. Biochem.*, 204: 13–19, 1992; Yamiuchi, et al., *FEBS Lett.*, 260: 127–130, 1991; MacGregor, et al., *FEBS. Lett.*, 378: 263–266, 1996). The first in vitro application of sequence rearrangement to proteins was described by Goldenberg and Creighton (Goldenberg and Creighton, *J. Mol. Biol.*, 165: 407–413, 1983). A new N-terminus is selected at an internal site (breakpoint) of the original sequence, the new sequence having the same order of amino acids as the original from the breakpoint until it reaches an amino acid that is at or near the original C-terminus. At this point the new sequence is joined, either directly or through an additional portion or sequence (linker), to an amino acid that is at or near the original N-terminus, and the new sequence continues with the same sequence as the original until it reaches a point that is at or near at or near the amino acid that was N-terminal to the breakpoint site of the original sequence, this residue forming the new C-terminus of the chain. This approach has been applied to proteins which range in size from 58 to 462 amino acids and represent a broad range of structural classes (Goldenberg and Creighton, *J. Mol. Biol.*, 165: 407–413, 1983; Li and Coffino, *Mol. Cell. Biol.*, 13: 2377–2383, 1993; Zhang, et al., *Nature Struct. Biol.*, 1: 434–438, 1995; Buchwalder, et al., *Biochemistry*, 31: 1621–1630, 1994; Protasova, et al., *Prot. Eng.*, 7: 1373–1377, 1995; Mullins, et al., *J. Am. Chem. Soc.*, 116: 5529–5533, 1994; Garrett, et al., *Protein Science*, 5: 204–211, 1996; Hahn, et al., *Proc. Natl. Acad. Sci. U.S.A.*, 91: 10417–10421, 1994; Yang and Schachman, *Proc. Natl. Acad. Sci. U.S.A.*, 90: 11980–11984, 1993; Luger, et al., *Science*, 243: 206–210, 1989; Luger, et al., *Prot. Eng.*, 3: 249–258, 1990; Lin, et al., *Protein Science*, 4: 159–166, 1995; Vignais, et al., *Protein Science*, 4: 994–1000, 1995; Ritco-Vonsovici, et al., *Biochemistry*, 34: 16543–16551, 1995; Horlick, et al., *Protein Eng.*, 5: 427–431, 1992; Kreitman, et al., *Cytokine*, 7: 311–318, 1995; Viguera, et al., *Mol. Biol.*, 247: 670–681, 1995; Koebnik and Kramer, *J. Mol. Biol.*, 250: 617–626, 1995; Kreitman, et al., *Proc. Natl. Acad. Sci.*, 91: 6889–6893, 1994).

Thus, there exists a need to identify novel protein sequences which are insect inhibitory, which are not related to *Bt* insect inhibitory proteins in form or function, and which are safe for expression in human and animal food supplies. Such proteins should have modes of action distinct from those of *Bt* insect inhibitory proteins or Xenorhabdus or Photorhabdus insect inhibitory proteins and should act synergistically with *BT's* or Xenorhabdus or Photorhabdus insect inhibitory proteins to aid in preventing the onset of insect species resistance developed in response to providing only single insect inhibitory proteins in compositions of matter as food sources to populations of insects in fields of recombinant crops.

SUMMARY OF THE INVENTION

The present invention provides a method for identifying a lipid acyl hydrolase having insect inhibitory properties comprising isolating and purifying a protein having lipid acyl hydrolase activity; obtaining a three dimensional crystal structure of said protein; and identifying the amino acid sequence of said protein; wherein said amino acid sequence contains a serine active site motif gly-xxx-ser-xxx-gly (SEQ ID NO:14), and an aspartate active site motif glu-xxx-xxx-leu-val-asp-gly (SEQ ID NO:15). Modifications of these motifs should disrupt the hydrolase and the insect inhibitory properties of the protein.

Furthermore, the invention provides a method of inhibiting insect infestation of a plant or plant part comprising providing in the insect's plant diet an insect inhibitory effective amount of a lipid acyl hydrolase having insect inhibitory properties when ingested by said insect, wherein the amino acid sequence of said hydrolase comprises a serine active site motif gly-xxx-ser-xxx-gly (SEQ ID NO:14) and an aspartate active site motif glu-xxx-xxx-leu-val-asp-gly (SEQ ID NO:15). The serine active site motif can be shown to be required by treating the hydrolase with a substrate which binds specifically and irreversibly to the serine in the serine active site motif, such as diisopropyl fluorophosphate. The serine active site motif and/or the aspartate active site motif can be shown to be required by modifying the amino acid sequence within each motif to show loss of function of hydrolase and insect inhibition.

The invention further provides a method for protecting a plant or part thereof against insect infestation comprising providing an insect controlling amount of a plant lipid acyl hydrolase protein having a crystal structure containing a serine active site motif G-X-S-X-G (SEQ ID NO:14) and an aspartate active site motif E-X-X-L-V-D-G, (SEQ ID NO:15) each motif being present in the active site cleft defined by the crystal structure and the serine and aspartate residues in each motif being required for the catalytic function of the hydrolase, and the catalytic function of the hydrolase being required for functional and effective insect inhibition when provided in diet form to a susceptible insect larvae.

Novel protein sequences having lipid acyl hydrolase activity, as well as nucleic acid sequences encoding said protein sequences are disclosed. The proteins maintain desirable insect inhibitory properties when expressed in plants.

Alanine scanning and 'rational substitution' is performed on identified peptide sequences to determine specific amino acids which contribute to lipid acyl hydrolase activity. Individual mutations are introduced into the whole protein sequence by methods such as site directed mutagenesis of the encoding nucleic acid sequence.

Permuteins of the novel protein sequences may be constructed to reduce or eliminate allergenic properties or to improve protein stability and protein expression. The encoding nucleic acid sequence is modified to produce a protein with a rearranged amino acid sequence, while maintaining insect inhibitory properties.

The novel proteins may be used in controlling insects, as nutritional supplements, in immunotherapy protocols, and in other potential applications. Transgenic plant cells and plants containing the encoding nucleic acid sequence may be particularly beneficial in the control of insects, and as a nutritional/immunotherapy material.

One object of the present invention is to provide a method for protecting a plant or plant part from insect infestation.

Another object of the present invention is to provide a method for identifying a lipid acyl hydrolase enzyme which functions to inhibit insect infestation. The method consists of identifying a protein displaying lipid acyl hydrolase activity. A DNA sequence encoding the protein sequence can either be synthesized by back-translating the amino acid sequence, or by identifying a DNA coding sequence from a source from which the enzyme was isolated and purified. The enzyme can be treated with diisopropyl fluorophosphate to identify a serine residue involved in lipid acyl hydrolase activity. The crystal structure of the enzyme can then be determined, and the three dimensional model of the structure can be used to identify the active site and additional residues involved in active site catalysis. Other residues, such as His109 exemplified in Pat17, can be identified which are crucial for enzyme stability using alanine scanning mutagenesis. An enzyme displaying lipid acyl hydrolase activity which requires serine active site functionality and at least one additional amino acid residue interacting with the active site serine is expected to have insect inhibitory bioactivity which can be determined by placing an insect inhibitory amount of the native protein sequence into a bioassay with a susceptible insect to determine insect inhibitory bioactivity. A native protein, mutagenized to inactivate one or more of the residues involved in active site lipid acyl hydrolase activity can be used in a separate bioassay to confirm the related active site residue involvement in insect inhibitory bioactivity.

A further object of the present invention is to provide compositions which protect a plant or a plant part from insect infestation by one or more of insects selected from the group consisting of corn rootworm, cutworm, wire worm earworm, aphids, piercing and sucking insects, borers, army worms, and potato beetles.

A further object of the present invention is to provide a method for constructing transformed plant cells comprising a DNA sequence encoding a novel lipid acyl hydrolase having insect inhibitory bioactivity, wherein the hydrolase and insect inhibitory activity are identified by first treating the hydrolase with diisopropyl fluorophosphate to identify at least one serine residue involved in lipid acyl hydrolase activity; second determining the crystal structure of the hydrolase and forming a three dimensional model of the hydrolase; and third, using the three dimensional model of the structure to identify additional residues involved in active site catalysis; wherein the transformed plant cells are resistant to insect infestation or inhibit insects upon ingestion of said transformed plant cells. Using alanine scanning mutagenesis, other residues can be identified which are crucial for hydrolase enzyme stability. An enzyme displaying lipid acyl hydrolase activity which requires serine active site functionality and at least one additional amino acid residue interacting with the active site serine is expected to have insect inhibitory bioactivity which can be determined by placing an insect inhibitory amount of cells expressing the native protein sequence into a bioassay with a susceptible insect to determine insect inhibitory bioactivity. A native protein, mutagenized to inactivate one or more of the residues involved in active site lipid acyl hydrolase activity can be used in a separate bioassay to confirm the related active site residue involvement in insect inhibitory bioactivity.

Another aspect of the present invention is directed to providing an insect inhibitory composition which prevents or delays the development of insect resistance to an insect inhibitory compound in a field of crops. The composition contains two or more insect inhibitory components, each component being present in an amount sufficient to inhibit the same insect species, at least one of the components being a novel lipid acyl hydrolase having insect inhibitory bioactivity, wherein the hydrolase and insect inhibitory activity are identified by first treating the hydrolase with diisopropyl fluorophosphate to identify a serine residue involved in lipid acyl hydrolase activity; second determining the crystal structure of the hydrolase and forming a three dimensional model of the hydrolase; and third, using the three dimensional model of the structure to identify additional residues involved in active site catalysis; wherein the composition insect infestation or inhibit insects upon ingestion of said transformed plant cells.

An additional aspect of the present invention comprises applying an insect inhibitory effective amount of a protein sequence displaying lipid acyl hydrolase activity to a plant or incorporating said amount into said plant, wherein said protein sequence displaying lipid acyl hydrolase activity, comprises a first peptide sequence comprising Gly-$Xxx_1$-Ser-$Xxx_2$-Gly, (SEQ ID NO:14) and a second peptide sequence comprising Glu-$Xxx_3$-$Xxx_4$-Leu-Val-Asp-Gly (SEQ ID NO:15). $Xxx_1$ or $Xxx_2$ can be threonine or any other amino acid which is structurally and functionally similar to threonine. $Xxx_3$ can be an aromatic amino acid residue, or preferably tyrosine or phenylalanine. $Xxx_4$ can be an amino acid residue considered in the art to be a base, preferably asparagine or histidine. A catalytic active site structure utilizing a serine-aspartate dyad chemistry is supported by the requirement for both peptide sequences being present, along with three dimensional modeling based on crystal structure of the protein sequence, and a pH rate profile indicating that a single residue with a pKa of less than about 5 must be deprotonated to show hydrolase activity and insect inhibitory bioactivity.

DESCRIPTION OF THE FIGURES

The following figures form part of the present specification and are included to further demonstrate certain aspects of the present invention. The invention may be better understood by reference to one or more of these drawings in combination with the detailed description of specific embodiments presented herein.

FIG. 1 illustrates the cDNA and amino acid sequence translation of a native patatin isoform designated as Pat17

FIG. 2 illustrates the hydrolase activity of the alanine scanning variant isoforms of Pat17

FIG. 3 illustrates the pH rate profile for the native Pat17 enzyme

FIG. 4 illustrates the effect of Pat17 and variants on growth of neonate SCRW larvae FIG. 5 illustrates the effect of wild type and H109N variant Pat17 on growth of neonate SCRW larvae FIG. 6 illustrates (a) a ribbon diagram of the Pat17 structure based on X-ray crystallography solution analysis; and (b) a ribbon diagram of the proposed Pat17 active site showing the catalytic serine and aspartate residues FIG. 7 illustrates a ribbon diagram of the Pat17 structure around a histidine at position 109

FIG. 8 illustrates the proposed catalytic mechanism of Pat17 involving serine and aspartate catalytic active site residues in a catalytic dyad FIG. 9 illustrates the alignment of Pat17 with other dicot patatin or patatin related amino acid sequences, and alignment with several monocot patatin related sequences, displaying the conserved catalytic serine motif and catalytic aspartate motif alignments and sequence conservations.

FIG. 10 illustrates construction of nucleic acid sequences encoding patatin permutein proteins, and for illustrative purposes a breakpoint at position 247 is shown.

DESCRIPTION OF THE SEQUENCE LISTINGS

The following description of the sequence listing forms part of the present specification and is included to further demonstrate certain aspects of the present invention. The invention can be better understood by reference to one or more of these sequences in combination with the detailed description of specific embodiments presented herein.

| | |
|---|---|
| SEQ ID NO: 1 | patatin homolog Pat17 amino acid sequence (*Solanum cardiophyllum*) |
| SEQ ID NO: 2 | patatin isozyme PatFm (mature protein lacking signal peptide) |
| SEQ ID NO: 3 | Patatin isozyme PatIm (mature protein lacking signal peptide) |
| SEQ ID NO: 4 | Patatin isozyme PatL+ (including signal peptide) |
| SEQ ID NO: 5 | Patatin isozyme PatA+ (including signal peptide) |
| SEQ ID NO: 6 | Patatin isozyme PatB+ (including signal peptide) |
| SEQ ID NO: 7 | patatin homolog pentin 1 (*Pentaclethra macroloba*) |
| SEQ ID NO: 8 | monocot patatin homolog 5c9 (*Zea mays*) |
| SEQ ID NO: 9 | maize patatin homolog amino acid sequence corn1 |
| SEQ ID NO: 10 | maize patatin homolog amino acid sequence corn2 |
| SEQ ID NO: 11 | maize patatin homolog amino acid sequence corn3 |
| SEQ ID NO: 12 | maize patatin homolog amino acid sequence corn4 |
| SEQ ID NO: 13 | maize patatin homolog amino acid sequence corn5 |
| SEQ ID NO: 14 | Serine active site consensus sequence motif |
| SEQ ID NO: 15 | Aspartate active site consensus sequence motif |
| SEQ ID NO: 16 | linker sequence |
| SEQ ID NO: 17 | linker sequence |
| SEQ ID NO: 18 | oligonucleotide sequence |
| SEQ ID NO: 19 | oligonucleotide sequence |
| SEQ ID NO: 20 | pMON37402 sequence encoding permutein protein |
| SEQ ID NO: 21 | Permutein protein encoded from pMON37402 sequence |
| SEQ ID NO: 22 | pMON37405 sequence encoding permutein protein |
| SEQ ID NO: 23 | Permutein protein encoded by pMON37405 sequence |
| SEQ ID NO: 24 | pMON37406 sequence encoding permutein protein |
| SEQ ID NO: 25 | Permutein protein encoded by pMON37406 sequence |
| SEQ ID NO: 26 | pMON37407 sequence encoding permutein protein |
| SEQ ID NO: 27 | Permutein protein encoded by pMON37407 sequence |
| SEQ ID NO: 28 | pMON37408 sequence encoding permutein protein |
| SEQ ID NO: 29 | Permutein protein encoded by pMON37408 sequence |
| SEQ ID NO: 30 | pMON40701 sequence encoding permutein protein |
| SEQ ID NO: 31 | Permutein protein encoded by pMON40701 sequence |
| SEQ ID NO: 32 | pMON40703 sequence encoding permutein protein |
| SEQ ID NO: 33 | Permutein protein encoded by pMON40703 sequence |
| SEQ ID NO: 34 | pMON40705 sequence encoding permutein protein |
| SEQ ID NO: 35 | Permutein protein encoded by pMON40705 sequence |
| SEQ ID NO: 36 | corn homolog peptide |
| SEQ ID NO: 37 | patatin homolog Pat 17 nucleic acid coding sequence and amino acid translation (*Solanum cardiophyllum*) |
| SEQ ID NO: 38 | DNA sequence encoding a patatin (acyl lipid hydrolase) protein |
| SEQ ID NO: 39 | potato patatin protein sequence |
| SEQ ID NO: 40 | Pre-cleavage patatin protein produced in *Pichia pastoris* |
| SEQ ID NO: 41 | Post-cleavage patatin protein produced in *Pichia pastoris* |
| SEQ ID NO: 42 | Conserved Basic amino acid consensus motif F—Y-X1-E-H/N-G-P |
| SEQ ID NO: 43–60 | oligonucleotides |

DEFINITIONS

The following definitions are provided in order to aid those skilled in the art in understanding the detailed description of the present invention.

"Chimeric" refers to a fusion nucleic acid or protein sequence. A chimeric nucleic acid sequence is comprised of two sequences joined in-frame that encode a chimeric protein. The coding regions of multiple protein subunits may be joined in-frame to form a chimeric nucleic acid sequence that encodes a chimeric protein sequence.

"Coding sequence", "open reading frame", and "structural sequence" refer to the region of continuous sequential nucleic acid triplets encoding a protein, polypeptide, or peptide sequence.

"Codon" refers to a sequence of three nucleotides that specify a particular amino acid.

"Complementarity" refers to the specific binding of adenine to thymine (or uracil in RNA) and cytosine to guanine on opposite strands of DNA or RNA.

"Deallergenize" (render hypoallergenic) refers to the method of engineering or modifying a protein such that it has a reduced or eliminated ability to induce an allergic response. A deallergenized protein may be referred to as being hypoallergenic. The degree of deallergenization of a protein may be measured in vitro by the reduced binding of IgE antibodies.

"DNA sequence heterologous to the promoter region" means that the coding DNA sequence does not exist in nature in the same gene with the promoter to which it is now attached.

"DNA sequence" refers to a DNA molecule that has been isolated free of total genomic DNA of a particular species.

"Electroporation" refers to a method of introducing foreign DNA into cells that uses a brief, high voltage dc charge to permeabilize the host cells, causing them to take up extra-chromosomal, epi-genetic DNA, or any nucleotide or polynucleotide molecule provided exogeneously to the cells.

"Encoding DNA" refers to chromosomal DNA, plasmid DNA, cDNA, or synthetic DNA which encodes any of the enzymes or proteins discussed herein.

"Endogenous" refers to materials originating from within an organism or cell.

"Endonuclease" refers to an enzyme that hydrolyzes double stranded DNA at internal locations.

"Epitope" refers to a region on an allergen that interacts with the cells of the immune system. Epitopes are often further defined by the type of antibody or cell with which they interact, e.g. if the region reacts with B-cells or antibodies (IgE), it is called a B-cell epitope.

"Exogenous" refers to materials originating from outside of an organism or cell. This typically applies to nucleic acid molecules used in producing transformed or transgenic host cells and plants.

"Expressibly coupled", "expressibly linked", "operably linked", and "operatively linked", refer to a promoter or promoter region and a coding or structural sequence in such an orientation and distance that transcription of the coding or structural sequence may be directed by the promoter or promoter region. 3' transcription termination and polyadenylation sequences can also be operably linked to coding sequences.

"Expression" refers to the transcription of a gene to produce the corresponding mRNA and translation of this mRNA to produce the corresponding gene product, i.e., a peptide, polypeptide, or protein. Expression can also refer to the transcription of a gene coding for a tRNA or a structural, catalytic, or functional RNA molecule which is not otherwise subsequently translated into protein.

"Fusion modified gene" refers to a nucleic acid sequence of one origin fused to a nucleic acid sequence from another origin at either the N-termini or the C-termini, e.g. a nucleic acid sequence encoding an insecticidal protein or fragment from *B.t.* fused to the N- or C-termini to a nucleic acid sequence encoding patatin or a fragment of patatin or vice versa.

"Heterologous DNA" refers to DNA from a source different than that of the recipient cell.

"Homologous DNA" refers to DNA from the same source as that of the recipient cell.

"Identity" refers to the degree of similarity between two nucleic acid or protein sequences. An alignment of the two sequences is performed by a suitable computer program. A widely used and accepted computer program for performing sequence alignments is CLUSTALW v1.6 (Thompson, et al. *Nucl. Acids Res.*, 22: 4673–4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there were 100 matched amino acids between 200 and a 400 amino acid proteins, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity.

"IgE" (Immunoglobulin E) refers to a specific class of immunoglobulin secreted by B cells. IgE binds to specific receptors on Mast cells. Interaction of an allergen with mast cell-bound IgE may trigger allergic symptoms.

"Immunotherapy" refers to any type of treatment that targets the immune system. Allergy immunotherapy is a treatment in which a progressively increasing dose of an allergen is given in order to induce an immune response characterized by tolerance to the antigen/allergen, also known as desensitization.

"In vitro" refers to in the laboratory.

"In vivo" refers to in a living organism.

"Insect inhibitory polypeptide" refers to a polypeptide having properties that adversely affects the growth and development of insect pests. Insect inhibitory also refers to isolated nucleic acid molecules comprising nucleotide sequences encoding polypeptides or proteins exhibiting insect inhibitory activity, wherein said activity is manifested by inhibiting the growth or development of, or contributing substantially to, or causing the death of a Coleopteran, a Dipteran, a Lepidopteran, a Hemipteran, a Hymenopteran, or a sucking and piercing insect or insect larvae thereof. Insect inhibitory also includes nucleotide sequences encoding novel proteins comprising polypeptides which augment the activity of peptides exhibiting insect inhibitory activity when fed to Coleopteran, Dipteran, Lepidopteran, Hemipteran, Hymenopteran, or sucking and piercing insects or insect larvae thereof.

"Monocot" refers to plants having a single cotyledon (the first leaf of the embryo of seed plants); examples include cereals such as maize, rice, wheat, oats, and barley.

"Multiple cloning site" refers to an artificially constructed collection of restriction enzyme sites in a vector that facilitates insertion of foreign DNA into the vector.

"Mutation" refers to any change or alteration in the sequence of a gene. Several types exist, including point, frame shift, and splicing.

"Native" refers to two segments of nucleic acid naturally occurring in the same organism. For example, a native promoter is the promoter naturally found with a given gene in an organism.

"Naturally occurring" refers to a nucleic acid or protein which is found in nature, and has not been manipulated or altered by the hand of man.

"Non-naturally occurring" refers to a nucleic acid or protein which is not found in nature, but instead has been synthesized to exhibit properties that are otherwise found in nature. The synthesis of any such non-naturally occurring nucleic acid or protein does not necessarily require that the entire sequence of either be synthetically produced, but that only an insubstantial modification, such as a nucleotide substitution in a nucleic acid sequence or an amino acid substitution in the amino acid sequence of a protein, is all that is necessary to qualify the nucleic acid or protein as one which is non-naturally occurring.

"Nucleic acid segment" or "nucleic acid sequence" is a nucleic acid molecule that has been isolated free of total genomic DNA of a particular species, or that has been synthesized. Included with the term "nucleic acid segment" are DNA segments or DNA sequences, recombinant vectors, plasmids, cosmids, phagemids, phage, viruses, etcetera.

"Nucleic acid" refers to deoxyribonucleic acid (DNA) and ribonucleic acid (RNA).

Nucleic acid codes: A=adenosine; C=cytosine; G=guanosine; T=thymidine; N=equimolar A, C, G, and T; I=deoxyinosine; K=equimolar G and T; R=equimolar A and G; S=equimolar C and G; W=equimolar A and T; Y=equimolar C and T.

"Open reading frame (ORF)" refers to a region of DNA or RNA encoding a peptide, polypeptide, or protein.

"Plasmid" refers to a circular, extrachromosomal, self-replicating DNA.

"Point mutation" refers to an alteration of a single nucleotide in a nucleic acid sequence.

"Polymerase chain reaction (PCR)" or thermal amplification refers to an enzymatic technique to create multiple copies of one sequence of nucleic acid. Copies of DNA sequence are prepared by shuttling a DNA polymerase between two amplimers. The basis of this amplification method is multiple cycles of temperature changes to denature, then re-anneal amplimers, followed by extension to synthesize new DNA strands in the region located between the flanking amplimers.

"Probe" refers to a polynucleotide sequence which is complementary to a target polynucleotide sequence in the analyte.

"Promoter" or "promoter region" refers to a DNA sequence, usually found upstream of, or positioned 5' with reference to, a coding sequence, that controls expression of the coding sequence by controlling production of messenger RNA (mRNA) by providing the recognition site for RNA polymerase and/or other factors necessary for transcription initiation at the correct site. As contemplated herein, a promoter or promoter region includes variations of promoters derived by means of ligation to various regulatory sequences, random or controlled mutagenesis, and addition or duplication of enhancer sequences. The promoter regions disclosed herein, and biologically functional equivalents thereof, are responsible for driving the transcription of coding sequences under their control when introduced into a host as part of a suitable recombinant vector, as demonstrated by its ability to produce mRNA.

"Recombinant DNA construct" or "recombinant vector" refers to any agent such as a plasmid, cosmid, virus, autonomously replicating sequence, phage, or linear or circular single-stranded or double-stranded DNA or RNA nucleotide sequence, derived from any source, capable of genomic integration or autonomous replication, comprising a DNA molecule in which one or more DNA sequences have been linked in a functionally operative manner. Such recombinant DNA constructs or vectors are capable of introducing a 5' regulatory sequence or promoter region and a DNA sequence for a selected gene product into a cell in such a manner that the DNA sequence is transcribed into a functional mRNA which is translated and therefore expressed. Recombinant DNA constructs or recombinant vectors may be constructed to be capable of expressing antisense RNA's, in order to inhibit translation of a specific RNA of interest.

"Recombinant proteins", also referred to as "heterologous proteins", are proteins which are normally not produced by the host cell.

"Regeneration" refers to the process of growing a plant from a plant cell (e.g., plant protoplast or explant).

"Regulatory sequence" refers to a nucleotide sequence located upstream (5'), within, and/or downstream (3') to a DNA sequence encoding a selected gene product whose transcription and expression is controlled by the regulatory sequence in conjunction with the protein synthetic apparatus of the cell.

"Restriction enzyme" refers to an enzyme that recognizes a specific palindromic sequence of nucleotides in double stranded DNA and cleaves both strands; also called a restriction endonuclease. Cleavage typically occurs within the restriction site.

"Result-effective substitution" (RES) refers to an amino acid substitution within an IgE-binding region (epitope) of a protein (patatin) which reduces or eliminates the IgE binding by that epitope.

"Selectable marker" refers to a nucleic acid sequence whose expression confers a phenotype facilitating identification of cells containing the nucleic acid sequence. Selectable markers include those which confer resistance to toxic chemicals (e.g. ampicillin resistance, kanamycin resistance), complement a nutritional deficiency (e.g. an inability to produce any or produce sufficient compounds for survival without supplementation such as uracil, histidine, leucine, diaminopimelic acid, etc.), or impart a visually or optically distinguishing characteristic (e.g. color changes or fluorescence).

"Transcription" refers to the process of producing an RNA copy from a DNA template. Reverse transcription refers to the process of producing either an RNA copy from an RNA template, or a DNA copy from an RNA template.

"Transformation" refers to a process of introducing an exogenous nucleic acid sequence (e.g., a vector, recombinant nucleic acid molecule) into a cell or protoplast in which that exogenous nucleic acid is incorporated into a chromosome or into a naturally occurring heterologous DNA, such as into chloroplast DNA, or is capable of autonomous replication.

"Transformed cell" is a cell whose DNA has been altered by the introduction of an exogenous nucleic acid molecule into that cell.

"Transgenic cell" refers to any cell derived from or regenerated from a transformed cell or derived from a transgenic cell. Exemplary transgenic cells include plant calli derived from a transformed plant cell and particular cells such as leaf, root, stem, e.g., somatic cells, or reproductive (germ) cells obtained from a transgenic plant.

"Transgenic plant" refers to a plant or progeny thereof derived from a transformed plant cell or protoplast, wherein the plant DNA contains an introduced exogenous nucleic acid sequence not originally present in a native, non-transgenic plant of the same species. Alternatively, the plant DNA may contain the introduced nucleic acid sequence in a higher copy number than in the native, non-transgenic plant of the same species.

"Translation" refers to the production of protein from messenger RNA.

"Vector" refers to a plasmid, cosmid, bacteriophage, or virus that carries foreign DNA into a host organism.

"Western blot" refers to protein or proteins that have been separated by electrophoresis, transferred and immobilized onto a solid support, then probed with an antibody.

DETAILED DESCRIPTION OF THE INVENTION

The present invention is directed to the art areas of plant molecular biology, plant agriculture, and entomology as well as to protein chemistry, immunology, and protein crystallography.

Economically important crops have always been subject to insect infestation, at times resulting in devastating damage. Even when damage is not ultimately devastating, the insect pressure can significantly alter the yield and quality of the harvest. Means for controlling the insect pressure in a field of crops has been partially addressed by chemical applications as well as, to a lesser extent, traditional breeding methodologies. True to genetic variability, however, the insects seem to adapt readily to these traditional means for control. Naturally occurring plant traits which confer insect inhibitory advantages have evolved and been selected for by plant breeders over generations of breeding. These traits have either succumbed to, or are likely to ultimately succumb to races of insects which adapt to feed seemingly unaffected by the selected traits. Although such naturally selected plant derived traits are in fact useful, they are not altogether the most effective means of combating insect pressure for a number of reasons. First, the tolerances that plants can evolve are in constant flux with the changes that insects accrue in order to overcome the defenses. Second, and perhaps more importantly, the rate at which traditional breeding takes place is too slow and cumbersome to provide the types of resistance that are necessary to maintain the defenses for crop plants. In addition, other means have proven much more effective in conferring insect pressure control.

One such means is topical chemical treatment to susceptible plants. This has particular advantages because it can be applied only when insect pressure is detected, and only in amounts necessary to attempt to achieve control of the insect pressures. However, there are substantial disadvantages to chemical treatments. Primarily, most chemical applications utilize organophosphates or similar compositions which are not only toxic to the target insect pests but to all other insect, arachnid, mammalian or avian species present in the local environment to which the application is directed. Second, application of individual chemical compositions leads to rapid development of resistance to the composition. There has been good success in treating fields of crops, however, with compositions containing two or more chemical insecticides, at least one of which acts to inhibit, kill, or otherwise control at least the target insect pest using a mode of action different from the other pesticides present in the composition. This means also leads to virtually no development of resistance. A third disadvantage to using chemical treatments is that often the composition is wholly or partially non-biodegradable and therefore not a bio-efficacious means for treating crops in a field in which further use of the field for crop rotations is contemplated. In addition, another disadvantage to topical applications is that many insect pests are shielded from the topical effects of the treatments because of the nature of their life cycles. Insects such as grubs, borers, and leaf rollers con continue to feast uninhibited because of the nature of their chosen ecological niche. Therefore, alternative means of controlling insect pressures have been necessary.

Through the advent of molecular biology, recombinant plants expressing very effective insect control proteins have developed and recently deployed into commercial varieties which can now be obtained through seed providers. Such recombinant plants generally contain genes which have been manipulated to enable the plants to express proteins either identical to or substantially identical to naturally occurring proteins isolated from *Bacillus thringiensis* species of bacteria. Such proteins, designated through nomenclature as insecticidal crystal proteins or ICP's or *BT*'s, have been very effective in most plants which have been genetically altered to express them. However, these proteins are also susceptible to the development of resistance in various target insects. For example, the Cry3 class of proteins are *BT* ICP's which are particularly effective in controlling, inhibiting, or killing various Coleopteran species of insect larvae. Some members of this particular class are now used preferentially to control corn rootworms. However, it is presumed that when expressed alone in plants without some additional coleopteran effective treatment, a coleopteran larvae feeding on such a plant would eventually develop some level of resistance to the *BT* ICP, diminishing the effectiveness of the recombinant trait in the crop, and rendering valueless the efforts in procuring such recombinant varieties. The application of an additional treatment in combination with the *BT* ICP that had a separate mode of action when compared to the *BT* ICP and which was equally effective in controlling coleopteran species would diminish to vanishingly small the likelihood that resistant races of the target coleopteran species would develop at all One report has suggested that the co-expression of two or more *BT* ICP's in a plant, wherein each *BT* ICP was toxic to the same insect species but wherein each *BT* ICP expressed did not bind competitively to insect brush border membrane vesicle receptors, would diminish the likelihood that insect resistance would develop to any of the *BT* ICP's present in that plant. (Van Mellaert et al. U.S. Pat. No. 5,866,784; Feb. 2, 1999). However, although there are a variety of classes of *BT* ICP proteins, with each class of protein being particularly effective in controlling a class of insect species, such as Cry1's effectiveness vs lepidopterans, Cry2's effectiveness in controlling some lepidopterans but many which also have effects on dipterans, and Cry3's effectiveness in controlling some Coleopteran's, there are only a limited number of Cry proteins which could be used in the manner described. This lack of numerosity and variety is particularly true for the Cry3 class of proteins, ie those which are preferentially effective in controlling various Coleopteran species. In addition, more sensitive methods for measuring binding of *BT* ICP's to insect brush border membrane vesicle receptors have been developed since the methods as taught in Van Mellaert et al. The more sensitive methods suggest that even for those pairs of *BT* ICP's which Van Mellaert et al. demonstrated non-competitive binding, there appears in fact to be some competitive binding taking place, making it more likely that when two or more *BT* ICP's are used in combination which do not completely exhibit non-competitive binding, resistance to both *BT* ICP's could develop more rapidly than previously believed. Therefore, there is a need to identify and/or develop additional insect inhibitory proteins which do not act in the same way, ie using the same mode of action, as *BT* ICP's.

A variety of plant, bacterial, and fungal derived proteins have been identified which display insect inhibitory activity. Some of these include plant lectins, and as described above, other insect inhibitory proteins derived from Xenorhabdus and/or Photorhabdus species of bacteria. It is not clear whether these proteins act in modes different from that of the *BT* ICP's. It is clear, however, that there is increasing disinterest by various groups in having plants which express foreign proteins, ie proteins that are not otherwise naturally occurring in plants. It may be more acceptable to such groups to engineer plants which express useful proteins which have been derived from heterologous plant sources, or more preferably from homologous plant sources. In particular, identification of plant proteins which have properties of insect inhibition or insect control when ingested by insect pests, and which function in a way which is different from the function of *BT* ICP's or other bacterial or heterologous proteins would be particularly useful.

Plant non-specific lipid acyl hydrolases have been identified from a variety of plant sources including potato tubers, flowers, and leaves, bean leaves and rice bran as well as many other plant sources. The activity of plant non-specific lipid acyl hydrolases is extremely high in many tissues, and although their action in causing rancidity in stored agricultural products and in damaged or infected tissues has been well documented, their in vivo physiological role is still uncertain.

Patatin is a major potato tuber protein that has been shown to have esterase, lipase, and insect inhibitory activities. This protein is also classified as a non-specific lipid acyl hydrolase. As used herein, plant non-specific lipid acyl hydrolase includes a protein or protein sequence having substantial homology to potato patatin based on alignment algorithms and which can be demonstrated to hydrolyze acyl groups from at least one of several classes of lipids, including glycolipids, phospholipids, sulfolipids, and mono- and di-acyl glycerols, but is inactive on triacylglycerols. The acyl hydrolase releases both fatty acids from diacyl glycerolipids, and in many cases, there is no preference for either the 1- or 2-position of the acyl ester linkage. Thus, the enzyme possesses a combined catalytic capacity of phospholipase A1, A2, and B, as well as glycolipase, sulfolipases and monoacylglycerol lipase. Similarities of the plant non-specific lipid acyl hydrolase enzymes from various tissues include the following: (1) they exert a similar pattern of substrate specificity as described above; (2) they may occur as isozymes in each tissue and they have fairly similar patterns of substrate specificity; (3) the activity ratio of the enzyme preparation on galactolipid and phospholipid remains fairly constant throughout an enzyme purification procedure; and (4) the enzyme carries out acyltransferase reactions with each of the substrates (Gailliard, in "The Biochemistry of Plants", P. K. Stumpf and E. E. Conn, eds., v4:85–116, Academic Press, New York, 1980).

The best characterized plant non-specific lipid acyl hydrolase is patatin, isolated from potato tubers. Patatin is a mixture of at least 6 to 10 closely related polypeptides, isoforms, or isozymes which differ in their primary amino acid sequence, patterns of glycosylation, and hydrolytic activities (Hofgren et al., Plant Sci. 66:221–230, 1990). These proteins are encoded by a family of about 15 genes per haploid genome, and genes encoding several patatin isoforms have been sequenced and published (Mignery et al., Nucl. Acids Res. 12:7987–8000, 1984). Sequences encoding additional patatin related proteins from potato and from corn are set forth herein.

Patatin is synthesized as an approximately 43,000 Dalton (43 kDa) preprotein with a short signal peptide for targeted secretion into the ER and subsequent passage through the Golgi apparatus. The signal peptide is cleaved upon insertion of the mature peptide into the lumen of the ER and the mature form of patatin is glycosylated in the Golgi to become a mature protein of about 40 kDa. One skilled in the art will recognize that variant patatins or patatin related sequences displaying non-specific lipid acyl hydrolase activity and insect inhibitory bioactivity can vary by as much as 10–15 percent in size from the major potato patatin sequence. In any event, the present invention specifically contemplates the use of any of the patatin isoforms. It has been identified as a part of the inventions described herein that variations may exist in the amino acid sequence of patatin and related proteins without any significant effect on its functional characteristics. However, any changes to active site amino acid sequence motifs as disclosed herein have substantial impact on the enzymatic and insect inhibitory bioactivity, and therefore should be avoided when construing patatin homologs for use as contemplated herein.

Biochemical assays which monitor the lipolytic or esterolytic activity of plant non-specific lipid acyl hydrolases are useful for ensuring that proteins isolated from plant tissues are in fact lipid acyl hydrolases. To ensure that the enzyme activity observed in such assays is due to protein activity, protease sensitivity can be measured. In addition, insect bioassays are useful as monitors for the insect inhibitory activity displayed by non-specific lipid acyl hydrolases. One skilled in the art would know how to backtranslate from an amino acid sequence to obtain a DNA sequence which could be synthesized as a redundant probe to identify one or more genomic or cDNA sequences encoding one or more plant non-specific lipid acyl hydrolases. In fact, using the active site amino acid sequence motifs disclosed herein, one skilled in the art could easily identify any plant non-specific lipid acyl hydrolase from any plant tissue, whether monocot or dicot species.

Based on the analysis of the amino acid sequence of patatin, it has been previously shown that a serine residue is required for lipid acyl hydrolase activity as well as for insect inhibitory bioactivity, and that the serine residue within the amino acid sequence motif Gly-Xxx$_1$-Ser-Xxx$_2$-Gly (SEQ ID NO:14) is the catalytic serine residue. This disclosure reports the isolation of a single potato patatin isozyme, designated Pat17, and reports the results of alanine scanning mutagenesis of the gene encoding the protein to identify the likely catalytic residues responsible for both the esterase and insect inhibitory bioactivity. In addition, the active site amino acid sequence motif containing a required serine residue was altered to assess its role in catalytic function. A set of 75 amino acid sequence variants were generated using site-directed mutagenesis, expressed in the yeast Pichia pastoris, and analyzed for esterase activity. The variants identified using alanine scanning mutagenesis and displaying low esterase activity were purified and assayed for insect inhibitory activity. The inventors have herein identified Ser77 and Asp215 residues in Pat17 to be critical for both esterase and insect inhibitory bioactivity. The substitution of Ser77 with cysteine, alanine, aspartate, threonine, or asparagine residues significantly reduced both the esterase and insect inhibitory activity, further supporting the role of Ser77 in maintaining the activity of the protein. The pH rate profile of the protein indicates that a single residue with a pKa of less than about 5 must be deprotonated for the protein to show activity, which supports the role of Asp215 as a catalytic residue. Surprisingly, substitution of three His residues with alanine in Pat17 did not produce an inactive enzyme. His variant H109A could not be expressed. An isosteric change at this position, H109N, maintained full esterase and bioactivity. Other amino acid variations at position 109 included cysteine, aspartate, and arginine. These variants were also unable to be expressed, suggesting that His109 does not play a direct role in catalysis but instead is implicated as important in the stability of the protein, as suggested by the X-ray crystal structure. The X-Ray crystal structure solution, reported herein, along with the alanine scanning mutagenesis and the amino acid sequence alignments with other sequences having substantial homology to potato patatin further supports the requirement for serine and aspartate in catalysis and insect inhibition and further provides a means for identifying any member of a family of conserved plant proteins displaying non-specific lipid acyl hydrolase activity and insect inhibitory bioactivity and which utilizing serine and aspartate in maintaining these functions (FIG. 9). In particular the alignments have allowed the identification of consensus sequences which, when coupled with X-Ray crystallographic data on at least one of the aligned protein sequences, allows the identification of the residues which fold into the active site of the enzyme and which are necessary for maintaining lipid acyl hydrolase activity and insect inhibitory bioactivity. These alignment consensus sequences are set forth in FIG. 9 as underlined sequences and in SEQ ID NO:14 (Gly-Xaa$_1$-Ser-Xaa$_2$-Gly) and SEQ ID NO:15 (Glu-Xaa$_1$-Xaa$_2$-Leu-Val-Asp-Gly). Xaa$_1$ and Xaa$_2$ as set forth in SEQ ID NO:14 can be either Ser or Thr. Xaa$_1$ as set forth in SEQ ID NO:15 can be any of the aromatic amino acids such as Tyr, Phe, Trp, and preferably are either Tyr or Phe. Xaa$_2$ as set forth in SEQ ID NO:15 can be generally be a basically charged amino acid such as His or Asn, with a preference for either being equally weighted.

Variants or analogues of patatin or patatin homologs are also specifically contemplated herein. Other than the contemplated amino acid sequence variants or variants of varying lengths relative to potato patatin, each having or retaining acyl hydrolase activity and insect inhibitory bioactivity, other contemplated variants include permuteins. Permuteins are generally proteins that comprise an amino acid sequence not found in nature, but which, upon three dimensional analysis or modeling appear to fold in three dimensional space into the configuration of the native protein and continue to display at least the same enzymatic and insect inhibitory bioactivity as the native protein. In addition, it is preferable that the DNA sequence encoding the permutein display at least the same level of expression in host cells as a codon optimized DNA sequence encoding the native protein sequence. Herein, once the crystal structure of a protein is solved, if the carboxy and amino termini of the protein are near enough to one another, ie within about 50 Å, then one or more breakpoints within the protein sequence structure can be selected so that the ends of the breakpoint(s) form the new amino and carboxy termini of the resultant protein, the permutein which is then joined into a single contiguous amino acid sequence by constructing a DNA sequence encoding the new, novel protein sequence such that the old carboxy terminus codon is adjacent to and upstream of the original native amino terminal amino acid codon.

The positions of the internal breakpoints described herein are found on the protein surface, and are distributed throughout the linear sequence without any obvious bias towards the ends or the middle. Breakpoints occurring below the protein surface may additionally be selected. The rearranged two subunits may be joined by a peptide linker. A preferred embodiment involves the linking of the N-terminal and C-terminal subunits by a three amino acid linker, although linkers of various sizes may be used. Additionally, the N-terminal and C-terminal subunits may be joined lacking a linker sequence. Furthermore, a portion of the C-terminal subunit may be deleted and the connection made from the truncated C-terminal subunit to the original N-terminal subunit and vice versa as previously described (Yang and Schachman, *Proc. Natl. Acad. Sci. U.S.A.*, 90: 11980–11984, 1993; Viguera, et al., *Mol. Biol.*, 247: 670–681, 1995; Protasova, et al., *Prot. Eng.*, 7: 1373–1377, 1994).

The novel insecticidal proteins of the present invention may be represented by the formula:

$$X^1-(L)_a-X^2$$

wherein;

a is 0 or 1, if a is 0, then the permutein does not contain a linker sequence;

$X^1$ is a polypeptide sequence corresponding to amino acids n+1 through J;

$X^2$ is a polypeptide corresponding to amino acids 1 through n;

n is an integer ranging from 1 to J−1;

J is an integer greater than n+1; and

L is a linker.

In the formula above, the constituent amino acid residues of the novel insect inhibitory protein are numbered sequentially 1 through J from the original amino terminus to the original carboxyl terminus. A pair of adjacent amino acids within this protein may be numbered n and n+1 respectively where n is an integer ranging from 1 to J−1. The residue n+1 becomes the new N-terminus of the novel insect inhibitory protein and the residue n becomes the new C-terminus of the novel insect inhibitory protein.

For example, a parent protein sequence consisting of 120 amino acids may be selected as a starting point for designing a permutein (J=120). If the breakpoint is selected as being between position 40 and position 41, then n=40. If a linker is selected to join the two subunits, the resulting permutein will have the formula: (amino acids 41–120)-L-(amino acids 1–40). If a linker was not used, the resulting permutein will have the formula: (amino acids 41–120)-(amino acids 1–40).

The length of the amino acid sequence of the linker may be selected empirically, by using structural information, or by using a combination of the two approaches. When no structural information is available, a small series of linkers may be made whose length can span a range of 0 to 50 Å and whose sequence is chosen in order to be substantially consistent with surface exposure (Hopp and Woods, *Mol. Immunol.*, 20: 483–489, 1983; Kyte and Doolittle, *J. Mol. Biol.*, 157: 105–132, 1982; Lee and Richards, *J. Mol. Biol.*, 55: 379–400, 1971) and the ability to adopt a conformation which does not significantly affect the overall configuration of the protein (Karplus and Schulz, *Naturwissenschaften*, 72: 212–213, 1985). Assuming an average length of 2.0 to 3.8 Å per residue, this would mean the length to test would be between about 0 to about 30 residues, with 0 to about 15 residues being the preferred range. Accordingly, there are many such sequences that vary in length or composition that can serve as linkers with the primary consideration being that they be neither excessively long nor excessively short (Sandhu, et al., *Critical Rev. Biotech.*, 12: 437–467, 1992). If the linker is too long, entropy effects may destabilize the three-dimensional fold and may affect protein folding. If the linker is too short, it may destabilize the molecule due to torsional or steric strain.

Use of the distance between the chain ends, defined as the distance between the C-alpha carbons, may be used to define the length of the sequence to be used, or at least to limit the number of possibilities that may be tested in an empirical selection of linkers. Using the calculated length as a guide, linkers with a range of number of residues (calculated using 2 to 3.8 Å per residue) may be selected. These linkers may be composed of the original sequence, shortened or lengthened as necessary, and when lengthened the additional residues may be chosen to be flexible and hydrophilic as described above; or optionally the original sequence may be substituted for using a series of linkers, one example being Gly-Pro-Gly (SEQ ID NO:16); or optionally a combination of the original sequence and new sequence having the appropriate total length may be used. An alternative short, flexible linker sequence is Gly-Gly-Gly-Ser-Gly-Gly-Gly (SEQ ID NO:17).

Sequences of novel patatin analogs capable of folding to biologically active molecules may be prepared by appropriate selection of the beginning (amino terminus) and ending (carboxyl terminus) positions from within the original polypeptide chain while optionally using a linker sequence as described above. Amino and carboxyl termini may be selected from within a common stretch of sequence, referred to as a breakpoint region, using the guidelines described below. A novel amino acid sequence is thus generated by selecting amino and carboxyl termini from within the same breakpoint region. In many cases, the selection of the new termini will be such that the original position of the carboxyl terminus immediately preceded that of the amino terminus. However, selections of termini anywhere within the region may result in a functional protein, and that these will effectively lead to either deletions or additions to the amino or carboxyl portions of the new sequence.

The primary amino acid sequence of a protein dictates folding to the three-dimensional structure beneficial for expression of its biological function. It is possible to obtain and interpret three-dimensional structural information using X-ray diffraction of single protein crystals or nuclear magnetic resonance spectroscopy of protein solutions. Examples of structural information that are relevant to the identification of breakpoint regions include the location and type of protein secondary structure (alpha and 3–10 helices, parallel and anti-parallel beta sheets, chain reversals and turns, and loops (Kabsch and Sander, *Biopolymers*, 22: 2577–2637, 1983), the degree of solvent exposure of amino acid residues, the extent and type of interactions of residues with one another (Chothia, C., *Ann. Rev. Biochem.*, 53: 537–572, 1984), and the static and dynamic distribution of conformations along the polypeptide chain (Alber and Mathews, *Methods Enzymol.*, 154: 511–533, 1987). In some cases additional information is known about solvent exposure of residues, one example is a site of post-translational attachment of carbohydrate which is necessarily on the surface of the protein. When experimental structural information is not available, or when it is not feasible to obtain the information, methods are available to analyze the primary amino acid sequence in order to make predictions of protein secondary and tertiary structure, solvent accessibility and the occurrence of turns and loops (Fasman, G., Ed. Plenum, N.Y., 1989; Robson, B. and Gamier, J. *Nature*, 361: 506, 1993).

Biochemical methods may be applicable for empirically determining surface exposure when direct structural methods are not feasible; for example, using the identification of sites of chain scission following limited proteolysis in order to infer surface exposure (Gentile, F. and Salvatore, G., *Eur. J. Biochem.*, 218: 603–621, 1993). Thus, using either the experimentally derived structural information or predictive methods (Srinivasan, R. and Rose, G. D. *Proteins*, 22: 81–99, 1995), the parental amino acid sequence may be analyzed to classify regions according to whether or not they are integral to the maintenance of secondary and tertiary structure. The sequences within regions that are known to be involved in periodic secondary structure (alpha and 3–10 helices, parallel and anti-parallel beta sheets) are regions that should be avoided. Similarly, regions of amino acid sequence that are observed or predicted to have a low degree of solvent exposure are more likely to be part of the so-called hydrophobic core of the protein and should also be avoided for selection of amino and carboxyl termini. Regions that are known or predicted to be in surface turns or loops, and especially those regions that are known not to be required for biological activity, may be preferred sites for new amino and carboxyl termini. Stretches of amino acid sequence that are preferred based on the above criteria may be selected as breakpoint regions.

An embodiment of the invention is directed towards patatin permutein proteins. The permutein proteins preferably maintain esterase activity and insect inhibitory properties. The permutein proteins preferably are less allergenic than the wild type patatin protein to individuals or animals allergic to potatoes. This may be assayed by the binding of antibodies to the wild type patatin and patatin permutein proteins.

The permutein proteins may optionally contain a linker sequence. The linker may generally be any amino acid sequence, preferably is Gly-Gly-Gly-Ser-Gly-Gly-Gly (SEQ ID NO:17) or Gly-Pro-Gly (SEQ ID NO:16), and more preferably is Gly-Pro-Gly.

Embodiments of the invention also include isolated nucleic acid molecule segments comprising a structural nucleic acid sequence encoding a patatin permutein protein. The linker may generally be any amino acid sequence, preferably is Gly-Gly-Gly-Ser-Gly-Gly-Gly (SEQ ID NO:17) or Gly-Pro-Gly, (SEQ ID NO:16) and more preferably is Gly-Pro-Gly. Alternatively, the encoded patatin permutein protein may lack a linker sequence. An embodiment of the invention is directed towards recombinant vectors which encode a patatin permutein protein. Alternatively, the encoded patatin permutein protein may lack a linker sequence.

Another preferred embodiment of the present invention encompasses cells transformed with the DNA constructs disclosed herein, and by use of the transformation vectors well known in the art. Transformed cells contemplated in the present invention include both prokaryotic and eukaryotic cells which express the proteins encoded-for by the novel DNA constructs of the present invention. The process of producing transgenic cells is well-known in the art. In general, the method comprises transforming a suitable host cell with a DNA sequence which contains a promoter operatively linked to a coding region that encodes a non-specific lipid acyl hydrolase. Such a coding region is generally operatively linked to a transcription-terminating region, whereby the promoter is capable of driving the transcription of the coding region in the cell, and hence providing the cell the ability to produce the enzyme in vivo. Alternatively, in instances where it is desirable to control, regulate, or decrease the amount of a particular hydrolase or hydrolases expressed in a particular transgenic cell, the invention also provides for the expression of hydrolase antisense mRNA; intron antisense mRNA; chloroplast targeting antisense mRNA; or five prime untranslated region (UTR) antisense mRNA. The use of antisense mRNA as a means of controlling or decreasing the amount of a given protein of interest in a cell is well-known in the art.

In a preferred embodiment, the invention encompasses a plant cell which has been transformed with a nucleic acid sequence or DNA construct of the invention, and which expresses a gene or gene segment encoding one or more of the coleopteran-active non-specific lipid acyl hydrolases as disclosed herein. As used herein, the term "transgenic plant cell" is intended to refer to a plant cell that has incorporated DNA sequences, including but not limited to genes which are perhaps not normally present, DNA sequences not normally transcribed into RNA or translated into a protein ("expressed"), or any other genes or DNA sequences which one desires to introduce into the non-transformed plant, such as genes which may normally be present in the non-transformed plant but which one desires to either genetically engineer or to have altered expression.

It is contemplated that in some instances the genome of a transgenic plant of the present invention will have been augmented through the stable introduction of a coleopteran active non-specific lipid acyl hydrolase-encoding DNA constructs as disclosed herein. In some instances, more than one transgene will be incorporated into the nuclear genome, or into the chloroplast or plastid genome of the transformed host plant cell. Such is the case when more than one hydrolase protein-encoding DNA sequence is incorporated into the genome of such a plant. In certain situations, it may be desirable to have one, two, three, four, or even more non-specific lipid acyl hydrolase protein-encoding polynucleotides (either native or recombinantly-engineered) incorporated and stably expressed in the transformed transgenic plant.

In preferred embodiments, the introduction of the transgene into the genome of the plant cell results in a stable integration wherein the offspring of such plants also contain a copy of the transgene in their genome. The heritability of this genetic element by the progeny of the plant into which the gene was originally introduced is a preferred aspect of this invention. A preferred gene which may be introduced includes, for example a plant non-specific lipid acyl hydrolase enzyme, and particularly one or more of those described herein.

Means for transforming a plant cell and the preparation of a transgenic cell line are well-known in the art (as exemplified in U.S. Pat. Nos. 5,550,318; 5,508,468; 5,482,852; 5,384,253; 5,276,269; and 5,225,341, all specifically incorporated herein by reference in their entirety), and are briefly discussed herein. Vectors, plasmids, cosmids, YACs (yeast artificial chromosomes) and DNA segments for use in transforming such cells will, of course, generally comprise either the operons, genes, or gene-derived sequences of the present invention, either native, or synthetically-derived, and particularly those encoding the disclosed crystal proteins. These DNA constructs can further include structures such as promoters, enhancers, polylinkers, or even gene sequences which have positively- or negatively-regulating activity upon the particular genes of interest as desired. The DNA segment or gene may encode either a native or modified hydrolase protein, which will be expressed in the resultant recombinant cells, and/or which will impart an improved phenotype to the regenerated plant.

Transgenic cells specifically contemplated in the present invention include transgenic plant cells. Particularly preferred plant cells include those cells obtained from corn, wheat, soybean, turf grasses, ornamental plant, fruit tree, shrubs, vegetables, grains, legumes, and the like, or any plant into which introduction of a coleopteran active non-specific lipid acyl hydrolase transgene is desired.

In another aspect, plants transformed with any DNA construct of the present invention that express the proteins for which the construct encodes, are contemplated as being a part of this invention. Accordingly, the invention further provides transgenic plants which have been transformed with a DNA construct, as disclosed herein, and transformed by use of transformation vectors as disclosed herein. Agronomic, horticultural, ornamental, and other economically or commercially useful plants can be made in accordance with the methods described herein, to express plant non-specific lipid acyl hydrolases at levels high enough to confer resistance to insect pathogens while remaining morphologically normal.

Such plants may co-express the plant non-specific lipid acyl hydrolase polypeptide along with other antifungal, antibacterial, or antiviral pathogenesis-related peptides, polypeptides, or proteins; insect inhibitory proteins; proteins conferring herbicide resistance; and proteins involved in improving the quality or quantity of plant products or agronomic performance of plants. Simultaneous co-expression of multiple proteins in plants is advantageous in that it exploits more than one mode of action to control plant pathogenic damage. This can minimize the possibility of developing resistant pathogen strains, broaden the scope of resistance, and potentially result in a synergistic insect inhibitory effect, thereby enhancing a plant's ability to resist insect infestation (Intl. Patent Appl. Publ. No. WO 92/17591, Oct. 15, 1992, specifically incorporated herein by reference in its entirety).

The transformed plant of the current invention may be either a monocotyledonous plant or a dicotyledonous plant. Where the plant is a monocotyledonous plant, it may be any one of a variety of species. Preferred monocotyledonous species encompassed by the present invention may include maize, rice, wheat, barley, oats, rye, millet, sorghum, sugarcane, asparagus, turfgrass, or any of a number of other grains or cereal plants. In preferred embodiments, the monocot is a maize plant.

The present invention also contemplates a variety of dicotyledonous plants such as cotton, soybean, tomato, potato, citrus, tobacco, sugar beet, alfalfa, fava bean, pea, bean, apple, cherry, pear, strawberry, raspberry, or any other legume, tuber, or fruit plant. In preferred embodiments, the dicot is a soybean plant, a tobacco plant, or a cotton plant.

Many of the plants intended to be transformed according to the disclosed invention are commercial crop plants. The commercial form of these plants may be the original plants, or their offspring which have inherited desired transgenes. Accordingly, plants further contemplated within the ambit of the present invention include any offspring of plants transformed with any of the permutations of the DNA construct which are noted in this application. Specifically, the offspring may be defined as an $R_0$ transgenic plant. Other progeny of the transformed plant are also included within the scope of the present invention, including any progeny plant of any generation of the transformed plant, wherein the progeny plant has inherited the DNA construct from any $R_0$ plant.

Upon transformation with a specific DNA construct, the nucleic acid or polynucleotide segments of the construct may be incorporated in various portions into a chromosome of the transformant. Therefore, in another embodiment, the present invention encompasses any transgenic plant or plant cell prepared by the use of a DNA construct disclosed herein. Such a plant or cell encompassed by the present invention includes those prepared by a process which has the following steps: (1) obtaining a DNA construct including a coleopteran active plant non-specific lipid acyl hydrolase coding region positioned in frame and under the control of a promoter operable in the plant, and a signal peptide sequence coding region for ER targeting of the hydrolase positioned upstream of the plant non-specific lipid acyl hydrolase coding region and downstream of the promoter; and (2) transforming the plant with the obtained DNA construct, so that the plant expresses the plant non-specific lipid acyl hydrolase. The plant may also have been transformed so that it further incorporates into its genome and expresses other insect inhibitory proteins.

In a related aspect, the present invention also encompasses a seed produced by the transformed plant, a progeny from such seed, and a seed produced by the progeny of the original transgenic plant, produced in accordance with the above process. Such progeny and seeds will have a coleopteran active plant non-specific lipid acyl hydrolase transgene stably incorporated into its genome, and such progeny plants will inherit the traits afforded by the introduction of a stable transgene in Mendelian fashion. All such transgenic plants having incorporated into their genome transgenic DNA sequences encoding any DNA construct disclosed herein, particularly those disclosed in the examples and figures are aspects of this invention.

Recombinant plants, cells, seeds, and other tissues could also be produced in which only the mitochondrial or chloroplast DNA has been altered to incorporate the molecules envisioned in this application. Promoters which function in chloroplasts have been known in the art (Hanley-Bowden et al., Trends in Biochemical Sciences 12:67–70, 1987). Methods and compositions for obtaining cells containing chloroplasts into which heterologous DNA has been inserted has been described by Daniell et al., U.S. Pat. No. 5,693,507 (1997).

In another preferred embodiment, the present invention provides a method for expressing coleopteran active plant non-specific lipid acyl hydrolases at high levels in transgenic plants. The disclosed methods may exploit any of the DNA constructs disclosed herein, as well as any transformation vectors known in the art. The contemplated methods enable coleopteran active plant non-specific lipid acyl hydrolases for the control of several insect pests, to be expressed in plants without negatively affecting the recovery of agronomic qualities of transgenic plants. The invention described herein also enables expression of coleopteran active plant non-specific lipid acyl hydrolases at levels up to 10 times higher than that achieved by current methods.

The method described here thus enables plants expressing non-specific lipid acyl hydrolase to be used as either an alternative or supplement to plants expressing Cry 1, Cry2, and Cry3-type *B. thuringiensis* δ-endotoxins for both control and resistance management of key insect pests, including Ostrina sp, Diatraea sp, Helicoverpa sp, Spodoptera sp in *Zea mays;* Heliothis virescens, Helicoverpa sp, Pectinophora sp. in *Gossypium hirsutum;* and Anticarsia sp, Pseudoplusia sp, Epinotia sp in *Glycine max*. It is also contemplated that the methods described may be used to dramatically increase expression of plant nonspecific lipid acyl hydrolases including and related to potato patatin or homologues thereof, or permuteins thereof, thus increasing its effectiveness against target pests and decreasing the likelihood of evolved resistance to these proteins. In one embodiment of the present invention, the coleopteran active plant non-specific lipid acyl hydrolase is expressed.

The method of expressing a coleopteran active plant non-specific lipid acyl hydrolase in a plant disclosed herein includes the steps of: (1) obtaining nucleic acid sequence comprising a promoter operably linked to a first polynucleotide sequence encoding a signal peptide for targeting a protein to a type II secretory apparatus, and a second polynucleotide sequence, encoding a coleopteran active plant non-specific lipid acyl hydrolase, to yield a fusion protein comprised of an amino-terminal type II signal peptide and a coleopteran active plant non-specific lipid acyl hydrolase; and (2) transforming the plant with the DNA construct of step 1 so that the plant expresses the protein fusion. In a preferred embodiment, the nucleic acid segment employed in step (1) of this method is structured so that the 5' end of the second polynucleotide sequence is operably linked in the same translational reading frame to the 3' end of the first polynucleotide sequence.

The plant or plant cell transformed by the method disclosed herein may be either a monocotyledonous plant or a dicotyledonous plant. Where the plant is a monocotyledonous plant, it may be any one of a variety of species. Preferred monocotyledonous species encompassed by the present invention may include maize, rice, wheat, barley, oats, rye, millet, sorghum, sugarcane, asparagus, turfgrass, or any of a number of other grains or cereal plants. In preferred embodiments, the monocot is a maize plant.

The present invention also contemplates a process by which a variety of dicotyledonous plants or plant cells are transformed. Such dicotyledonous plants may include plants such as cotton, soybean, tomato, potato, citrus, tobacco, sugar beet, alfalfa, fava bean, pea, bean, apple, cherry, pear, strawberry, raspberry, or any other legume, tuber, or fruit plant. In preferred embodiments, the dicot is a soybean plant, a tobacco plant or cell, or a cotton plant or cell.

As noted with regard to other embodiments disclosed in the present invention, many of the plants intended to be transformed according to the disclosed invention are commercial crop plants. The commercial form of these plants may be the original plants, or their offspring which have inherited desired transgenes. Accordingly, the inventors further contemplate that the method disclosed herein includes a method of producing a transgenic progeny plant or progeny plant cell. The method of producing such progeny includes: The method of expressing a coleopteran active plant non-specific lipid acyl hydrolase in a plant disclosed herein includes the steps of: (1) obtaining nucleic acid sequence comprising a promoter operably linked to a first polynucleotide sequence encoding a signal peptide for targeting a protein to a type II secretory apparatus, and a second polynucleotide sequence, encoding a coleopteran active plant non-specific lipid acyl hydrolase, to yield a fusion protein comprised of an amino-terminal plastid transit peptide and a coleopteran active plant non-specific lipid acyl hydrolase; (2) obtaining a second plant; and (3) crossing the first and second plants to obtain a crossed transgenic progeny plant or plant cell which has inherited the nucleic acid segments from the first plant. The present invention specifically encompasses the progeny, progeny plant or seed from any of the monocotyledonous or dicotyledonous plants.

In another preferred embodiment, the method of expressing the coleopteran active plant non-specific lipid acyl hydrolases disclosed herein includes co-expression of the disclosed DNA construct in any of its various embodiments, along with a *B. thuringiensis* δ-endotoxin or a Xenorhabdus sp. or Photorhabdus sp. insect inhibitory protein. The method of expressing these bacterial insect inhibitory proteins and hydrolases together is expected to achieve increased insect inhibitory properties in the transformed plant through increased expression and decreased development of insect resistance—all of which are desired results not present in existing technologies. This co-expression may be in the original transformant, or in any number of generations of progeny of the original transformant which have inherited the genes to co-express the proteins encoded for by any of the DNA constructs disclosed herein.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

This example illustrates the preferred materials and methods used in this disclosure and should not be understood to be limiting. The example also illustrates the DNA and amino acid sequence of Pat17 and the variant peptides which were produced using alanine scanning mutagenesis.

Patatin is a member of a family of proteins found in potato and other solanaceous plants (Ganal, M., et al., *Genetic and physical mapping of the patatin genes in potato and tomato*. Mol Gen Genetics, 1991. 225: 501–509; Vancanneyt, G., et al., *Expression of a patatin-like protein in the anthers of potato and sweet pepper flowers*. Plant Cell, 1989. 1: 533–540). In potatoes, patatin is predominantly found in tubers, and at much lower levels in other plant organs (Hofgen, R. and L. Willmitzer, *Biochemical and genetic analysis of different patatin isoforms expressed in various organs of potato* (*Solanum tuberosum*). Plant Sci., 1990. 66:221–230). Genes that encode patatins have been previously isolated and characterized (Mignery, G. A., et al., *Isolation and sequence analysis of cDNAs for the major potato tuber protein, patatin*. Nucleic Acids Research, 1984. 12:7987–8000; Mignery, G. A., C. S. Pikaard, and W. D. Park, *Molecular characterization of the patatin multigene family of potato*. Gene, 1988. 62:27–44; Stiekema, W. J., et al., *Molecular cloning and analysis of four potato tuber mRNAs*. Plant Mol Biol, 1988. 11:255–269). These proteins have been shown to have acyl-hydrolase activity that catalyzes the non-specific hydrolysis of phospholipids, glycolipids, sulfolipids, and mono- and diacylglycerols (Hirayama, O., et al., *Purification and properties of a lipid cyl-hydrolase from potato tubers*. Biochim Biophys Acta, 1975. 384:127–137; Wardale, D. A., *Lipid-degrading enzymes from potato tubers*. Phytochemistry, 1980. 19:173–177). In addition, patatin has been shown to have insect inhibitory activity against corn rootworm, an economically important insect pest in corn (Strickland, J. A., G.

L. Orr, and T. A. Walsh, *Inhibition of Diabrotica larval growth by patatin, the lipid acyl hydrolase from potato tubers*. Plant Physiol, 1995. 109:667–674). The current treatment used to control insect pests, including lepidopteran and coleopteran species, is δ-endotoxins of *Bacillus thuringiensis* (*Bt*) (English, L., et al., *Modulation of delta-endotoxin ion channels. Molecular action of insecticides on ion channels*, ed. J. M. Clark. Vol. 591. 1995: Amer. Chem. Soc. Symposium. 302–307; Schnepf, E., et al., *Bacillus thuringiensis and its pesticidal crystal proteins*. Microbiology and molecular biology reviews, 1998. 62:775–806; Crickmore, N., et al., *Revision of the nomeclature for the Bacillus thuringiensis pesticidal crystal proteins*. Microbiology and Molecular Biology Reviews, 1998. 62:807–813). The mechanism of action of *Bt* proteins involves insertion of the toxin into the membrane of the insect midgut to create ion channels or pores (English et al., ibid; Schnepf et al., ibid). Because of the widespread use of *Bt* toxins, there is concern that development of resistance can shorten their useful product life. Laboratory selection has produced many resistant insects to *Bt* protein, but to date there is only one insect, diamondback moth (*Plutella xylostella*), that has evolved substantial resistance in the field (Tabashnik, B. E., et al., *Cross-resistance of the diamondback moth indicates altered interactions with domain II of Bacillus thuringiensis toxins*. Applied and Environmental Microbiology, 1996. 62:2839–2844). Patatins afford a different gene product for control of insect pests with a different mode of action which can be combined with *Bt* δ-endotoxins for resistance management.

A potato cDNA gene encoding an isozyme of patatin, designated herein as Pat17, was isolated from total DNA of *Solanum cardiophyllum* tubers as described herein and sequenced. The nucleotide (SEQ ID NO:37) and amino acid (SEQ ID NO:1) sequence of Pat17 is shown in FIG. 1. Comparison of this sequence with other lipases indicated that Pat17 had the conserved amino acid motif (Gly-Xxx-Ser-Xxx-Gly) describing esterases (Mignery et al (1), ibid; Mignery et al (2), ibid; Steikma et al, ibid; Rosahl, S., et al., *Isolation and characterization of a gene from Solanum tuberosum encoding patatin, the major storage protein of potato tubers*. Mol Gen Genet, 1986. 203:214–220). Chemical modification studies of patatin using diisopropyl fluorophosphate (DFP) eliminates both the enzymatic and insect inhibitory activities (Strickland et al., ibid). Based on chemical modification experiments and the prior disclosure of Walsh et al., (U.S. Pat. No. 5,743,477), Ser77 as implicated as being within the hydrolase motif and was solely responsible for the hydrolase activity and insect inhibitory bioactivity. However, other acyl hydrolase proteins had been observed to have a catalytic triad composed of Ser, Asp/Glu and His as a part of their active sites and so it was postulated that patatin may also contain other residues responsible for activity (Strickland et al., ibid; Senda, K., et al., *A cytosolic phospholipase A2 from potato tissues appears to be patatin*. Plant Cell Physiol, 1996. 37:347–353; Schrag, J. D., et al., *Ser-His-Glu triad forms the catalytic site of the lipase from Geotrichum candidum*. Nature, 1991. 351:761–764).

Therefore, alanine-scanning mutagenesis was used to identify any likely catalytic residues (Cunningham, B. and J. Wells, *High-Resolution Epitope Mapping of hGH-Receptor Interactions by Alanine-Scanning Mutagenesis*. Science, 1989. 244:1081–1085; Bennett, W. F., et al., *High resolution analysis of functional determinants on human tissue-type plasminogen activator*. J Biol Chem, 1991. 266:5191–5201). All codons in the Pat17 coding sequence encoding charged residues were altered to encode alanine in groups of 1–3 residues (Table 1). The "charged to alanine" scan variants would also help to identify residues, in addition to potential catalytic residues, which are important for activity and/or stability. A set of 75 variants were constructed using site-directed mutagenesis as shown in Table 1. All the variants were expressed in *Pichia pastoris* and assayed for enzyme activity. The variants with very low enzyme activity were subsequently purified and assayed for bioactivity. Based on the consensus esterase motif, Gly-$Xxx_1$-Ser-$Xxx_2$-Gly, we also changed the codon for Ser77 to Ala77 to verify that this residue is indeed responsible for catalytic and bioactivity. The inventors herein show that Pat17 contains serine and aspartate residues that are critical for both enzymatic and insect inhibitory activities. In addition, the inventors herein have identified a histidine residue at position 109 as important in maintaining enzyme stability. The results herein suggest that Pat17 is similar to a recently identified phospholipase $A_2$ also employing a serine/aspartate dyad in catalysis (Dessen, A., et al., *Crystal structure of human cytosolic phospholipase $A_2$ reveals a novel topology and catalytic mechanism*. Cell, 1999. 97:349–360). Surprisingly, however, the Dessen et al. amino acid sequence fails to align at all with any of the plant derived sequences disclosed herein, indicating only that the two proteins contain active sites based on a similar biocatalytic theme but which exhibit substantially unrelated sequences and activities otherwise.

TABLE 1

Charged to Alanine Scan Variants

| Column 1 | Column 2 |
| --- | --- |
| Wild type | D223A |
| E27A | R234A |
| D35A | K238A |
| R40A | D239A |
| E49A | R246A |
| E52A | K251A/K252A |
| E57A/D59A | E265A/D267A |
| D63A | K268A |
| R65A | K273A |
| D68A | E274A |
| D71A | H282A |
| S77A | K289A |
| E91A | D292A |
| R94A | D300A |
| K100A | D311A |
| E101A | K313A |
| E108A | R318A |
| H109A | E321A |
| K124A | E330A |
| D126A | D332A |
| K128A | D333A |
| E136A | E336A |
| K137A | E340A |
| E140A | E347A |
| R142A | K351A/K352A |
| H144A | E356A/D357A |
| E149A | E360A |
| D156A | E363A |
| K158A | E364A |
| K161A | K367A |
| K167A | R368A |
| E175A | K371A |
| D177A | D375A |
| K179A | R376A |
| D182A | K377A |
| H197A | K378A |

TABLE 1-continued

Charged to Alanine Scan Variants

| Column 1 | Column 2 |
|---|---|
| D207A/E208A/E210A | R380A |
| D215A | K383A |

Each native residue indicated by the first letter at each position in each column was altered by site directed mutagenesis or by thermal amplification to an alanine residue. Subsequent sequences were confirmed by DNA sequence analysis, and variant proteins were subsequently produced in *P. Pastoris* expression system to confirm presence of protein, and to test protein produced for insect inhibitory bioactivity and for lipid acyl hydrolase activity.

Genes for patatin have been cloned by several investigators, as indicated above. The sequence disclosed was used to design primers to clone the Pat17 gene from *S. cardiophyllum*. Total RNA was prepared from *Solanum cardiophyllum* tubers using TRI REAGENT according to the manufacturers protocol (Molecular Research Center, Inc.). The RNA was used to generate cDNA using reverse transcription. A full-length cDNA of Pat17 was amplified using thermal ampification methods and the amplification primers SEQ ID NO:18 5'-GTTAGATCTCA CCATGGCAACTACTAAATCTTT-3' (NcoI site indicated by underlined bases) and SEQ ID NO:19 5'-CCAGAATTCT CATTAATAAGAAGCTTTGTTTGC-3' (EcoRI site indicated by underlined bases).

Standard thermal amplification reaction conditions as described in the GENE AMP kit (Perkin-Elmer Cetus) were used, however an annealing temperature of 40° C. was used in the alternative. Resulting DNA was cloned into pBluescript plasmid (Stratagene, Calif.) and the insert was confirmed by DNA sequence analysis.

Pat17 variants were generated using an oligonucleotide-directed mutagenesis protocol from Bio-Rad Laboratories (Richmond, Calif.) which is based on the method of Kunkel (Kunkel, D. A., *Rapid and efficient site-specific mutagenesis without phenotypic selection.* Proc Natl Acad Sci USA, 1985. 82:477–92). The Pat17 gene was cloned into the plasmid pBluescript SK+ (Strategene, Calif.) under conditions which facilitated the generation of single-stranded DNA. The mutagenesis procedure was followed as outlined in the protocol. Mutagenic oligonucleotides were purchased from Midland Reagent Company (Midland, Tex.). Mutant clones were identified by sequencing the region covered by the mutagenic oligonucleotides.

The wild-type and Pat17 variants were digested with XhoI/EcoRI and ligated to the respective sites in the *P. pastoris* expression vector pPIC9 (Invitrogen, Calif.) used for extracellular expression. The transformation of the *P. pastoris* strain KM71 (Invitrogen, Calif.), screening for recombinants, and expression experiments were performed as outlined according to the manufacturer's instructions.

Culture supernatants of *P. pastoris* transformants producing recombinant protein were dialyzed against 25 mM Tris/HCl pH 7.5 (buffer A) and loaded onto Mono Q HR 10/10 anion-exchange column (Amersham Pharmacia, N.J.) equilibrated with buffer A. The protein was eluted with 25 mM Tris/HCl pH 7.5, 1 M KCl (buffer B) using a linear gradient of 0–100% buffer B run over 30 min at a flow rate of 4 mL/min using an HPLC system (Shimadzu). Fractions containing protein were assayed for esterase activity, dialyzed against 25 mM Tris/HCl pH 7.5, 1 M Ammonium sulfate, 1 mM β-mercaptoethanol (buffer C). The protein was purified to homogeneity by loading onto a phenyl-Sepharose 16/10 column (Amersham Pharmacia, N.J.) equilibrated with buffer C. The protein was eluted with buffer A using a linear gradient of 0–100% at a flow rate of 3 mL/min using an HPLC system (Shimadzu). Esterase active fractions were pooled and dialyzed against 25 mM Tris pH 7.5.

Enzyme activity was measured as described previously using p-nitrophenyl caprate (Sigma, Mo.) as a substrate (Hofgen et al., ibid). The substrate was initially dissolved in dimethylsulfoxide (5 mM stock solution) and diluted in 4% Triton X-100, 1% SDS to a final concentration of 1 mM. For the assay, 25 $\mu$L of the 1 mM substrate solution was added to 80 $\mu$L of 50 mM Tris pH 8.5 prior to the addition of 20 $\mu$L of protein solution. The enzyme activity was monitored at 405 nm in 6 sec interval for a period of 10 min. Esterase activity was expressed as $\Delta A$ $\min^{-1}$ $\mathrm{ug}^{-1}$ protein. Steady-state kinetic assays at different pH's were performed using Sodium acetate (pH 4–5.0), MES (pH 5–7.0), TRIZMA (pH 7–9.0), CHES (pH 9.5) with a 150 $\mu$L total volume. Assays were initiated with 10 $\mu$L of enzyme containing 0.1 mg/mL protein in 25 mM Tris pH 7.5. The reactions were quenched after 5 min with 850 $\mu$L of 200 mM Borate buffer (pH 9.8) and the absorbance was measured at 405 nm. The reaction rate was calculated using an extinction coefficient of 18.4 for p-nitrophenol. The $K_m$ values for the substrate was determined by varying the substrate concentration (5–10 time the $K_m$ value). The steady-state kinetic data were analyzed using KINETASYST (IntelliKinetics, New Jersey).

Insect bioassays for activity against larvae of *Diabrotica undecimpunctata howardi* (southern corn rootworm) were carried out by overlaying the test sample on an agar diet similar to that described previously (Marrone, P., et al., *Improvements in laboratory rearing of the southern corn rootworm, Diabrotica undecimpuncta howardi barber (coleoptera: chrysomelidae), on an artificial diet and corn.* J. Econ. Entom., 1985. 78:290–293). Proteins to be tested were diluted in 25 mM Tris/HCl pH 7.5 and overlayed on the diet surface. Neonate larvae were allowed to feed on the diet and mortality and growth stunting were evaluated after 6 days.

N-terminally-His-tagged Seleno-Methionine (Se-Met) Pat17 was expressed by metabolic labeling with Se-Met in a Se-Met-tolerant Met auxotroph of *E. coli* and was purified using Ni-chelate followed by anion exchange chromatography. Electrospray mass spectrometry revealed that the enzyme sample (41833 Da) contained Se-Met residues at all 13 methionine positions. The enzyme was crystallized using the technique of vapor diffusion by hanging drops. The protein sample was 10 mg/ml in 10 mM Tris-pH 7.4 and the precipitant solution was 16% PEG3350, 0.24 M ammonium acetate. A droplet comprised of 2 ml of protein solution and 2 ml of precipitant solution were placed on a siliconized coverslip and suspended over a grease-sealed well of a Linbro plate containing 500 ml of precipitant solution. Crystals appeared within five days. Preliminary in-house diffraction analyses on cryo-cooled crystals were conducted using an MSC R-AXIS IV imaging plate detector mounted on an MSC RU300H3R X-ray generator, operating at a power of 50 kV and 100 mA, with beam collimation provided by MSC/Yale mirrors, and cryo-cooling achieved using an MSC X-Stream unit operating at approximately −140 degrees C. Crystals taken from the drops were dipped in a cryo-solution which was 16.5% PEG3350, 0.23 M ammonium acetate, 25% ethylene glycol prior to flash-cooling in the cold stream of the R-AXIS IV unit. Diffraction studies revealed that the crystals were space group $C222_1$, with α=97.2 Å, b=171.4 Å, c=129.8 Å, and that they diffracted to better than 2.5 Å resolution. Protein/solvent content calculations based on the lattice and diffraction quality of the crystals suggested three Pat17 molecules in the asymmetric unit. The structure was solved using Se-Met Multi-wavelength Anomalous Dispersion (MAD) phasing methods. Four wavelengths of MAD data (11=0.9791 Å, 12=0.9792 Å, 13=1.019 Å, 14=0.942 Å) were collected at the IMCA beamline of the APS synchrotron. A Marresearch CCD detector was used to collect the diffraction data and the crystal was cryo-cooled using the aforementioned cryo-solution and an Oxford Cryo-stream unit operating at approximately −140 degrees C. 360 degrees of data at each wavelength were collected using 2.5 second exposures, an oscillation angle of 0.5 degrees, and a crystal-to-detector distance of 130 mm. The data were reduced using the HKL2000 package. The SOLVE program was employed to locate 33 of 39 Se sites in the asymmetric unit using 20–2.2 Å data. Phases from SOLVE were improved using the CCP4 package utility DM. A single Pat17 molecule was built into a 2.2 Å resolution experimental map using an SGI Octane workstation with stereo-graphics capability, the O program and the InsightII Biopolymer module. The Pat17 coordinates, 8–3.5 Å data, and the AMoRe molecular replacement package were used to locate all three molecules in the asymmetric unit (R−f=0.384).

Example 2

This example illustrates the lipid acyl hydrolase esterase activity of the charged to alanine scan variants described in Example 1.

Table 1 shows the list of charged to alanine scan variants. All the variants were expressed in *P. pastoris* and assayed for esterase activity as shown in FIG. 2. The level of protein expression was assayed using an ELISA and a monoclonal antibody specific for the Pat17 native amino acid sequence. Some of the variants could not be expressed including E52A, D68A, D71A and H109A, suggesting that these residues are critical for enzyme stability. Variants E91A, R94A and E136A showed good enzyme activity but could not be detected by the monoclonal antibody used in the ELISA suggesting that these are the potential recognition epitopes for the monoclonal antibody. All variants were assessed on Western blots probed with a polyclonal antibody to validate the ELISA expression values. The variant comprising D215A showed significant loss in esterase activity suggesting that this residue is critical for esterase activity (FIG. 2 and Table 2).

TABLE 2

Esterase Activity of Variants at Position 77, 109 and 215.

| Variants | Esterase Activity (ΔOD.min$^{-1}$. μg$^{-1}$) |
|---|---|
| Wild type | 116.0 |
| S77A | 0.02 |
| S77D | 0.01 |
| S77T | 0.1 |
| S77N | 0.01 |
| S77C | 0.1 |
| S77R[a] | N/A |
| H109A[a] | N/A |
| H109N | 234.5 |
| D215A | 0.02 |

[a]No protein expression was detected. The detection limit of the assay is 0.01.

As Ser77 lies in a hydrolase motif identified in U.S. Pat. No. 5,743,477, a S77A variant was constructed to elucidate its role in catalysis. As shown in FIG. 2, S77A was inactive towards the esterase substrate, suggesting that this residue is necessary for catalysis. Activity greater than that of the wild type Pat17 was observed for the variants at positions 65 and 352 (5-fold increase). Based on the X-ray crystal structure, the side chains of these basic residues (R65A, K351A/K352A) appear to lie on surface loops and to be facing in the same direction. Esterase activity of all the other variants varied from 0.5-fold to 4.2-fold respectively of the wild type protein. Several variants were also made at position 77 including S77A, S77D, S77T, S77N, S77C and S77R in order to elucidate the primary sequence requirements for enzymatic activity. The results of the esterase activity assay for the variants at position 77 are shown in Table 2. All the Ser77 variants were found to be inactive towards esterase substrates compared to the wild type enzyme suggesting that Ser77 is one of the catalytic residue involved in covalent catalysis. Histidine is usually a very conserved residue in the normal lipase catalytic triad, and thus we changed His109 to asparagine (an isosteric residue to His) and evaluated its esterase activity (shown in Table 2). It was surprising to note that H109N maintained full catalytic activity. Other changes at this position including H109C, H109D, H109R could not be expressed suggesting that the nitrogen atom in His109 is critical for maintaining the activity of the enzyme. This result rules out the possibility that His109 plays a direct role in catalysis. This data is further supported by the X-ray crystal structure which shows that His109 stabilizes the interaction between two helices and probably helps in maintaining the overall conformation of the protein.

Example 3

This example illustrates the pH rate profile of the native Pat17 enzyme.

Figure 3:
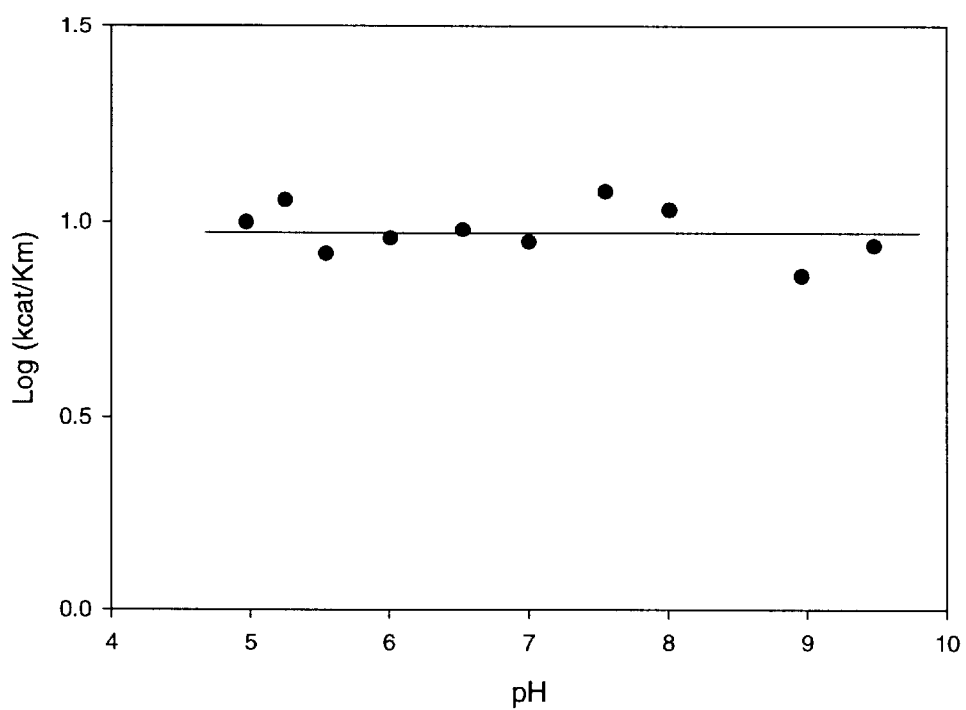

The plot of the data for $k_{cat}/K_m$ for p-nitrophenyl caprate substrate is shown in FIG. 3. The pH-independent value of the kinetic parameters are: $k_{cat}$=2.7 s$^{-1}$ and $k_{cat}/K_m$=9.3 mM$^{-1}$ s$^{-1}$. The $k_{cat}/K_m$ is essentially pH independent over the pH range of 5–9.5. This result suggests that a single residue with a pKa <5 must be deprotonated for enzyme activity, supporting the alanine scanning mutagenesis which identified Asp215 as at least one of the catalytic residues.

Example 4

This example illustrates the coordinated requirement for functional enzyme activity and insect inhibition for the native and variant forms of patatin.

Figure 4:
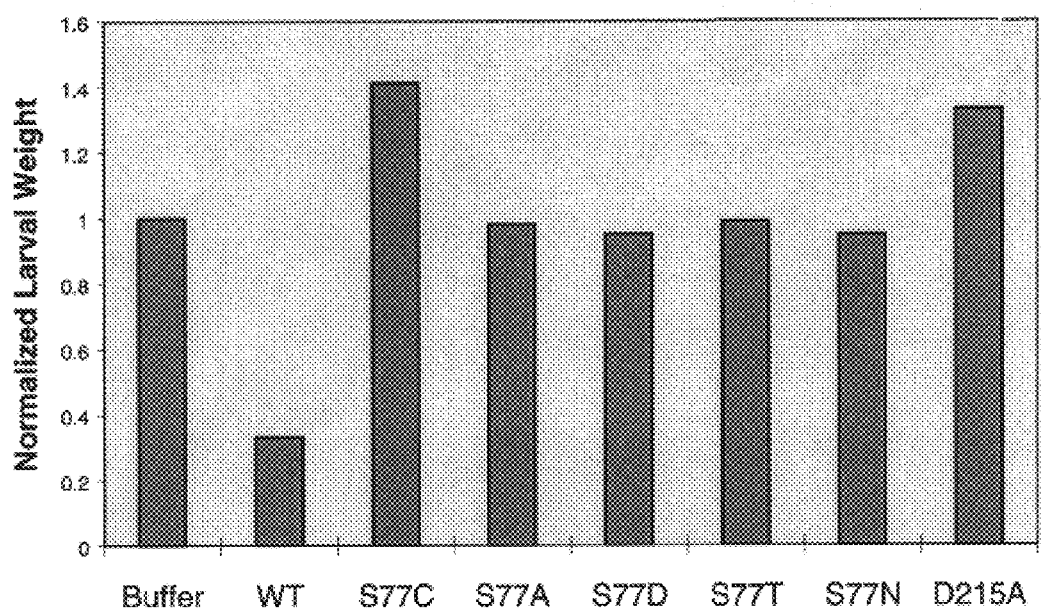

It has previously been shown that the enzymatic activity of patatin is required for it to also display effective insect inhibitory bioactivity. Therefore, the Ser77 variants described above (S77A, S77D, S77T, S77N, S77C) and the aspartate variant D215A were tested in an insect bioassay against southern corn rootworm (SCRW). The results are shown in FIG. 4. All of the assays were performed by overlaying protein (200 ppm final concentration) onto a corn rootworm artificial diet medium. All insects growth was stunted when native Pat17 was used, however no insect mortality was observed. All esterase inactive variants displayed no activity against SCRW suggesting that Ser77 and Asp215 are required for esterase activity and insect inhibitory bioactivity.

Figure 5:
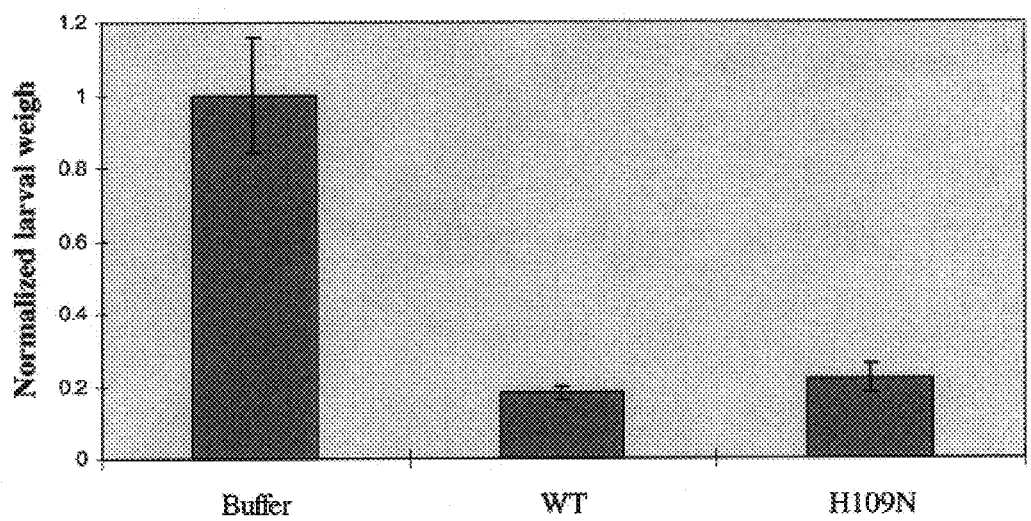

Assays were also conducted to evaluate the bioactivity of the H109N variant. As shown in FIG. 5, H109N had similar activity as the wild type enzyme in inhibiting the growth of SCRW larvae. The assay for H109N was performed in a similar manner as the other assays but the final concentration of overlayed protein was 100

Example 5

This example illustrates the model for the chemical mechanism of patatin non-specific lipid acyl hydrolase catalysis.

Figure 6A:
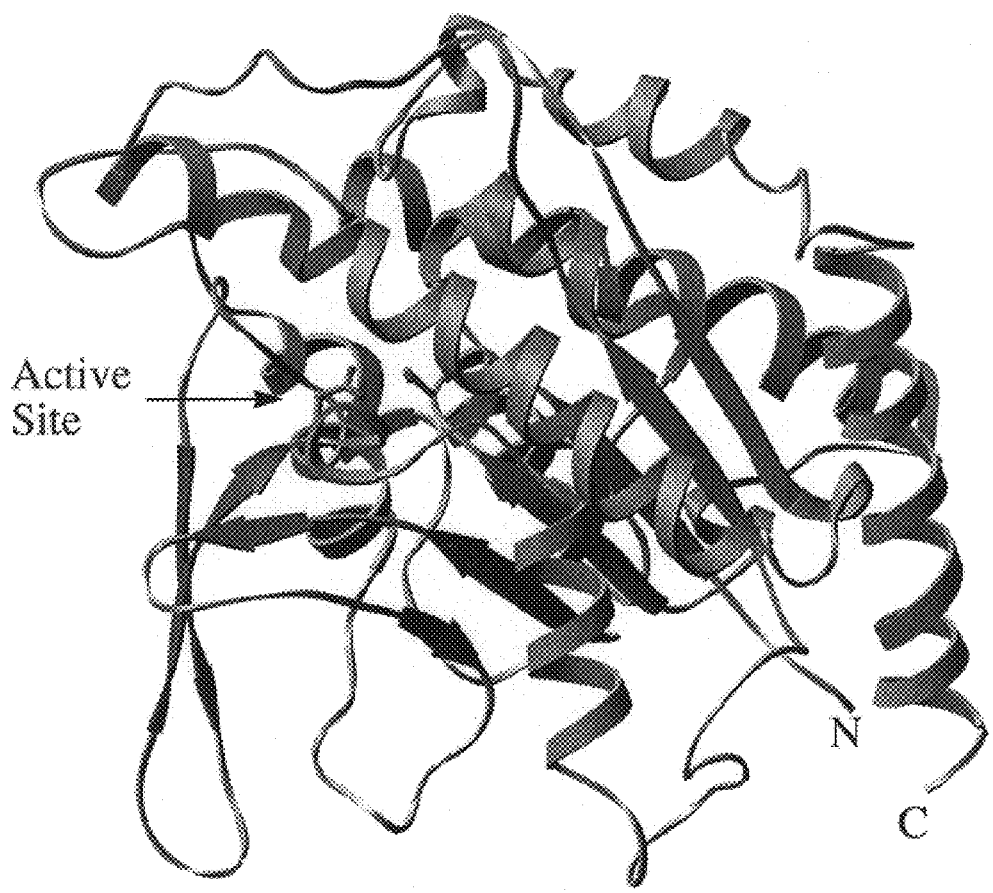
Figure 6B:
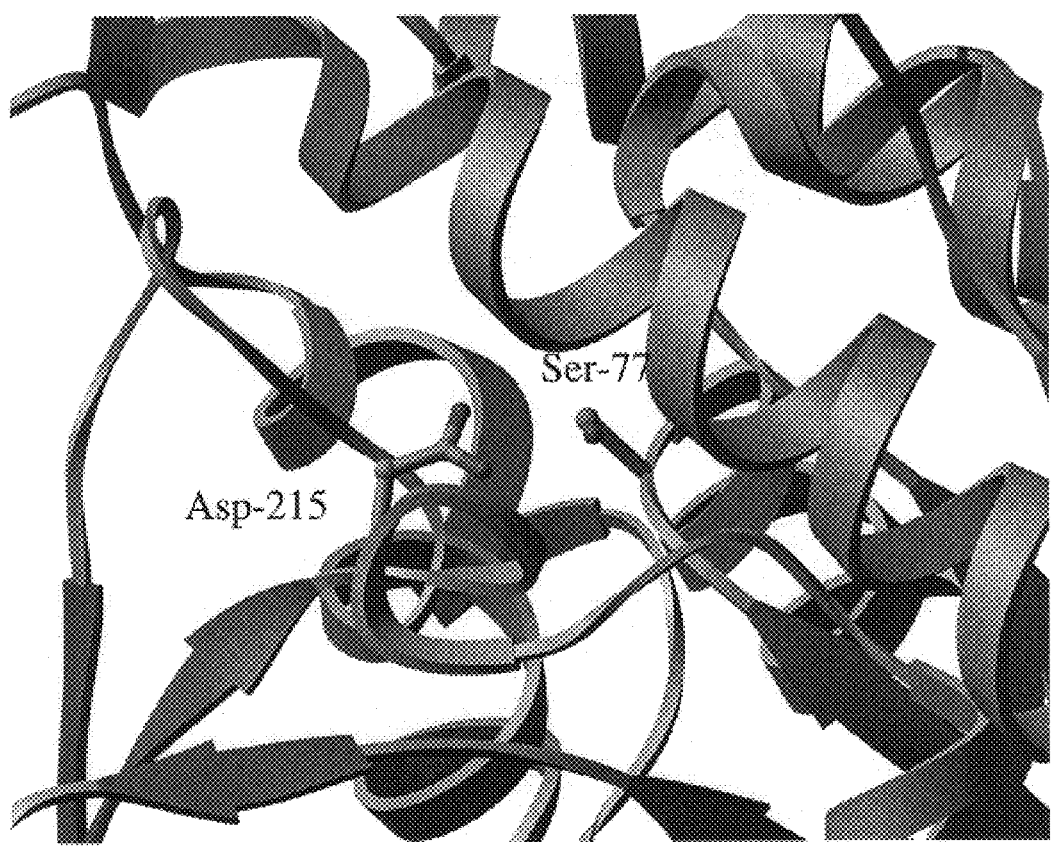

Patatin has been classified as a Ser hydrolase due to the presence of the general amino acid motif, Gly-Xxx$_1$-Ser-Xxx$_2$-Gly (SEQ ID NO:14) in the protein sequence. Previous chemical modification studies have shown that DFP-treated patatin had >20-fold reduction in esterase activity and no bioactivity. The instant disclosure describes the cloning of an isozyme of patatin designated herein as Pat17. On the basis of the Gly-Xxx$_1$-Ser-Xxx$_2$-Gly (SEQ ID NO:14) consensus sequence, Ser77 is predicted to be involved in catalysis in Pat17. As the structure of patatin was not known when this work was initiated, other catalytic residues in the α/β hydrolase fold family of enzymes were also implicated. As in the family of α/β hydrolases, the nucleophile can either be Ser, Cys or Asp. Therefore, the inventors herein altered the Ser77 to Ala, Cys, Asp, Thr, Asn, and Arg. All the variants were assayed for esterase and insect inhibitory activity and the results indicate that this residue is critical for both activities. Patatin has also been classified as a lipid acyl hydrolase because it exhibits phospholipase activity. The sequential order of active site residues in some lipases is Ser, Asp/Glu, His with the Ser being the only residue identifiable by sequence, gazing. Since there is no consensus motif to identify or predict the His and the carboxylate residues, the inventors herein utilized site-directed mutagenesis to construct a synoptic set of clustered point mutations in Pat17 by changing all the charged residues in the protein including Glu, Asp, His, Lys, and Arg to alanine in groups of 1–3 to identify the active site residues. This method, "clustered charged-to-alanine scan," has previously been used to identify critical residues in other proteins. The results described herein have identified Asp215 as the carboxylate residue critical for catalysis. The pH rate profile of Pat17 reveals that an acidic group with a pKa of <5 is important in catalysis suggesting that Asp215 within the Glu-Xaa$_1$-Xaa$_2$-Leu-Val-Asp-Gly (SEQ ID NO:15) consensus motif is the catalytic base (FIG. 3). The X-ray crystal structure indicates that Ser77 and Asp215 are within hydrogen bonding distance and thus support the notion that these residues are the catalytic residues (FIGS. 6a,b). The results herein also suggest that His109 is critical for maintaining the activity of the enzyme. The substitution of Ala, Cys, Asp, or Arg at position 109 is not permitted as no protein could be detected by ELISA and/or Western blot, suggesting that this position might be crucial for stability of the enzyme. An isosteric change at this position (H109N) generates a protein which maintains full esterase and insect inhibitory activity. An analysis of the patatin homolog alignment in FIG. 9 indicates that the Histidine or Asparagine at this position is also within a conserved sequence as set forth in SEQ ID NO:42 as Phe-Tyr-Xaa$_1$-Glu-His/Asn-Gly-Pro, wherein the Xaa$_1$ can be either Phe, Ile, or Leu.

Figure 7:
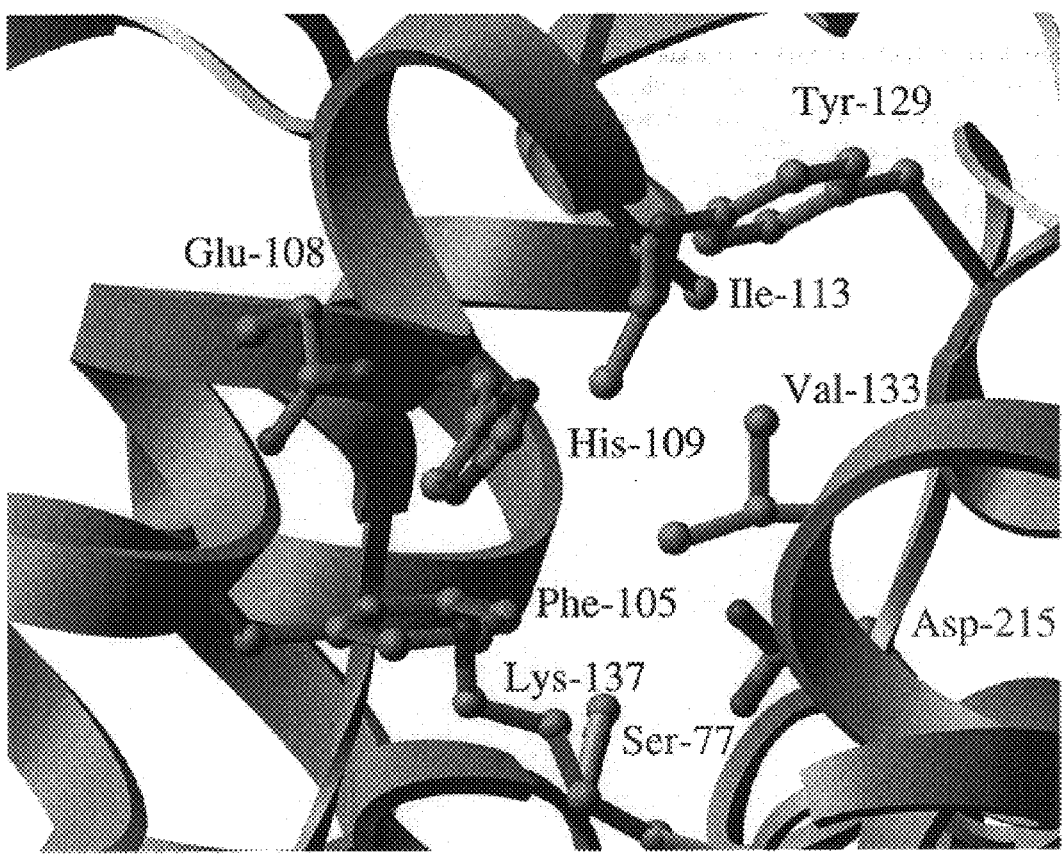

Analysis of the X-ray crystal structure indicates that His109 stabilizes the interaction between two helices by acting as a nucleus of a hydrophobic/polar cavity bounded by Phe105, Glu108, Ile113, Tyr129, Val133 and Lys137 (FIG. 7). This residue probably helps stabilize the structure by keeping the helices in close proximity and thus helps to maintain the overall fold of the enzyme. An asparagine at position 109 (H109N variant), maintains full esterase and bioactivity. All of the data discussed supports the roles of Ser77 and Asp215 as critical residues in catalysis which is also supported by the pH profile and the X-ray crystal structure. In addition, two variants at positions 65 and 252 (R65A, K251A/K252A) have also been identified which exhibited a 5.0-fold increase in esterase activity compared to the wild type enzyme. Examining the crystal structure reveals that these residues are predicted to be located at the Pat17 molecular surface. Further analysis can be done to assess their role in insect inhibition. Charged to alanine substitutions has previously been used to generate variants with increased specificity for substrates.

Figure 8:
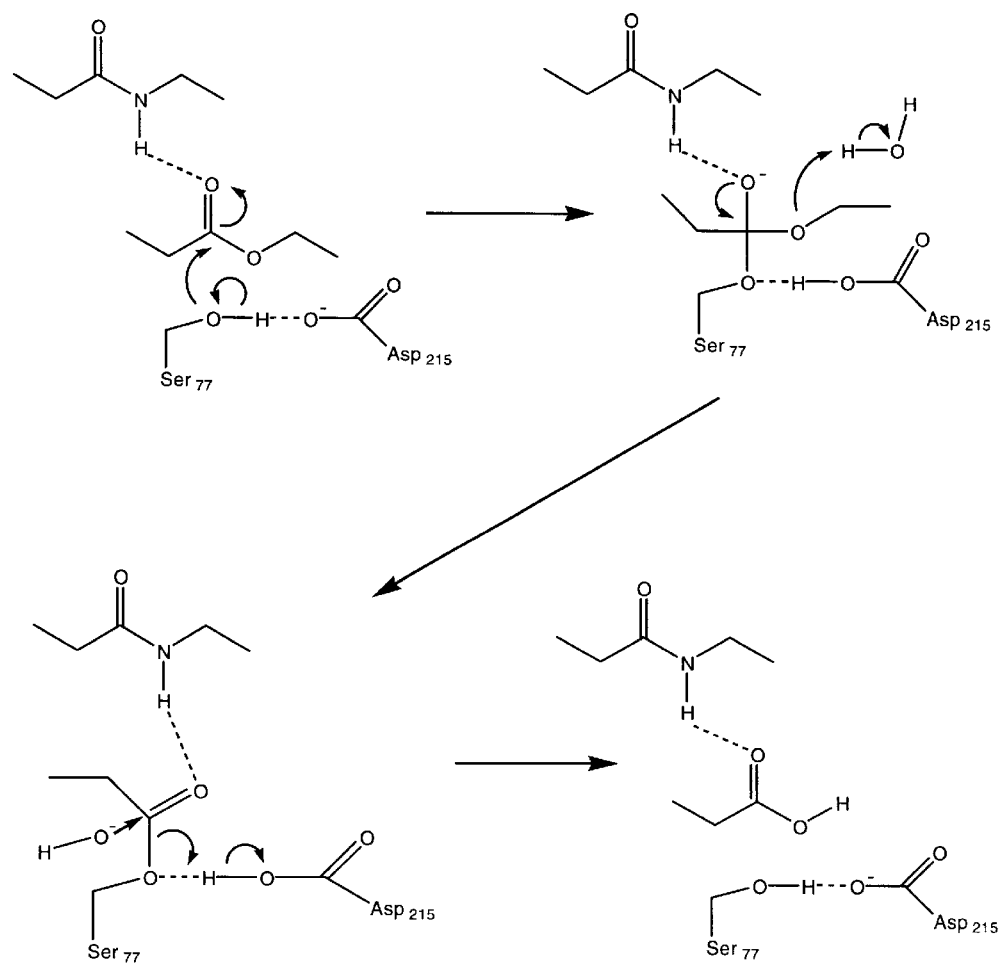

A model depicting the roles of Ser77 and Asp215 in catalysis is illustrated in FIG. 8. This model illustrates that Ser77 can serve as the nucleophile that attacks the carbonyl carbon of the scissile peptide bond with Asp215 serving as the base. This is supported by X-ray crystal studies which indicate that Ser77 and Asp215 lie within hydrogen bonding distance from each other and they make up the elements of the active site (FIGS. 6a,b).

The model depicted herein suggests that patatin uses a Ser-Asp dyad rather than the standard Ser-His-Asp triad found in proteases, lipases and esterases. Recently, a phospholipase A$_2$ has been identified that has a similar Ser-Asp dyad in the active site. The results herein suggest that patatin is a member of a new family of lipid acyl hydrolases that employ Ser-Asp dyad in catalysis. Recently, other novel serine proteases have been discovered that use hydroxyl/ε-amine or hydroxyl/α-amine catalytic dyads to perfom catalysis. The identification of a new class of lipid acyl hydrolases that utilize Ser-Asp catalytic dyads, depicted by patatin and phospholipase A$_2$, suggest that other variations in the classical catalytic triad theme in addition to the Ser/Lys catalytic dyads exist, and further structure/function studies of these enzymes would lead to a better understanding of these proteins.

Example 6

Figure 10:
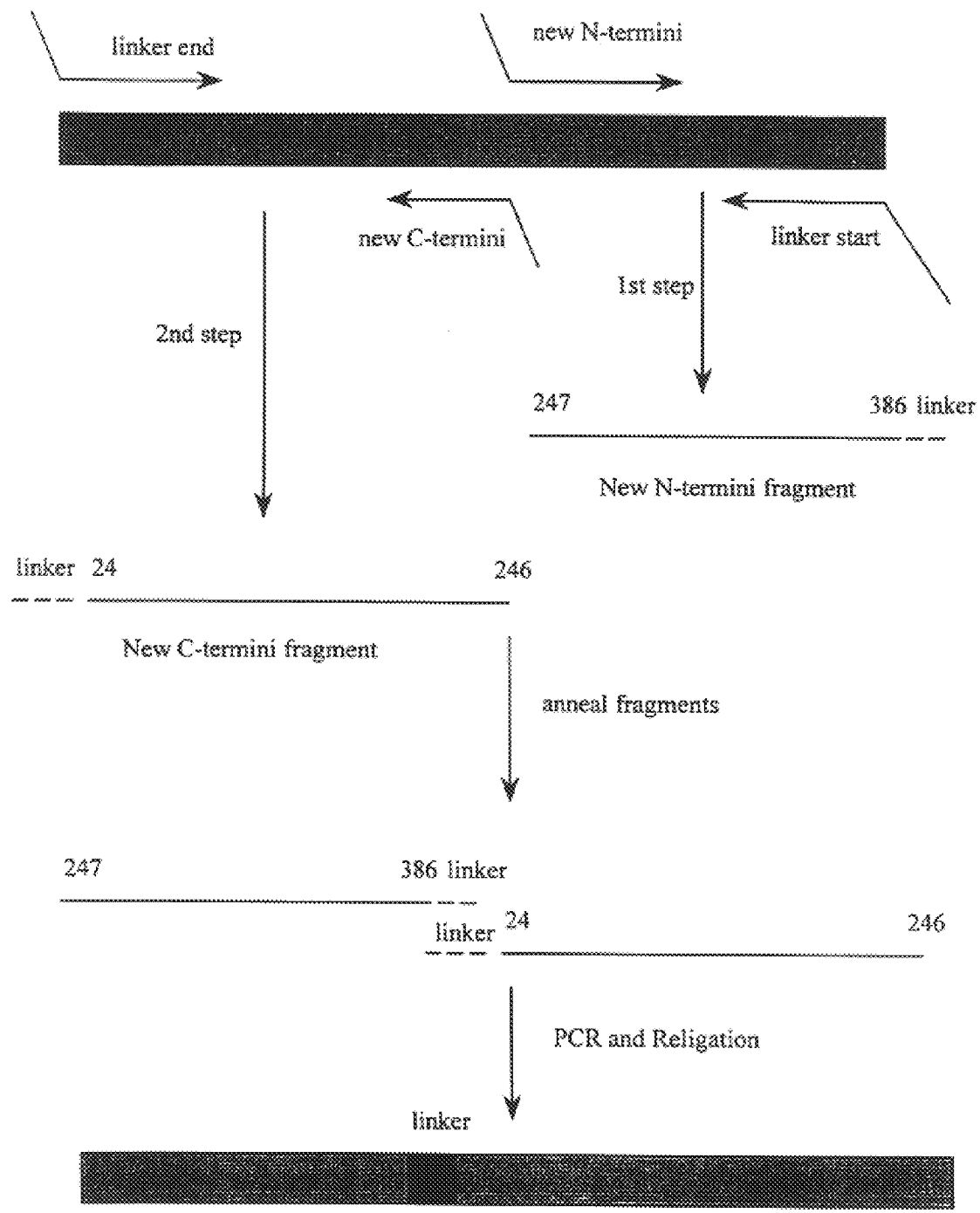

This example illustrates the construction and analysis of permuteins of patatin and patatin homologues. Nucleic acid sequences encoding permutein proteins having rearranged N-terminus/C-terminus protein sequences can be made by following the general method described by Mullins et al. (*J. Am. Chem. Soc.* 116: 5529–5533, 1994). The steps are shown in FIG. 10, and this example involves the design and use of a linker region separating the original C-terminus and N-terminus, but the use of a linker is not a critical or required element of permutein design.

Two sets of oligonucleotide primers are used in the construction of a nucleic acid sequence encoding a permutein protein. In the first step, oligonucleotide primers "new N-termini" and "linker start" are used in a PCR reaction to create amplified nucleic acid molecule "new N-termini fragment" that contains the nucleic acid sequence encoding the new N-terminal portion of the permutein protein, followed by the polypeptide linker that connects the C-terminal and N-terminal ends of the original protein. In the second step, oligonucleotide primers "new C-termini" and "linker end" are used in a PCR reaction to create amplified nucleic acid molecule "new C-termini fragment" that contains the nucleic acid sequence encoding the same linker as used above, followed by the new C-termini portion of the permutein protein. The "new N-termini" and "new C-termini" oligonucleotide primers are designed to include appropriate restriction enzyme recognition sites which assist in the cloning of the nucleic acid sequence encoding the permutein protein into plasmids.

Any suitable PCR conditions and polymerase can be used. It is desirable to use a thermostable DNA polymerase with high fidelity to reduce or eliminate the introduction of sequence errors. Typical PCR conditions are 25 cycles 94° C. denaturation for 1 minute, 45° C. annealing for one minute and 72° C. extension for 2 minutes; plus one cycle 72° C. extension for 10 minutes. A 50 µL reaction contains 30 pmol of each primer and 1 µg of template DNA; and 1×PCR buffer with $MgCl_2$, 200 µM dGTP, 200 µM dATP, 200 µM dTTP, 200 µM dCTP, 2.5 units of Pwo DNA polymerase. PCR reactions are performed in RoboCycler Gradient 96 Temperature Cycler (Stratagene, La Jolla, Calif.).

The amplified "new N-termini fragment" and "new C-termini fragment" are annealed to form a template in a third PCR reaction to amplify the full-length nucleic acid sequence encoding the permutein protein. The DNA fragments "new N-termini fragment" and "new C-termini fragment" are resolved on a 1% TAE gel, stained with ethidium bromide, and isolated using the QIAquick Gel Extraction Kit (Qiagen, Valencia, Calif.). These fragments are combined in equimolar quantities with oligonucleotide primers "new N-termini" and "new C-termini" in the third PCR reaction. The conditions for the PCR are the same as used previously. PCR reaction products can be purified using the QIAquick PCR purification kit (Qiagen, Valencia, Calif.).

Alternatively, a linker sequence can be designed containing a restriction site, allowing direct ligation of the two amplified PCR products.

Construction of Plasmid pMON 37402

The patatin protein contains a trypsin protease sensitive site at the arginine amino acid at position 246, as determined by electrophoresis of a trypsin digest reaction. In order to determine if the exposed protease site is an antigenic epitope, a permutein was constructed using positions 246–247 as a breakpoint.

The nucleic acid sequence encoding the permutein protein in plasmid pMON 37402 was created using the method illustrated in FIG. 10 and described herein. Nucleic acid molecule "new N-termini fragment" was created and amplified from the sequence encoding patatin in plasmid pMON26820 using oligonucleotide primers 27 (SEQ ID NO:242 SEQ ID NO:43) and 48 (SEQ ID NO:243 SEQ ID NO:44). Nucleic acid molecule "new C-termini fragment" was created and amplified from the sequence encoding patatin in plasmid pMON26820 using oligonucleotide primers 47 (SEQ ID NO:244 SEQ ID NO:45) and 36 (SEQ ID NO:245 SEQ ID NO:46). The full-length nucleic acid molecule encoding the permutein protein was created and amplified from annealed fragments "new N-termini fragment" and "new C-termini fragment" using oligonucleotide primers 27 (SEQ ID NO:242 SEQ ID NO:43) and 36 (SEQ ID NO:245 SEQ ID NO:46).

The resulting amplified nucleic acid molecule was digested with restriction endonucleases XhoI and EcoRI, and purified using the QIAquick PCR purification kit (Qiagen, Valencia, Calif.). Plasmid pMON 26869 (derivative of pPIC9, Invitrogen, Carlsbad, Calif.) was digested with restriction endonucleases XhoI and EcoRI, and gel purified, resulting in an approximately 2900 base pair vector fragment. The purified restriction fragments were combined and ligated using T4 DNA ligase.

The ligation reaction mixture was used to transform E. coli strain DH5α cells (Life Technologies, Gaithersburg, Md.). Transformant bacteria were selected on ampicillin-containing plates. Plasmid DNA was isolated and sequenced to confirm the presence of the correct insert. The resulting plasmid was designated pMON 37402 (containing SEQ ID NO:20, encoding protein sequence SEQ ID NO:21).

Construction of Plasmid pMON 37405

Amino acids 201–202, near tyrosine 193, were chosen as a breakpoint for the construction of a permutein protein.

The nucleic acid sequence encoding the permutein protein in plasmid pMON 37405 was created using the method illustrated in FIG. 10 and described herein. Nucleic acid molecule "New N-termini fragment" was created and amplified from the sequence encoding patatin in plasmid pMON26820 using oligonucleotide primers 48 (SEQ ID NO:44) and 58 (SEQ ID NO:47). Nucleic acid molecule "New C-termini fragment" was created and amplified from the sequence encoding patatin in plasmid pMON26820 using oligonucleotide primers 47 (SEQ ID NO:45) and 59 (SEQ ID NO:47). The full-length nucleic acid molecule encoding the permutein protein was created and amplified from annealed fragments "New N-termini fragment" and "New C-termini fragment" using oligonucleotide primers 58 (SEQ ID NO:48) and 59 (SEQ ID NO:47).

The resulting amplified nucleic acid molecule was digested with restriction endonucleases XhoI and EcoRI, and purified using the QIAquick PCR purification kit (Qiagen, Valencia, Calif.). Plasmid pMON 26869 (derivative of pPIC9, Invitrogen, Carlsbad, Calif.) was digested with restriction endonucleases XhoI and EcoRI, and gel purified, resulting in an approximately 2900 base pair vector fragment. The purified restriction fragments were combined and ligated using T4 DNA ligase.

The ligation reaction mixture was used to transform E. coli strain DH5α cells (Life Technologies, Gaithersburg, Md.). Transformant bacteria were selected on ampicillin-containing plates. Plasmid DNA was isolated and sequenced to confirm the presence of the correct insert. The resulting plasmid was designated pMON 37405 (containing SEQ ID NO:22, encoding protein sequence SEQ ID NO:23).

Construction of Plasmid pMON 37406

Amino acids 183–184, adjacent to tyrosine 185, were chosen as a breakpoint for the construction of a permutein protein.

The nucleic acid sequence encoding the permutein protein in plasmid pMON 37406 was created using the method illustrated in FIG. 10 and described herein. Nucleic acid molecule "New N-termini fragment" was created and amplified from the sequence encoding patatin in plasmid pMON26820 using oligonucleotide primers 48 (SEQ ID NO:44) and 60 (SEQ ID NO:49). Nucleic acid molecule "New C-termini fragment" was created and amplified from the sequence encoding patatin in plasmid pMON26820 using oligonucleotide primers 47 (SEQ ID NO:45) and 61 (SEQ ID NO:50). The full-length nucleic acid molecule encoding the permutein protein was created and amplified from annealed fragments "New N-termini fragment" and "New C-termini fragment" using oligonucleotide primers 60 (SEQ ID NO:49) and 61 (SEQ ID NO:50).

The resulting amplified nucleic acid molecule was digested with restriction endonucleases XhoI and EcoRI, and purified using the QIAquick PCR purification kit (Qiagen, Valencia, Calif.). Plasmid pMON 26869 (derivative of pPIC9, Invitrogen, Carlsbad, Calif.) was digested with restriction endonucleases XhoI and EcoRI, and gel purified, resulting in an approximately 2900 base pair vector fragment. The purified restriction fragments were combined and ligated using T4 DNA ligase.

The ligation reaction mixture was used to transform E. coli strain DH5α cells (Life Technologies, Gaithersburg, Md.). Transformant bacteria were selected on ampicillin-containing plates. Plasmid DNA was isolated and sequenced to confirm the presence of the correct insert. The resulting plasmid was designated pMON37406 (containing SEQ ID NO:24, encoding protein sequence SEQ ID NO:25).

Construction of Plasmid pMON 37407

Amino acids 268–269, adjacent to tyrosine 270, were chosen as a breakpoint for the construction of a permutein protein.

The nucleic acid sequence encoding the permutein protein in plasmid pMON 37407 was created using the method illustrated in FIG. 10 and described herein. Nucleic acid molecule "New N-termini fragment" was created and amplified from the sequence encoding patatin in plasmid pMON26820 using oligonucleotide primers 48 (SEQ ID NO:44) and 62 (SEQ ID NO:51). Nucleic acid molecule "New C-termini fragment" was created and amplified from the sequence encoding patatin in plasmid pMON26820 using oligonucleotide primers 47 (SEQ ID NO:45) and 63 (SEQ ID NO:52). The full-length nucleic acid molecule encoding the permutein protein was created and amplified from annealed fragments "New N-termini fragment" and "New C-termini fragment" using oligonucleotide primers 62 (SEQ ID NO:51) and 63 (SEQ ID NO:52).

The resulting amplified nucleic acid molecule was digested with restriction endonucleases XhoI and EcoRI, and purified using the QIAquick PCR purification kit (Qiagen, Valencia, Calif.). Plasmid pMON 26869 (derivative of pPIC9, Invitrogen, Carlsbad, Calif.) was digested with restriction endonucleases XhoI and EcoRI, and gel purified, resulting in an approximately 2900 base pair vector fragment. The purified restriction fragments were combined and ligated using T4 DNA ligase.

The ligation reaction mixture was used to transform *E. coli* strain DH5α cells (Life Technologies, Gaithersburg, Md.). Transformant bacteria were selected on ampicillin-containing plates. Plasmid DNA was isolated and sequenced to confirm the presence of the correct insert. The resulting plasmid was designated pMON37407 (containing SEQ ID NO:26, encoding protein sequence SEQ ID NO:27).

Construction of plasmid pMON 37408

Amino acids 321–322, near tyrosine 216, were chosen as a breakpoint for the construction of a permutein protein.

The nucleic acid sequence encoding the permutein protein in plasmid pMON 37408 was created using the method illustrated in FIG. 10 and described herein. Nucleic acid molecule "New N-termini fragment" was created and amplified from the sequence encoding patatin in plasmid pMON26820 using oligonucleotide primers 48 (SEQ ID NO:44) and 64 (SEQ ID NO:53). Nucleic acid molecule "New C-termini fragment" was created and amplified from the sequence encoding patatin in plasmid pMON26820 using oligonucleotide primers 47 (SEQ ID NO:45) and 65 (SEQ ID NO:54). The full-length nucleic acid molecule encoding the permutein protein was created and amplified from annealed fragments "New N-termini fragment" and "New C-termini fragment" using oligonucleotide primers 64 (SEQ ID NO:53) and 65 (SEQ ID NO:54).

The resulting amplified nucleic acid molecule was digested with restriction endonucleases XhoI and EcoRI, and purified using the QIAquick PCR purification kit (Qiagen, Valencia, Calif.). Plasmid pMON 26869 (derivative of pPIC9, Invitrogen, Carlsbad, Calif.) was digested with restriction endonucleases XhoI and EcoRI, and gel purified, resulting in an approximately 2900 base pair vector fragment. The purified restriction fragments were combined and ligated using T4 DNA ligase.

The ligation reaction mixture was used to transform *E. coli* strain DH5α cells (Life Technologies, Gaithersburg, Md.). Transformant bacteria were selected on ampicillin-containing plates. Plasmid DNA was isolated and sequenced to confirm the presence of the correct insert. The resulting plasmid was designated pMON37408 (containing SEQ ID NO:28, encoding protein sequence SEQ ID NO:29).

Production of Permutein proteins in *Pichia pastoris*

Plasmids pMON37402, pMON37405, pMON37406, pMON37407, and pMON37408 were individually used to electroporate KM71 cells from *Pichia pastoris* according to the procedure supplied by the manufacturer (Invitrogen, Carlsbad, Calif.). The resulting transformed cells were used to produce protein in *Pichia pastoris* following the procedure supplied by the manufacturer (Invitrogen, Carlsbad, Calif.).

The concentration of patatin in the culture was determined using a patatin ELISA assay and the enzyme activity was measured using the method of Hofgen and Willmitzer (*Plant Science*, 66: 221–230, 1990). The variants containing multiple mutations were further purified using Mono Q and hydrophobic interaction chromatography (HIC). Each culture was purified by first sizing on YM10 membranes (Amicon, Mass.) to a [>10 kDa] fraction, followed by chromatography on the Mono Q HR 10/10 column (Pharmacia, New Jersey). For chromatography on the Mono Q column, the samples were loaded on the column in 25 mM Tris pH 7.5 and eluted with a gradient of 1.0 M KCl in 25 mM Tris pH 7.5. Fractions containing patatin protein were determined using SDS-PAGE. For chromatography on the HIC column, the appropriate fractions were pooled and dialyzed into 1 M ammonium sulfate in 25 mM Tris pH 7.5. The dialyzed sample was then loaded on 16/10 phenyl Sepharose column (Pharmacia, N.J.) and eluted with a gradient of 25 mM Tris pH7.5.

The protein concentration was determined using the Bradford method, using BSA as a standard. SDS-PAGE analysis showed that these proteins were essentially pure. The esterase activity of the variants are shown in Table 3.

TABLE 3

| Activity of permuteins | | |
|---|---|---|
| enzyme | Breakpoint | Activity ($\Delta OD\ min^{-1}\ \mu g^{-1}$) |
| Native SEQ ID NO: 1 |  | 83.21 |
| pMON37402 SEQ ID NO: 21 | 246/247 | 66.7 |
| pMON37405 SEQ ID NO: 23 | 201/202 | No expression |
| pMON37406 SEQ ID NO: 25 | 183/184 | No expression |
| pMON37407 SEQ ID NO: 27 | 268/269 | 12.1 |
| pMON37408 SEQ ID NO: 29 | 321/322 | No expression |

The activity was determined using p-nitrophenyl caprate substrate as described by Hofgen and Willmitzer (*Plant Science*, 66: 221–230, 1990).

Insect Bioefficacy Assays

Assays for activity against larvae of SCRW are carried out by overlaying the test sample on an agar diet similar to that described by Marrone (*J. Econ. Entom.* 78: 290–293, 1985). Test samples were prepared in 25 mM Tris, pH 7.5 buffer. Neonate larvae are allowed to feed on the treated diet at 26° C., and mortality and growth stunting were evaluated after 5 or 6 days. The results of this assay are shown in Table 4.

TABLE 4

Insect bioefficacy assay

| Protein (200 ppm) | Mean Survival Weight | % Weight Reduction |
|---|---|---|
| Tris buffer (control) | 1.26 ± 0.3 | — |
| Wild Type | 0.21 ± 0.02 | 83 |
| pMON37402 | 0.21 ± 0.03 | 83 |
| pMON37407 | 0.32 ± 0.04 | 75 |

These data demonstrate that the growth of the SCRW larvae is similarly reduced upon ingestion of the proteins encoded by pMON37402 and pMON37407 as compared to the wild type patatin protein.

Permutein Sequences Improved for Monocot Expression

Modification of coding sequences has been demonstrated above to improve expression of insecticidal proteins. A modified coding sequence was thus designed to improve expression in plants, especially corn (SEQ ID NO:31).

Construction of pMON40701 for Monocot Expression

Plasmid pMON19767 was digested with restriction endonucleases NcoI and EcoRI and the 1100 bp gene fragment was purified using the QIAquick PCR purification kit (Qiagen, Valencia, Calif.). Plasmid pMON33719 was digested with restriction endonucleases NcoI and EcoRI, and gel purified, resulting in an approximately 3900 base pair vector fragment. The two purified restriction fragments were combined and ligated using T4 DNA ligase.

The ligation reaction mixture was used to transform *E. coli* strain DH5α cells (Life Technologies, Gaithersburg, Md.). Transformant bacteria were selected on ampicillin-containing plates. Plasmid DNA was isolated and sequenced to confirm the presence of the correct insert. The resulting plasmid was designated pMON40700. Plasmid pMON40700 was digested with restriction endonuclease NotI and the resulting 2200 bp DNA fragment was purified using the QIAquick PCR purification kit (Qiagen, Valencia, Calif.). Plasmid pMON30460 was digested with restriction endonuclease NotI, and gel purified, resulting in an approximately 4200 base pair vector fragment. The two purified restriction fragments were combined and ligated using T4 DNA ligase.

The ligation reaction mixture was used to transform *E. coli* strain DH5α cells (Life Technologies, Gaithersburg, Md.). Transformant bacteria were selected on kanamycin-containing plates. The resulting plasmid was designated pMON40701 (containing SEQ ID NO:30, encoding protein sequence SEQ ID NO:3 1).

Construction of pMON40703 for Monocot Expression

The nucleic acid sequence encoding the permutein protein in plasmid pMON40703 was created using the method illustrated in FIG. 10 and described herein. Nucleic acid molecule "New N-termini fragment" was created and amplified from the sequence encoding patatin in plasmid pMON19767 using oligonucleotide primers Syn1 (SEQ ID NO:55) and Syn2 (SEQ ID NO:56). Nucleic acid molecule "New C-termini fragment" was created and amplified from the sequence encoding patatin in plasmid pMON19767 using oligonucleotide primers Syn3 (SEQ ID NO:57) and Syn4 (SEQ ID NO:58). The full-length nucleic acid molecule encoding the permutein protein was created and amplified from annealed fragments "New N-termini fragment" and "New C-termini fragment" using oligonucleotide primers Syn1 (SEQ ID NO:55) and Syn4 (SEQ ID NO:58).

The resulting amplified nucleic acid molecule was digested with restriction endonucleases NcoI and EcoRI, and purified using the QIAquick PCR purification kit (Qiagen, Valencia, Calif.). Plasmid pMON33719 was digested with restriction endonucleases NcoI and EcoRI, and gel purified, resulting in an approximately 3900 base pair vector fragment. The purified restriction fragments were combined and ligated using T4 DNA ligase.

The ligation reaction mixture was used to transform *E. coli* strain DH5α cells (Life Technologies, Gaithersburg, Md.). Transformant bacteria were selected on ampicillin-containing plates. Plasmid DNA was isolated and sequenced to confirm the presence of the correct insert. The resulting plasmid was designated pMON40702. Plasmid pMON40702 was digested with NotI, and the resulting 2200 bp DNA fragment was purified using the QIAquick PCR purification kit (Qiagen, Valencia, Calif.). Plasmid pMON30460 was digested with restriction endonuclease NotI, and gel purified, resulting in an approximately 4200 base pair vector fragment. The purified restriction fragments were combined and ligated using T4 DNA ligase.

The ligation reaction mixture was used to transform *E. coli* strain DHR5α cells (Life Technologies, Gaithersburg, Md.). Transformant bacteria were selected on kanamycin-containing plates. The resulting plasmid was designated pMON40703 (containing SEQ ID NO:32, encoding protein sequence SEQ ID NO:33). Plasmid pMON40703 encodes a permutein protein with a "breakpoint" at positions 246/247 of the wild type patatin protein sequence (SEQ ID NO:38). The first 23 amino acids of SEQ ID NO:39 are a signal peptide sequence which is cleaved in the mature protein.

Construction of pMON40705 for Monocot Expression

The nucleic acid sequence encoding the permutein protein in plasmid pMON40705 was created using the method illustrated in FIG. 10 and described herein. Nucleic acid molecule "New N-termini fragment" was created and amplified from the sequence encoding patatin in plasmid pMON 19767 using oligonucleotide primers Syn10 (SEQ ID NO:59) and Syn2 (SEQ ID NO:56). Nucleic acid molecule "New C-termini fragment" was created and amplified from the sequence encoding patatin in plasmid pMON19767 using oligonucleotide primers Syn3 (SEQ ID NO:57) and Syn11 (SEQ ID NO:60). The full-length nucleic acid molecule encoding the permutein protein was created and amplified from annealed fragments "New N-termini fragment" and "New C-termini fragment" using oligonucleotide primers Syn10 (SEQ ID NO:59) and Syn11 (SEQ ID NO:60).

The resulting amplified nucleic acid molecule was digested with restriction endonucleases NcoI and EcoRI, and purified using the QIAquick PCR purification kit (Qiagen, Valencia, Calif.). Plasmid pMON33719 was digested with restriction endonucleases NcoI and EcoRI, and gel purified, resulting in an approximately 3900 base pair vector fragment. The purified restriction fragments were combined and ligated using T4 DNA ligase.

The ligation reaction mixture was used to transform *E. coli* strain DHR5α cells (Life Technologies, Gaithersburg, Md.). Transformant bacteria were selected on ampicillin-containing plates. Plasmid DNA was isolated and sequenced to confirm the presence of the correct insert. The resulting plasmid was designated pMON40704. Plasmid pMON40704 was digested with restriction endonuclease NotI, and the resulting 2200 bp DNA fragment was purified using the QIAquick PCR purification kit (Qiagen, Valencia, Calif.). Plasmid pMON30460 was digested with restriction endonuclease NotI, and gel purified, resulting in an approximately 4200 base pair vector fragment. The purified restriction fragments were combined and ligated using T4 DNA ligase.

The ligation reaction mixture was used to transform *E. coli* strain DH5α cells (Life Technologies, Gaithersburg, Md.). Transformant bacteria were selected on plates containing kanamycin. The resulting plasmid was designated pMON40705 (containing SEQ ID NO:34, encoding protein sequence SEQ ID NO:35). Plasmid pMON40705 encodes a permutein protein with a "breakpoint" at positions 268/269 of the wild type patatin protein sequence (SEQ ID NO:39). The first 23 amino acids of SEQ ID NO:2 are a signal peptide sequence which is cleaved in the mature protein.

Transient Expression of Protein in Corn Leaf Protoplasts

Plasmids pMON40701, pMON40703, and pMON40705 (all containing the native signal sequence for vacuolar targeting) were separately electroporated into corn leaf protoplasts as described by Sheen (*Plant Cell* 3: 225–245, 1991). Protein was extracted with glass beads and the supernatant was assayed for protein expression using ELISA for patatin and NPTII. Expression of protein by the transformed corn protoplasts was confirmed by Western blot analysis. Expression results are shown in Table 5.

TABLE 5

ELISA data

| enzyme | Patatin ELISA (μg/mL) | NPTII ELISA (μg/mL) | Normalized Expression (Patatin ELISA/ NPTII ELISA) |
|---|---|---|---|
| pMON40701 SEQ ID NO: 31 | 1.1 | 0.6 | 1.8 |
| pMON40703 SEQ ID NO: 33 | 2.1 | 0.3 | 7.0 |
| pMON40705 SEQ ID NO: 35 | 1.3 | 0.6 | 2.2 |

The results indicate that the permutein encoded by plasmid pMON40703 surprisingly shows approximately 4-fold higher expression compared to the wild type enzyme.

Example 7

This example illustrates the positions of critical amino acid residues in patatin and homologs.

TABLE 6

Positions of Critical Amino Acid Residues in Patatin and Homologs

| Enzyme | Catalytic Residue | | Other |
|---|---|---|---|
| | Ser | Asp | His/Arg |
| Pat 17 | 77 | 215 | 109 |
| PatFm | 55 | 194 | 87 |
| PatIm | 55 | 193 | 87 |
| PatL+ | 77 | 215 | 109 |
| PatA+ | 77 | 215 | 109 |
| PatB+ | 77 | 215 | 109 |
| Pentin 1 | 82 | 222 | 116 |
| 5C9 | 72 | 223 | 104 |
| Corn 3 | 72 | 223 | 104 |
| Corn 2 | 72 | 223 | 104 |
| Corn 4 | 72 | 223 | 104 |
| Corn 1 | 108 | 260 | 140 |
| Corn 5 | 72 | 223 | 104 |

In view of the above, it will be seen that the several advantages of the invention are achieved and other advantageous results attained.

As various changes could be made in the above methods and compositions without departing from the scope of the invention, it is intended that all matter contained in the above description, and shown in the accompanying drawings, shall be interpreted as illustrative and not in a limiting sense.

REFERENCES

1. Ganal, M., et al., *Genetic and physical mapping of the patatin genes in potato and tomato*. Mol Gen Genetics, 1991. 225: p. 501–509.
2. Vancanneyt, G., et al., *Expression of a patatin-like protein in the anthers of potato and sweet pepper flowers*. Plant Cell, 1989. 1: p. 533–540.
3. Hofgen, R. and L. Willmitzer, *Biochemical and genetic analysis of different patatin isoforms expressed in various organs of potato (Solanum tuberosum)*. Plant Sci., 1990. 66: p. 221–230.
4. Mignery, G. A., et al., *Isolation and sequence analysis of cDNAs for the major potato tuber protein, patatin*. Nucleic Acids Research, 1984. 12: p. 7987–8000.
5. Mignery, G. A., C. S. Pikaard, and W. D. Park, *Molecular characterization of the patatin multigene family of potato*. Gene, 1988. 62: p. 27–44.
6. Stiekema, W. J., et al., *Molecular cloning and analysis of four potato tuber mRNAs*. Plant Mol Biol, 1988. 11: p. 255–269.
7. Hirayama, O., et al., *Purification and properties of a lipid cyl-hydrolase from potato tubers*. Biochim Biophys Acta, 1975. 384: p. 127–137.
8. Wardale, D. A., *Lipid-degrading enzymes from potato tubers*. Phytochemistry, 1980. 19: p. 173–177.
9. Strickland, J. A., G. L. Orr, and T. A. Walsh, *Inhibition of Diabrotica larval growth by patatin, the lipid acyl hydrolase from potato tubers*. Plant Physiol, 1995. 109: p. 667–674.
10. English, L., et al., *Modulation of delta-endotoxin ion channels*. Molecular action of insecticides on ion channels, ed. J. M. Clark. Vol. 591. 1995: Amer. Chem. Soc. Symposium. 302–307.
11. Schnepf, E., et al., *Bacillus thringiensis and its pesticidal crystal proteins*. Microbiology and molecular biology reviews, 1998. 62: p. 775–806.
12. Crickmore, N., et al., *Revision of the nomeclature for the Bacillus thuringiensis pesticidal crystal proteins*. Microbiology and Molecular Biology Reviews, 1998.62: p. 807–813.
13. Tabashnik, B. E., et al., *Cross-resistance of the diamondback moth indicates altered interactions with domain II of Bacillus thringiensis toxins*. Applied and Environmental Microbiology, 1996. 62: p. 2839–2844.
14. Rosahl, S., et al., *Isolation and characterization of a gene from Solanum tuberosum encoding patatin, the major storage protein of potato tubers*. Mol Gen Genet, 1986. 203: p. 214–220.
15. Senda, K., et al., *A cytosolic phospholipase A2 from potato tissues appears to be patatin*. Plant Cell Physiol, 1996. 37: p. 347–353.
16. Schrag, J. D., et al., *Ser-His-Glu triad forms the catalytic site of the lipase from Geotrichum candidum*. Nature, 1991. 351: p. 761–764.
17. Cunningham, B. and J. Wells, *High-Resolution Epitope Mapping of hGH-Receptor Interactions by Alanine-Scanning Mutagenesis*. Science, 1989. 244: p. 1081–1085.
18. Bennett, W. F., et al., *High resolution analysis of functional determinants on human tissue-type plasminogen activator*. J Biol Chem, 1991.266: p. 5191–5201.
19. Dessen, A., et al., *Crystal structure of human cytosolic phospholipase $A_2$ reveals a novel topology and catalytic mechanism*. Cell, 1999. 97: p. 349–360.
20. Kunkel, D. A., *Rapid and efficient site-specific mutagenesis without phenotypic selection*. Proc Natl Acad Sci USA, 1985. 82: p. 477–92.

21. Marrone, P., et al., *Improvements in laboratory rearing of the southern corn rootworm, Diabrotica undecimpuncta howardi barber (coleoptera: chrysomelidae), on an artificial diet and corn.* J. Econ. Entom., 1985. 78: p. 290–3.
22. Ollis, D. L., et al., *The a/b hydrolase fold.* Protein Engineering, 1992. 5: p. 197–211.
23. Paetzel, M. and N. Strynadka, *Common protein architecture and binding sites in proteases utilizing a Ser/Lys dyad mechanism.* Protein Science, 1999. 8: p. 2533–2536.
24. Paetzel, M. and R. Dalbey, *Catalytic hydroxyl/amine dyads within serine proteases.* Trends Biochem Sci, 1997. 22: p. 28–31.
25. Slilaty, S. and J. Little, *Lysine 156 and Serine 119 are required for LexA repressor cleavage: A possible mechanism.* Proc Natl Acad Sci USA, 1987. 84: p. 3987–3991.
26. Tschantz, W., et al., *A serine and a lysine residue implicated in the catalytic mechanism of the E. coli leader peptidase.* J Biol Chem, 1993. 268: p. 27349–27354.

What is claimed is:

1. An isolated peptide exhibiting lipid acyl hydrolase activity and corn rootworm insect inhibitory bioactivity and consisting of the amino acid sequence as set forth in SEQ ID NO:21.

2. An isolated peptide consisting of the amino acid sequence as set forth in SEQ ID NO:21.

* * * * *